(12) United States Patent
Maeder et al.

(10) Patent No.: US 11,566,263 B2
(45) Date of Patent: Jan. 31, 2023

(54) COMPOSITIONS AND METHODS FOR TREATING CEP290 ASSOCIATED DISEASE

(71) Applicant: EDITAS MEDICINE, INC., Cambridge, MA (US)

(72) Inventors: Morgan Lee Maeder, Jamaican Plain, MA (US); Rina J. Mepani, Belmont, CA (US); Michael Stefanidakis, Brookline, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 683 days.

(21) Appl. No.: 16/322,922

(22) PCT Filed: Aug. 2, 2017

(86) PCT No.: PCT/US2017/045191
§ 371 (c)(1),
(2) Date: Aug. 27, 2019

(87) PCT Pub. No.: WO2018/026976
PCT Pub. Date: Feb. 8, 2018

(65) Prior Publication Data
US 2019/0169652 A1    Jun. 6, 2019

Related U.S. Application Data

(60) Provisional application No. 62/370,202, filed on Aug. 2, 2016, provisional application No. 62/400,526, filed on Sep. 27, 2016, provisional application No. 62/443,568, filed on Jan. 6, 2017, provisional application No. 62/503,800, filed on May 9, 2017, provisional application No. 62/535,193, filed on Jul. 20, 2017.

(51) Int. Cl.
| | | |
|---|---|---|
| C12N 15/90 | (2006.01) | |
| A61K 35/761 | (2015.01) | |
| A61K 9/00 | (2006.01) | |
| C12N 15/11 | (2006.01) | |
| C12N 9/22 | (2006.01) | |
| C12N 15/113 | (2010.01) | |
| C12N 15/86 | (2006.01) | |

(52) U.S. Cl.
CPC .......... *C12N 15/907* (2013.01); *A61K 9/0048* (2013.01); *A61K 35/761* (2013.01); *C12N 9/22* (2013.01); *C12N 15/11* (2013.01); *C12N 15/113* (2013.01); *C12N 15/86* (2013.01); *C12N 2310/20* (2017.05); *C12N 2320/32* (2013.01); *C12N 2330/50* (2013.01); *C12N 2330/51* (2013.01); *C12N 2750/14143* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,443,505 A | 8/1995 | Wong et al. |
| 5,766,242 A | 6/1998 | Wong et al. |
| 5,869,624 A | 2/1999 | Hasel et al. |
| 6,251,090 B1 | 6/2001 | Avery et al. |
| 6,299,895 B1 | 10/2001 | Hammang et al. |
| 6,413,540 B1 | 7/2002 | Yaacobi |
| 6,416,777 B1 | 7/2002 | Yaacobi |
| 6,586,240 B1 | 7/2003 | Singer et al. |
| 7,985,581 B2 | 7/2011 | Pachuk et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,394 B2 | 11/2014 | Chalasani et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |

(Continued)

FOREIGN PATENT DOCUMENTS

| | | |
|---|---|---|
| KR | 2001/0048693 A | 6/2001 |
| WO | 2000/040089 A1 | 7/2000 |

(Continued)

OTHER PUBLICATIONS

U.S. Appl. No. 61/652,086, filed May 25, 2012, Jinek et al.
U.S. Appl. No. 61/716,256, filed Oct. 19, 2012, Jinek et al.
U.S. Appl. No. 61/734,256, filed Dec. 6, 2012, Chen et al.
U.S. Appl. No. 61/736,527, filed Dec. 12, 2012, Zhang et al.
U.S. Appl. No. 61/738,355, filed Dec. 17, 2012, Church et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/779,169, filed Mar. 13, 2013, Mali et al.

(Continued)

*Primary Examiner* — Robert M Kelly
(74) *Attorney, Agent, or Firm* — Perkins Coie LLP; Courtney Prochnow

(57) ABSTRACT

Nucleic acids and viral vectors, particularly adeno-associated virus (AAV) vectors are provided that encode Cas9 and paired guide RNAs. The nucleic acids and vectors, and compositions that comprise them, can be used in methods to treat subjects, to alter cells in subjects who may suffer from an inherited retinal dystrophy such as CEP290 associated disease or who may be in need of alteration of a cell or a cellular nucleic acid sequence associated with an inherited retinal dystrophy such as the CEP290 gene, and/or to treat inherited retinal dystrophies including CEP290 associated disease.

28 Claims, 14 Drawing Sheets

Specification includes a Sequence Listing.

(56) References Cited

U.S. PATENT DOCUMENTS

| | | | |
|---|---|---|---|
| 9,163,259 B2 | 10/2015 | Choi et al. | |
| 9,322,037 B2 | 4/2016 | Liu et al. | |
| 9,499,847 B2 | 11/2016 | Porter et al. | |
| 9,938,521 B2* | 4/2018 | Maeder | C12N 15/86 |
| 10,253,312 B2* | 4/2019 | Maeder | C12N 15/1024 |
| 11,028,388 B2* | 6/2021 | Maeder | C12N 9/22 |
| 2003/0186238 A1 | 10/2003 | Allawi et al. | |
| 2007/0020627 A1 | 1/2007 | Barbas | |
| 2010/0055793 A1 | 3/2010 | Chandrasegaran et al. | |
| 2010/0055798 A1 | 3/2010 | Battersby | |
| 2010/0076057 A1 | 3/2010 | Sontheimer et al. | |
| 2011/0059502 A1 | 3/2011 | Chalasani | |
| 2011/0189776 A1 | 8/2011 | Terns et al. | |
| 2011/0223638 A1 | 9/2011 | Wiedenheft et al. | |
| 2011/0236894 A1 | 9/2011 | Rao et al. | |
| 2011/0301073 A1 | 12/2011 | Gregory et al. | |
| 2012/0270273 A1 | 10/2012 | Zhang et al. | |
| 2013/0130248 A1 | 5/2013 | Haurwitz et al. | |
| 2013/0253040 A1 | 9/2013 | Miller et al. | |
| 2014/0068797 A1 | 3/2014 | Doudna et al. | |
| 2014/0179770 A1 | 6/2014 | Zhang et al. | |
| 2014/0242699 A1 | 8/2014 | Zhang | |
| 2014/0309177 A1 | 10/2014 | Perez-Pinera et al. | |
| 2014/0315985 A1 | 10/2014 | May et al. | |
| 2014/0335620 A1 | 11/2014 | Zhang et al. | |
| 2014/0342456 A1 | 11/2014 | Mali et al. | |
| 2014/0342457 A1 | 11/2014 | Mali et al. | |
| 2014/0342458 A1 | 11/2014 | Mali et al. | |
| 2014/0356958 A1 | 12/2014 | Mali et al. | |
| 2015/0056705 A1 | 2/2015 | Conway et al. | |
| 2015/0232833 A1 | 8/2015 | Mali et al. | |
| 2015/0252358 A1 | 9/2015 | Maeder et al. | |
| 2015/0259704 A1 | 9/2015 | Church et al. | |
| 2016/0153005 A1 | 6/2016 | Zhang et al. | |
| 2016/0281111 A1 | 9/2016 | Cotta-Ramusino et al. | |
| 2016/0324987 A1 | 11/2016 | Wang et al. | |
| 2016/0340661 A1 | 11/2016 | Cong et al. | |
| 2017/0058298 A1 | 3/2017 | Kennedy et al. | |
| 2018/0291370 A1 | 10/2018 | Gersbach et al. | |

FOREIGN PATENT DOCUMENTS

| | | |
|---|---|---|
| WO | 2001/028474 A1 | 4/2001 |
| WO | 2002/089767 A1 | 11/2002 |
| WO | 2003/072788 A1 | 9/2003 |
| WO | 2008/108989 A2 | 9/2008 |
| WO | 2009/121536 A1 | 10/2009 |
| WO | 2010/054108 A9 | 5/2010 |
| WO | 2011/012724 A1 | 2/2011 |
| WO | 2011/143124 A2 | 11/2011 |
| WO | 2011/146121 A1 | 11/2011 |
| WO | 2011/154520 A1 | 12/2011 |
| WO | 2012/145601 A2 | 10/2012 |
| WO | 2012/164565 A8 | 12/2012 |
| WO | 2012/168435 A1 | 12/2012 |
| WO | 2013/012674 A1 | 1/2013 |
| WO | 2013/066438 A2 | 5/2013 |
| WO | 2013/082519 A2 | 6/2013 |
| WO | 2013/098244 A1 | 7/2013 |
| WO | 2013/141680 A1 | 9/2013 |
| WO | 2013/142578 A1 | 9/2013 |
| WO | 2013/163628 A2 | 10/2013 |
| WO | 2013/176772 A1 | 11/2013 |
| WO | 2013/181228 A1 | 12/2013 |
| WO | 2014/018423 A8 | 1/2014 |
| WO | 2014/022702 A2 | 2/2014 |
| WO | 2014/036219 A2 | 3/2014 |
| WO | 2014/059255 A1 | 4/2014 |
| WO | 2014/065596 A1 | 5/2014 |
| WO | 2014/089290 A1 | 6/2014 |
| WO | 2014/093479 A1 | 6/2014 |
| WO | 2014/093595 A1 | 6/2014 |
| WO | 2014/093622 A8 | 6/2014 |
| WO | 2014/093635 A9 | 6/2014 |
| WO | 2014/093655 A2 | 6/2014 |
| WO | 2014/093661 A2 | 6/2014 |
| WO | 2014/093694 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/099744 A1 | 6/2014 |
| WO | 2014/099750 A2 | 6/2014 |
| WO | 2014/124284 A1 | 8/2014 |
| WO | 2014/144288 A1 | 9/2014 |
| WO | 2014/144592 A2 | 9/2014 |
| WO | 2014/144761 A2 | 9/2014 |
| WO | 2014/152432 A2 | 9/2014 |
| WO | 2014/186585 A2 | 11/2014 |
| WO | 2014/197568 A2 | 12/2014 |
| WO | 2014/197748 A2 | 12/2014 |
| WO | 2014/204578 A1 | 12/2014 |
| WO | 2014/204725 A8 | 12/2014 |
| WO | 2015/006290 A1 | 1/2015 |
| WO | 2015/006294 A2 | 1/2015 |
| WO | 2015/006498 A2 | 1/2015 |
| WO | 2015/013583 A8 | 1/2015 |
| WO | 2015/020522 A1 | 2/2015 |
| WO | 2015/021353 A1 | 2/2015 |
| WO | 2015/027134 A1 | 2/2015 |
| WO | 2015/035136 A8 | 3/2015 |
| WO | 2015/035139 A2 | 3/2015 |
| WO | 2015/035162 A2 | 3/2015 |
| WO | 2015/048577 A2 | 4/2015 |
| WO | 2015/048690 A1 | 4/2015 |
| WO | 2015/070083 A1 | 5/2015 |
| WO | 2015/071474 A9 | 5/2015 |
| WO | 2015/077290 A2 | 5/2015 |
| WO | 2015/077318 A1 | 5/2015 |
| WO | 2015/089406 A1 | 6/2015 |
| WO | 2015/089462 A1 | 6/2015 |
| WO | 2015/099850 A1 | 7/2015 |
| WO | 2015/138510 A8 | 9/2015 |
| WO | 2015/188056 A1 | 12/2015 |
| WO | 2015/195621 A1 | 12/2015 |
| WO | 2016/022363 A9 | 2/2016 |
| WO | 2016/073990 A2 | 5/2016 |
| WO | 2016/182959 A1 | 11/2016 |
| WO | 2016/186772 A2 | 11/2016 |
| WO | 2016/205749 A1 | 12/2016 |
| WO | 2017/035416 A2 | 3/2017 |
| WO | 2017/184768 | 10/2017 |
| WO | 2018/009562 A1 | 1/2018 |
| WO | 2018/026976 A1 | 2/2018 |
| WO | 2018/126176 A1 | 7/2018 |
| WO | 2018/129368 A2 | 7/2018 |

OTHER PUBLICATIONS

U.S. Appl. No. 61/950,733, filed Mar. 10, 2014, Maeder et al.
U.S. Appl. No. 62/036,576, filed Aug. 12, 2014, Maeder et al.
U.S. Appl. No. 62/443,212.
Al-Attar, S., et al., "Clustered Regularly Interspaced Short Palindromic Repeats (CRISPRs): The Hallmark of an Ingenious Antiviral Defense Mechanism in Prokaryotes," Biol. Chem. 392:277-289 (2011).
Altschul, S. F., et al., "Gapped BLAST and PSI-BLAST: A New Generation of Protein Database Search Programs," Nucleic Acids Res. 25(17):3389-3402 (1997).
Altschul, S. F., et al., "Basic Local Alignment Search Tool," J. Mol. Biol. 215(3):403-410(1990).
Ambati, J., et al., "Diffusion of High Molecular Weight Compounds Through Sclera," Invest. Ophthalmol. Vis. Sci. 41(5):1181-1185 (2000).
Ambati, J., et al., "Transscleral Delivery of Bioactive Protein to the Choroid and Retina," Invest. Ophthalmol. Vis. Sci. 41(5):1186-1191 (2000).
Amrani, N., et al., "NmeCas9 is an Intrinsically High-Fidelity Genome-Editing Platform," Genome Biol. 19:214 (2018).
Anders, C., et al., "Structural Basis of PAM-Dependent Target DNA Recognition by the Cas9 Endonuclease," Nature 513(7519):569-573 (2014).
Andreas, S., et al., "Enhanced Efficiency Through Nuclear Localization Signal Fusion on Phage PhiC31-Integrase: Activity Com-

(56) References Cited

OTHER PUBLICATIONS parison with Cre and FLPe Recombinase in Mammalian Cells," Nucleic Acids Res. 30(11):2299-2306 (2002).
Anonymous, Third Party Observation for EP13818570.7, Oct. 1, 2014, 15 pages.
Anonymous, Third Party Observation for EP13824232.6, Sep. 8, 2014, 48 pages.
Anonymous, Third Party Observation for EP13824232.6, Sep. 22, 2014, 19 pages.
Anonymous, Third Party Observation for EP13824232.6, Oct. 22, 2014, 7 pages.
Baala, L., et al., "Pleiotropic Effects of CEP290 (NPHP6) Mutations Extend to Meckel Syndrome," Am. J. Hum. Genet. 81(1):170-179 (2007).
Bae, S., et al., "Cas-OFFinder: A Fast and Versatile Algorithm that Searches for Potential Off-Target Sites of Cas9 RNA-Guided Endonucleases," Bioinformatics 30(10):1473-1475 (2014).
Bainbridge, J.W., et al., "Effect of Gene Therapy on Visual Function in Leber's Congenital Amaurosis," N. Engl. J. Med. 358(21):2231-2239 (2008).
Baker, M., "Gene Editing at CRISPR Speed," Nat. Biotechnol. 32(4):309-312 (2014).
Barker, C. S., et al., "Increased DNA Microarray Hybridization Specificity Using sscDNA Targets," BMC Genomics 6:57 (2005).
Baron-Benhamou, J., et al., "Using the LambdaN Peptide to Tether Proteins to RNAs," Methods Mol. Biol. 257:135-153 (2004).
Barrangou, R., "RNA-Mediated Programmable DNA Cleavage," Nat. Biotechnol. 30(9):836-838 (2012).
Barretina, J., et al., "The Cancer Cell Line Encyclopedia Enables Predictive Modeling of Anticancer Drug Sensitivity," Nature 483(7391):603-607 (2012).
Bassett, A. R., et al., "CRISPR/Cas9 and Genome Editing in *Drosophila*," J. Genet. Genom. 41:7-19 (2014).
Beerli, R. R., et al., "Toward Controlling Gene Expresion at Will: Specific Regulation of the erbB-2/HER-2 Promoter by Using Polydactyl Zinc Finger Proteins Constructed from Modular Building Blocks," Proc. Natl. Acad. Sci. 95:14628-14633 (1998).
Bhaya, D., et al., "CRISPR-Cas Systems in Bacteria and Archaea: Versatile Small RNAs for Adaptive Defense and Regulation," Annu. Rev. Genet. 45:273-297 (2011).
Bikard, D., et al., "Programmable Repression and Activation of Bacterial Gene Expression Using an Engineered CRISPR-Cas System," Nucl. Acids Res. 41(15)7429-7437 (2013).
Bitinaite, J., et al., "FokI Dimerization is Required for DNA Cleavage," Proc. Natl. Acad. Sci. 95:10570-10575 (1998).
Boch, J., et al., "Breaking the Code of DNA Binding Specificity of TAL-Type III Effectors," Science 326(5959):1509-1512 (2009).
Boch, J., et al., "Xanthomonas AvrBs3 Family-Type III Effectors: Discovery and Function," Annu. Rev. Phytopathol. 48:419-436 (2010).
Bothmer, A., et al., "Characterization of the Interplay Between DNA Repair and CRISPR/Cas9-Induced DNA Lesions at an Endogenous Locus," Nat. Commun. 8:13905 (2017).
Boye, S. E., et al., "The Human Rhodopsin Kinase Promoter in an AAV5 Vector Confers Rod- and Cone-Specific Expression in the Primate Retina," Human Gene Therapy 23(10):1101-1115 (2012).
Briner, A.E., et al., "Guide RNA Functional Modules Direct Cas9 Activity and Orthogonality," Mol. Cell 56(2):333-339 (2014).
Broad Institute, Communication Forwarding Declaration of Feng Zhang for U.S. Appl. No. 14/256,912, filed Nov. 24, 2014, 5 pages.
Broad Institute, Information Disclosure Statement submitted for U.S. Appl. No. 14/256,912, citing Electronic Mail from T. Kowalski which references Briner et al., filed Nov. 3, 2014, 8 pages.
Broad Institute, Request for Oral Examination for EP138185707, dated Oct. 27, 2014, 3 pages.
Broad Institute, Response to EP Examination Report for EP13824232. 6, dated Dec. 31, 2014, 44 pages.
Broad Institute, Response to Third Party Observations and Request for Oral Hearing for EP13824232.6, Oct. 27, 2014, 9 pages.
Broad Institute, Response to Third Party Observations, with redlined and clean amended claims, for EP13818570.7, Oct. 16, 2014, 30 pages.
Broad Institute, Response to Third Party Observations, with redlined and clean amended claims, for EP13824232.6, Oct. 2, 2014, 16 pages.
Brummelkamp, T. R., et al., "A System for Stable Expression of Short Interfering RNAs in Mammalian Cells," Science 296(5567):550-553 (2002).
Burnight, E.R., et al., "CEP290 Gene Transfer Rescues Leber Congenital Amaurosis Cellular Phenotype," Gene Ther. 21:662-672 (2014).
Burstein, D., et al., "New CRISPR-Cas Systems from Uncultivated Microbes," Nature 542(7640):237-241 (2017).
Caldecott, K.W., "Single-Strand Break Repairand Genetic Disease," Nat. Rev. Genet. 9(8):619-631 (2008).
Canver, M. C., "Evaluation of the Clinical Success of Ex Vivo and In Vivo Gene Therapy," Journal of Young Investitgators, http://www.hyi.org/issue/evaluation-of-the-clinical-success-of-ex-vivo-and-in-vivo-gene-therapy/, 9 pages (2009).
Carroll, D., "A CRISPR Approach to Gene Targeting," Mol. Ther. 20(9):1658-1660 (2012).
Cassini, A., et al., "A Highly Specific SpCas9 Variant is Identified by In Vivo Screening in Yeast," Nat. Biotechnol. 36(3):265-271 (2018).
Cathomen, T., et al., "Zinc-Finger Nucleases: The Next Generation Emerges," Mol. Ther. 16:1200-1207 (2008).
Cermak, T., et al., "Efficient Design and Assembly of Custom TALEN and Other TAL Effector-Based Constructs for DNA Targeting," Nucl. Acids Res. 39(12):e82 (2011).
Chen, X., et al., "Fusion Protein Linkers: Property, Design and Functionality," Adv. Drug Deliv. Rev. 65(10):1357-1369 (2013).
Chen, F., et al., "Targeted Activation of Diverse CRISPR-Cas Systems for Mammalian Genome Editing Via Proximal CRISPR Targeting," Nat. Commun. 8:14958 (2017).
Chen, J. S., et al., "Enhanced Proofreading Governs CRISPR-Cas9 Targeting Accuracy," Nature 550(7676):407-410 (2017).
Cho, S. W., et al., Supplementary Information: Targeted Genome Engineering in Human Cells With the Cas9 RNA-Guided Endonuclease, Nature Biotechnology (Mar. 2013) vol. 31, No. 3, 11 pages.
Cho, S. W., et al., "Targeted Genome Engineering in Human Cells with the Cas9 RNA-Guided Endonuclease," Nat. Biotechnol. 31(3):230-232 (2013).
Christian, M., et al., "Targeting DNA Double-Strand Breaks With TAL Effector Nucleases," Genetics 186:757-761 (2010).
Christian, M., et al., "Targeting DNA Double-Strand Breaks With TAL Effector Nucleases," Genetics Supporting Information, 1SI-8SI (2010).
Chylinski, K., et al., "The TrackRNA and Cas9 Families of Type II CRISPR-Cas Immunity Systems," RNA Biol. 10(5):726-737 (2013).
Cideciyan, A.V., et al., "Human Gene Therapy for RPE65 Isomerase Deficiency Activates the Retinoid Cycle of Vision but with Slow Rod Kinetics," Proc. Natl. Acad. Sci. U.S.A. 105(39):15112-15117 (2008).
Cideciyan, A.V., et al., "Vision 1 Year After Gene Therapy for Leber's Congenital Amaurosis," N. Engl. J. Med. 361(7):725-727 (2009).
Cong, L., et al., "Multiplex Genome Engineering Using CRISPR/Cas Systems," Science 339(6121):819-823 (2013).
Cong, L. et al., "Supplementary Material: Multiplex Genome Engineering Using CRISPR-Cas Systems," Science Express (Jul. 5, 2012).
Cong, L. et al., "Supplementary Material: Multiplex Genome Engineering Using CRISPR-Cas Systems," Science Express (Jan. 3, 2013).
Coppieters, F., et al., "Genetic Screening of LCA in Belgium: Predominance of CEP290 and Identification of Potential Modifier Alleles in AHI1 of CEP290-Related Phenotypes," Hum. Mutat. 31(10):E1709-1766 (2010).
Cornish-Bowden, A., "Nomenclature for Incompletely Specified Bases in Nucleic Acid Sequences: Recommendations 1984," Nucleic Acids Res. 13(9):3021-3030 (1985).

(56) References Cited

OTHER PUBLICATIONS

Cradick, T. J., et al., "CRISPR/Cas9 Systems Targeting Beta-Globin and CCR5 Genes Have Substantial Off-Target Activity," Nucleic Acids Res. 41(20):9584-9592 (2013).
Datsenko, K. A., et al., "Molecular Memory of Prior Infections Activates the CRISPR/Cas Adaptive Bacterial Immunity System," Nat. Commun. 3:945 (2012).
Davis, L., et al., "Homology-Directed Repair of DNA Nicks Via Pathways Distinct from Canonical Double-Strand Break Repair," PNAS 111(10):E924-932 (2014).
Deltcheva, E., et al., CRISPR RNA Maturation by Trans-Encoded Small RNA and Host Factor RNase III, Nature 471:602-607 (2011).
Deltcheva, E., et al., Supplementary Figures: CRISPR RNA Maturation by Trans-Encoded Small RNA and Host Factor RNase III. Downloaded from www.nature.com/nature, p. 1-35, 2011.
Den Hollander, A.I., et al., "Mutations in the CEP290 (NPH6) Gene are a Frequent Cause of Leber Congenital Amaurosis," Am. J. Hum. Genet. 79(3):556-561 (2006).
Den Hollander, A.I., et al., "Leber Congenital Amaurosis: Genes, Proteins and Disease Mechanisms," Prog. Retin. Eye Res. 27(4):391-419 (2008).
Den Hollander, A.I., et al., "Lighting a Candle in the Dark: Advances in Genetics and Gene Therapy of Recessive Retinal Dystrophies," J. Clin. Invest. 120(9):3042-3053 (2010).
Deveau, H., et al., "Phage Response to CRISPR-Encoded Resistance in *Streptococcus thermophilus*," J. Bacteriol. 190(4):1390-1400 (2008).
DiCarlo, J. E., et al., "Genome Engineering in *Saccharomyces cerevisiae* Using CRISPR-Cas Systems," Nucl. Acids Res. 41(7):4336-43 (2013).
Dingwall, C., et al., "A Polypeptide Domain That Specifies Migration of Nucleoplasmin Into the Nucleus," Cell 30:449-458 (1982).
Dreszer, T. R., et al., "The UCSC Genome Browser Database: Extensions and Updates 2011," Nucl. Acids Res. 40:D918-D923 (2012).
Estrada-Cuzcano, A., et al., "IQCB1 Mutations in Patients with Leber Congenital Amaurosis," Invest. Opthalmol. Vis. Sci. 52(2):834-839 (2011).
Esvelt, K.M., et al., "A System for the Continuous Directed Evolution of Biomolecules," Nature 472(7344):499-503 (2011).
Esvelt, K. M., et al., "Orthogonal Cas9 Proteins for RNA-Guided Gene Regulation and Editing," Nat. Methods 10(11):1116-1121 (2013).
Fine, E.J., et al., "Trans-Spliced Cas9 Allows Cleavage of HBB and CCR5 Genes in Human Cells Using Compact Expression Cassettes," Sci. Rep. 5:10777 (2015).
Fonfara, I., et al., "Phylogeny of Cas9 Determines Functional Exchangeability of Dual-RNA and Cas9 Among Orthologous Type II CRISPR-Cas Systems," Nucl. Acids Res.42(4):2577-2590 (2014).
Friedland, A.E., et al., "Characterization of *Staphylococcus aureus* Cas9: A Smaller Cas9 for All-in-One Adeno-Associated Virus Delivery and Paired Nickase Applications," Genome Biol. 16:257 (2015).
Frit, P., et al., "Alternative End-Joining Pathway(s): Bricolage at DNA Breaks," DNA Repair (Amst) 17:81-97 (2014).
Fu, Y., et al., "High-Frequency Off-Target Mutagenesis Induced by CRISPR-Cas Nucleases in Human Cells," Nat. Biotechnol. 31:822-826 (2013).
Fu, Y., et al., "Targeted Genome Editing in Human Cells Using CRISPR/Cas Nucleases and Truncated Guide RNAs," Methods Enzymol. 546:21-45 (2014).
Fu, Y., et al., "Improving CRISPR-Cas Nuclease Specificity Using Truncated Guide RNAs," Nat. Biotechnol. 32(3):279-284 (2014).
Gabriel, R., et al., "An Unbiased Genome-Wide Analysis of Zinc-Finger Nuclease Specificity," Nat. Biotechnol. 29:816-823 (2011).
Garanto, A., et al., "Unexpected CEP290 mRNA Splicing in a Humanized Knock-In Mouse Model for Leber Congenital Amaurosis," PLoS One 8(11):e79369 (2013).
Garneau, J. E., et al., "The CRISPR-Cas Bacterial Immune Systems Cleaves Bacteriophage and Plasmid DNA," Nature 468:67-71 (2010).

Gasiunas, G., et al., "Cas9-crRNA Ribonucleoprotein Complex Mediates Specific DNA Cleavage for Adaptive Immunity in Bacteria," Proc. Natl. Acad. Sci. 109(39):E2579-E2586 (2012).
Genetics Home Reference: Your Guide to Understanding Genetic Conditions, "Senior-Loken Syndrome," Published by NIH U.S. National Library of Medicine, Bethesda, MD, 5 pages as printed Jan. 22, 2019.
Gilbert, L. A., et al., "CRISPR-Mediated Modular RNA-Guided Regulation of Transcription in Eukaryotes," Cell 154(2):442-451 (2013).
Goldfarb, D. S., et al., "Synthetic Peptides as Nuclear Localization Signals," Nature 322:641-644 (1986).
Gratz, S. J., et al., "Genome Engineering of *Drosophila* with the CRISPR RNA-Guided Cas9 Nuclease," Genetics 194(4):1029-1035 (2013).
Grieger, J. C., et al., "Production and Characterization of Adeno-Associated Viral Vectors," Nat. Protoc. 1(3):1412-1428 (2006).
Guilinger, J. P., et al., "Fusion of Catalytically Inactive Cas9 to FokI Nuclease Improves the Specificity of Genome Modification," Nat Biotechnol. 32(6):577-583 (2014).
Guo, X., et al., "RNA-Dependent Folding and Stabilization of C5 Protein During Assembly of the *E. coli* Rnase P Holoenzyme," J. Mol. Biol. 360:190-203 (2006).
Gustafsson, C., et al., "Codon Bias and Heterologous Protein Expression," Trends Biotechnol. 22(7):346-353 (2004).
Haft, D. H., et al., "A Guild of 45 CRISPR-Associated (Cas) Protein Families and Multiple CRISPR/Cas Subtypes Exist in Prokaryotic Genomes," PLoS Comput. Biol. 1(6):e60 (2005).
Hale, C. R., et al., "Essential Features and Rational Design of CRISPR RNAs That Function With the Cas RAMP Module Complex to Cleave RNAs," Mol. Cell 45(3):292-302 (2012).
Hatoum-Aslan, A., et al. "Mature Clustered Regularly Interspaced, Short Palindromic Repeats RNA 5,9,14 (crRNA) Length is Measured by a Ruler Mechanism Anchored at the Precursor Processing Site," Proc. Natl. Acad. Sci. 108(52):21218-21222 (2011).
Heigwer, F., et al., "E-CRISP: Fast CRISPR Target Site Identification," Nat. Methods 11(2):122-123 (2014).
Helou, J., et al., "Mutation Analysis of NPHP6/CEP290 in Patients with Joubert Syndrome and Senior-Loken Syndrome," J. Med. Genet. 44(10):657-663 (2007).
Hinz, J. M., et al., "Nucleosomes Selectively Inhibit Cas9 Off-Target Activity at a Site Located at the Nucleosome Edge," J. Biol. Chem. 291(48):24851-24856 (2016).
Hockemeyer, D., et al., "Efficient Targeting of Expressed and Silent Genes in Human ESCs and iPSCs Using Zinc-Finger Nucleases," Nat. Biotechnol. 27(9):851-857 (2009).
Hockemeyer, D., et al., "Genetic Engineering of Human luripotent Cells Using TALE Nucleases," Nat. Biotechnol. 29:731-734 (2011).
Holt, N, et al., "Zinc Finger Nuclease-Mediated CCR5 Konockout Hematopoietic Stem Cell Transplantation Controls HIV-1 In Vivo," Nat. Biotechnol. 28(8):839-847 (2010).
Horvath, P., et al., "CRISPR/Cas, The Immune System of Bacteria and Archaea," Science 327(5962):167-170 (2010).
Horvath, P., et al., "RNA-Guided Genome Editing A La Carte," Cell Res. 23:733-734 (2013).
Hou, Z., et al., "Efficient Genome Engineering in Human Pluripotent Stem Cells Using Cas9from Neisseria Meningitidis," Proc. Natl. Acad. Sci. U.S.A. 110(39):15644-15649 (2013).
Hsu, P.D., et al., "DNA Targeting Specificity of RNA-Guided Cas9 Nucleases," Nat. Biotechnol. 31(9):827-832 (2013).
Hwang, W. Y., et al., "Heritable and Precise Zebrafish Genome Editing Using a CRISPR-Cas System," PLoS One 8(7):e68708 (2013).
Hwang, W. Y., et al., "Efficient Genome Editing in Zebrafish Using a CRISPR-Cas System," Nat. Biotechnol. 31(3):227-229 (2013).
Iyama, T., et al., "DNA Repair Mechanisms in Dividing and Non-Dividing Cells," DNA Repair (Amst.) 12(8):620-636 (2013).
Iyer, L. M., et al., "Prediction of Novel Families of Enzymes Involved in Oxidative and Other Complex Modifications of Bases in Nucleic Acids," Cell Cycle 8(11):1698-1710 (2009).
Jain, A., et al., "CRISPR-Cas9-Based Treatment of Myocilin-Associated Glaucoma," PNAS 114(42):11199-11204 (2017).

(56) References Cited

OTHER PUBLICATIONS

Jiang, W., et al., "RNA-Guided Editing of Bacterial Genomes Using CRISPR-Cas Systems," Nat. Biotechnol. 31(3):233-239 (2013).
Jinek, M., et al., "A Programmable Dual-RNA-Guided DNA Endonuclease in Adaptive Bacterial Immunity," Science 337(6096):816-821 (2012).
Jinek, M., et al., "Structures of Cas9 Endonucleases Reveal RNA-Mediated Conformational Activation," Science 343(6176):1247997 (2014).
Jinek, M., et al., "RNA-Programmed Genome Editing in Human Cells," eLife 2:e00471 (2013).
Joung, J., et al., "Genome-Scale CRISPR-Cas9 Knockout and Transcriptional Activation Screening," Nat. Protoc. 12(4):828-863 (2017).
Kaiser, J., "The Gene Editor CRISPR Won't Fully Fix Sick People Anytime Soon. Here's Why," (May 3, 2016), Biol., Technol, CRISPR, DOI:10.1126/science.aaf5689, 5 pages.
Karolchik, D., et al., "The UCSC Table Browser Data Retrieval Tool," Nucleic Acids Research 32:D493-496 (2004).
Karvelis, T., et al., "crRNA and tracrRNA Guide Cas9-Mediated DNA Interference in *Streptococcus thermophilus*," RNA Biol. 10(5):841-851 (2013).
Kent, W. J., et al., "The Human Genome Browser at UCSC," Genome Research 12:996-1006 (2002).
Keryer-Bibens, C., et al., "Tethering of Proteins to RNAs by Bacteriophage Proteins," Biol. Cell, 100:125-138 (2008).
Khalil, A. S., et al., "Synthetic Biology: Applications Come of Age," Nat. Rev. Genet. 11(5):367-379 (2010).
Kim, H.S., et al., "Problems Encountered in Detecting a Targeted Gene by the Polymerase Chain Reaction," Gene 103:227-233 (1991).
Kim, Y.G., et al., "Hybrid Restriction Enzymes: Zinc Finger Fusions to Fok I Cleavage Domain," Proc. Natl. Acad. Sci. USA 93:1156-1160 (1996).
Kim, B. J., et al., "Gene Therapy for Ocular Diseases," Genetic Diseases of the Eye, 2nd Ed., Editor Elias I. Traboulsi, MD., Published by Oxford Univ. Press, Oxford, England, 20 pages (2012).
Kim, E., et al., "In Vivo Genome Editing with a Small Cas9 Orthologue Derived from Campylobacter Jejuni," Nat. Commun. 8:14500 (2017).
King, N. M.P., et al., "En Route to Ethical Recommendations for Gene Transfer Clinical Trials," Mol. Ther. 16(3):432-438 (2008).
Kleinstiver, B.P., et al., "Broadening the Targeting Range of *Staphylococcus aureus* CRISPR-Cas9 by Modifying PAM Recognition," Nat. Biotechnol. 33(12):1293-1298 (2015).
Kleinstiver, B.P., et al., "Engineered CRISPR-Cas9 Nucleases with Altered PAM Specificities," Nature 523(7561):481-485 (2015).
Kleinstiver, B.P., et al., "High-Fidelity CRISPR-Cas9 Nucleases with No Detectable Genome-Wide Off-Target Effects," Nature 529(7587):490-495 (2016).
Koenekoop, R.K., et al., "Genetic Testing for Retinal Dystrophies and Dysfunctions: Benefits, Dilemmas and Solutions," Clin. Exp. Ophthalmol. 35(5):473-485 (2007).
Koike-Yusa, H., et al., "Genome-Wide Recessive Genetic Screening in Mammalian Cells with a Lentiviral CRISPR-Guide RNA Library," Nat. Biotechnol. 32(3):267-273 (2014).
Komor, A.C., et al., "Programmable Editing of a Target Base in Genomic DNA Without Double-Stranded DNA Cleavage," Nature 533(7603):420-424 (2016).
Kosuri, S., et al., "A Scalable Gene Synthesis Platform Using High-Fidelity DNA Microchips," Nat. Biotechnol. 28(12):1295-1299 (2010).
Lambowitz, A. M., et al., "Group II Introns: Mobile Ribozymes that Invade DNA," Cold Spring Harb. Perspect. Biol. 3:a003616 (2011).
Langmead, B., et al., "Ultrafast and Memory-Efficient Alignment of Short DNA Sequences to the Human Genome," Genome Biology 10(3):R25 (2009).
Leber, T., "On Retinitis Pigmentosa and Congenital Amaurosis," Archiv fur Ophthalmologie 15(3):1-25 (1869).

Lee, J.H., et al., "A Robust Approach to Identifying Tissue-Specific Gene Expression Regulatory Variants Using Personalized Human Induced Pluripotent Stem Cells," PLoS Genetics 5(11):e1000718 (2009).
Lee, J., et al., "Non-Endocytic Delivery of Functional Engineered Nanoparticles into the Cytoplasm of Live Cells Using a Novel, High-Throughput Microfluidic Device," Nano Lett. 12(12):6322-6327 (2012).
Lee, J. K., et al., "Directed evolution of CRISPR-Cas9 to Increase its Specificity," Nat. Commun. 9:3048 (2018).
Li, G.M., "Mechanisms and Functions of DNA Mismatch Repair," Cell Res. 18(1):85-98 (2008).
Li, T., et al., "TAL Nucleases (TALNs): Hybrid Proteins Composed of TAL Effectors and FokI DNA-Cleavage Domain," Nucl. Acids Res.39(1): 359-372 (2011).
Li, H., et al., "In Vivo Genome Editing Restores Hemostasis in a Mouse Model of Hemophilia," Nature 475(7355):217-221 (2011).
Li, T., et al., "Modularly Assembled Designer TAL Effector Nucleases for Targeted Gene Knockout and Gene Replacement in Eukaryotes," Nucl. Acids Res. 39(14):6315-6325 (2011).
Liang, P., et al., "CRISPR/Cas9-Mediated Gene Editing in Human Tripronuclear Zygotes," Protein Cell 6(5):363-372 (2015).
Littink, K.W., et al., "A Novel Nonsense Mutation in CEP290 Induces Exon Skipping and Leads to a Relatively Mild Retinal Phenotype," Invest. Ophthalmol. Vis. Sci. 51 (7):3646-3652 (2010).
Lombardo, A., et al., "Gene Editing in Human Stem Cells Using Xinc Finger Nucleases and Integrase-Defective Lentiviral Vector Delivery," Nat. Biotechnol. 25(11):1298-1306 (2007).
Lorenz, R., et al., "ViennaRNA Package 2.0," Algorithms for Molecular Biology 6:26 (2011).
Maeder, M. L., et al., "CRISPR RNA-Guided Activation of Endogenous Human Genes," Nat. Methods 10:977-979 (2013).
Maeder, M. L., et al., "Rapid "Open-Source" Engineering of Customized Zinc-Finger Nucleases for Highly Efficient Gene Modification," Mol. Cell 31(2):294-301 (2008).
Maeder, M. L., et al., "Therapeutic Correction of an LCA-Causing Splice Defect in the CEP290 Gene by CRISPR/Cas-Mediated Gene Editing," Mol. Ther. 24(Suppl. 1):S51-S52, Abstract 124 (2016).
Maeder, M. L., et al., "Therapeutic Correction of an LCA-Causing Splice Defect in the CEP290 Gene by CRISPR/Cas-Mediated Gene Editing," Presented at the American Society of Gene and cell Therapy Annual Meeting, May 4-7, 2016 in Washington, Dc, XP055418197, retrieved from http://www.editasmedicine.com/data/documents/ASGCT.
Maeder, M. L., et al., "Therapeutic Correction of an LCA-Causing Splice Defect in the CEP290 Gene by CRISPR/Cas-Mediated Genome Editing," Mol. Ther. 23(Suppl. 1):S273-S274 (2015).
Maguire, A.M., et al., "Safety and Efficacy of Gene Transfer for Leber's Congenital Amaurosis," N. Engl. J. Med. 358(21):2240-2248 (2008).
Maguire, A.M., et al., "Age-Dependent Effects of RPE65 Gene Therapy for Leber's Congenital Amaurosis: A Phase 1 Dose-Escalation Trial," Lancet 374(9701):1597-1605 (2009).
Makarova, K. S., et al., "A Putative RNA-lnterference-Based Immune System in Prokaryotes: Computational Analysis of the Predicted Enzymatic Machinery, Functional Analogies with Eukaryotic RNAi, and Hypothetical Mechanisms of Action," Biol. Direct. 1:7 (2006).
Makarova, K. S., et al., "Unification of Cas Protein Families and a Simple Scenario for the Origin and Evolution of CRISPR-Cas Systems," Biol. Direct 6:38 (2011).
Makarova, K.S., et al., "Evolution and Classification of the CRISPR-Cas Systems," Nat. Rev. Microbiol. 9(6):467-477 (2011).
Mali, P., et al., "CAS9 Transcriptional Activators for Target Specificity Screening and Paired Nickases for Cooperative Genome Engineering," Nat. Biotechnol. 31:833-838 (2013).
Mali, P., et al., "Cas9 as a Versatile Tool for Engineering Biology," Nat. Methods 10(10):957-963 (2013).
Mali, P., et al., "RNA-Guided Human Genome Engineering Via Cas9," Science 339(6121):823-826 (2013).
Marteijn, J.A., et al., "Understanding Nucleotide Excision Repairand its Role in Cancer and Ageing," Nat. Rev. Mol. Cell Biol. 15(7):465-481 (2014).

(56) References Cited

OTHER PUBLICATIONS

Mathews, D. H., et al., "Expanded Sequence Dependence of Thermodynamic Parameters Improves Prediction of RNA Secondary Structure," J. Mol. Biol. 288:911-940 (1999).
Miller, J. C., et al., "An Improved Zinc-Finger Nuclease Architecture for Highly Specific Genome Editing," Nat. Biotechnol. 25:778-785 (2007).
Miller, J. C., et al., "A Tale Nuclease Architecture for Efficient Genome Editing," Nat. Biotechnol. 29(2):143-150 (2011).
Miyagishim M., et al., "U6 Promoter-Driven siRNAs with Four Uridine 3' Overhangs Efficiently Suppress Targeted Gene Expression in Mammalian Cells," Nat. Biotechnol. 20(5):497-500 (2002).
Moscou, M. J., et al., "A Simple Cipher Governs DNA Recognition by TAL Effectors," Science 326(5959):1501 (2009).
Myers, E. W., et al., "Optimal Alignments in Linear Space," Comput. Appl. Biosci. 4(1):11-17 (1988).
Nakamura, Y., et al., "Codon Usage Tabulated From International DNA Sequence Databases: Status for the Year 2000," Nucl. Acids Res. 28(1):292 (2000).
Needleman, S. B., et al., "A General Method Applicable to the Search for Similarities in the Amino Acid Sequence of Two Proteins," J. Mol. Biol. 48(3):443-453(1970).
Nishimasu, H., et al., "Crystal Structure of Cas9 in Complex with Guide RNA and Target DNA," Cell 156(5):935-949 (2014).
Nishimasu, H., et al., "Crystal Structure of *Staphylococcus aureus* Cas9," Cell 162:1113-1126 (2015).
Nishimasu, H., et al., "Engineered CRISPR-Cas9 Nuclease with Expanded Targeting Space," Science 361 (6408):1259-1262 (2018).
O'Reily, M., et al., "RNA Interference-Mediated Suppression and Replacement of Human Rhodopsin In Vivo," Am. J. Hum. Genet. 81:127-135 (2007).
Pattanayak, V., et al., "High-Throughput Profiling of Off-Target DNA Cleavage Reveals RNA-Programmed Cas9 Nuclease Specificity," Nat. Biotechnol. 31:839-843 (2013).
Pattanayak, V., et al., "Revealing Off-Target Cleavage Specificities of Zinc-Finger Nucleases by In Vitro Selection," Nat. Methods 8:765-770 (2011).
Patterson, S. S., et al., "Codon Optimization of Bacterial Luciferase (lux) for Expression in Mammalian Cells," J. Ind. Microbio. Biotechnology 32:115-123 (2005).
Pearson, W. R., et al., "Improved Tools for Biological Sequence Comparison," Proc. Natl. Acad. Sci. U.S.A. 85(8):2444-2448 (1988).
Pellissier, L. P., et al., "Specific Tools for Targeting and Expression in Muller Glial Cells," Mol. Then Methods Clin. Dev. 1:14009 (2014).
Peng, R., et al., "Potential Pitfalls of CRISPR/Cas9-Mediated Genome Editing," FEBS J. 283:1218-1231 (2016).
Perez, E. E., et al., "Establishment of HIV-1 Resistance in CD4+ T Cells by Genome Editing Using Zinc-Finger Nucleases," Nat. Biotechnol. 26:808-816 (2008).
Perrault, I., et al., "Spectrum of NPHP6/CEP290 Mutations in Leber Congenital Amaurosis and Delineation of the Associated Phenotype," Hum. Mutat. 28(4):416(2007).
Porteus, M. H., et al., "Gene Targeting Using Zinc Finger Nucleases," Nat. Biotechnol. 23(8):967-973 (2005).
Pougach, K., et al., "Transcription, Processing and Function of CRISPR Cassettes in *Escherichia coli*," Mol. Microbiol. 77(6):1367-1379 (2010).
Pride, D. T., et al., "Analysis of *Streptococcal* CRISPRs from Human Saliva Reveals Substantial Sequence Diversity Within and Between Subjects over Time," Genome Res. 21:126-136 (2011).
Purnick, P. E. M., et al., "The Second Wave of Synthetic Biology: From Modules to Systems," Nat. Rev. Mol. Cell Biol. 10(6):410-422 (2009).
Qi, L. S., et al., "Repurposing CRISPR as an RNA-Guided Platform for Sequence-Specific Control of Gene Expression," Cell 152:1173-1183 (2013).
Qi, L., et al., "RNA Processing Enables Predictable Programming of Gene Expression," Nat. Biotechnol. 30(10): 1002-1007 (2012).

Quinlan, A. R., et al., "BEDTools: A Flexible Suite of Utilities for Comparing Genomic Features," Bioinformatics 26(6):841-842 (2010).
Ran, F.A., et al., "Double Nicking by RNA-Guided CRISPR Cas9 for Enhanced Genome Editing Specificity," Cell 154(6):1380-1389 (2013).
Ran, F. A., et al., "In Vivo Genome Editing Using *Staphylococcus aureus* Cas9," Nature 520(7546):186-191 (2015).
Rand, T. A., et al., "Argonaute2 Cleaves the Anti-Guide Strand of siRNA During RISC Activation," Cell 123:621-629 (2005).
Rao, R. C., et al., "Cell and Gene Therapy," Dev. Ophthalmol. 53:167-177 (2014).
Raymond, C. S., et al., "High-Efficiency FLP and PhiC31 Site-Specific Recombination in Mammalian Cells," PLoS One2(1):e162 (2007).
Rebar, E. J., et al., "Zinc Finger Phage: Affinity Selection of Fingers with New DNA-Binding Specificities," Science 263(5147):671-673 (1994).
Rebar, E. J., et al., "Induction of Angiogenesis in a Mouse Model Using Engineered Transcription Factors," Nat. Med. 8(12):1427-1432 (2008).
Recht, M. I., et al., "Monitoring Assembly of Ribonucleoprotein Complexes by Isothermal Titration Calorimetry," Methods in Mol. Biol. 488:117-127 (2008).
Regalado, A., "Who Owns the Biggest Biotech Discovery of the Century?," MIT Technology Review, Dec. 4, 2014, http://www.technologyreview.com/featuredstory/532796/who-owns-the-biggest--biotech-discovery-of-the-century/.
Reyon, D., et al., "FLASH Assembly of TALENs for High-Throughput Genome Editing," Nat. Biotech. 30:460-465 (2012).
Rho, M., et al. "Diverse CRISPRs Evolving in Human Microbiomes." PLoS Genetics 8(6):e1002441 (2012).
Richardson, C. D., et al., "Enhancing Homology-Directed Genome Editing by Catalytically Active and Inactive CRISPR-Cas9 Using Asymmetric Donor DNA," Nat. Biotechnol. 34(3):339-344 (2016).
Ruan, G.X., et al., "CRISPR/Cas9-Mediated Genome Editing as a Therapeutic Approach for Leber Congenital Amaurosis 10," Mol. Ther. 25(2):331-341 (2017).
Sander, J. D., et al., "Zinc Finger Targeter (ZiFiT): An Engineered Zinc Finger/Target Site Design Tool," Nucleic Acids Res. 35:W599-W605 (2007).
Sander, J. D., et al., "ZiFiT (Zinc Finger Targeter): An Updated Zinc Finger Engineering Tool," Nucleic Acids Res. 38:W462-468 (2010).
Sander, J. D., et al., "CRISPR-Cas Systems for Editing, Regulating and Targeting Genomes," Nat. Biotechnol. 32(4):347-355 (2014).
Sanders, R., "Cheap and Easy Technique to Snip DNA Could Revolutionize Gene Therapy", Berkeley News Online, pp. 1-3 (Jan. 7, 2013).
Sanjana, N. E., et al., "A Transcription Activator-Like Effector (TALE) Toolbox for Genome Engineering," Nat. Protoc. 7(1):171-192 (2012).
Sapranauskas, R., et al., "The *Streptococcus thermophilus* CRISPR-Cas System Provides Immunity in *Escherichia coli*," Nucl. Acids Res.39:9275-9282 (2011).
Sather, B. D., et al., "Efficient Modification of CCR5 in Primary Human Hematopoietic Cells Using a Mega TAL Nuclease and AAV Donor Template," Sci. Trans. Med. 7(307):307ra156 (2015).
Schramm, L., et al., "Recruitment of RNA Polymerase III to its Target Promoters," Genes Devel. 16:2593-2620 (2002).
Selleck, W., et al., "Biophysical Characterization and Direct Delivery of S. Pyogenes Cas9 Ribonucleoprotein Complexes," Editas Medicine, Apr. 27, 2015, retrieved from URL http://www.editasmedicine.com/documents/ASGCT_poster_2015_Will.pdf.
Shalem, O., et al., "Genome-Scale CRISPR-Cas9 Knockout Screening in Human Cells," Science 343:84 (2014).
Shanks, P., "CRISPR Opportunities . . . for What? And for Whom?," Biopolitical Times, Dec. 4, 2014, http://www.biopoliticaltimes.org/article.php?id=8235.
Sharma, R., et al., "In Vivo Genome Editing of the Albumin Locus as a Platform for Protein Replacement Therapy," Blood 126(15):1777-1784 (2015).

(56) References Cited

OTHER PUBLICATIONS

Shayakhmetov, D. M., et al., "Analysis of Adenovirus Sequestration in the Liver, Transduction of Hepatic Cells, and Innate Toxicity after Injection of Fiber-Modified Vectors," J. Virol. 78(10):5368-5381 (2004).
Shen, B., et al., "Generation of Gene-Modified Mice via Cas9/RNA-Mediated Gene Targeting," Cell Res. 23:720-723 (2013).
Shmakov, S., et al., "Discovery and Functional Characterization of Diverse Class 2 CRISPR-Cas Systems," Mol. Cell 60(3):385-397 (2015).
Singh, M., et al., "Genes and Genetics in Eye Diseases: A Genomic Medicine Approach for Investigating Hereditary and Inflammatory Ocular Disorders," Int. J. Ophthalmol. 11(1):117-134 (2018).
Smith, C., et al., "Efficient and Allele-Specific Genome Editing of Disease Loci in Human iPSCs," Mol. Ther. 23(3):570-577 (2015).
Smith, T. F., et al., "Comparison of Biosequences," Adv. Appl. Math. 2(4):482-489 (1981).
Sontheimer, E., "Project?: Establishing RNA-Directed DNATargeting in Eukaryotic Cells; Project dates: Nov. 16, 2011 to Dec. 31, 2012," Physical Sciences—Oncology Center (Feb. 4, 2012).
Sternberg, S.H., et al., "DNA Interrogation by the CRISPR RNA-Guided Endonuclease Cas9," Nature 507(7490):62-67 (2014).
Stone, E.M., "Leber Congenital Amaurosis—A Model for Efficient Genetic Testing of Heterogeneous Disorders: LXIV Edward Jackson Memorial Lecture," Am. J. Ophthalmol. 144(6):791-811 (2007).
Stone, E.M., et al., "Clinically Focused Molecular Investigation of 1000 Consecutive Families with Inherited Retinal Disease," Opthalmol. 124(9):1314-1331 (2017).
Strecker, J., et al., "Engineering of CRISPR-Cas12b for Human Genome Editing," Nat. Commun. 10:212 (2019).
Sugimoto, N., et al., "Thermodynamic Parameters to Predict Stability of RNA/DNA Hybrid Duplexes," Biochem. 34:11211-11216 (1995).
Sugimoto, N., et al., "Thermodynamics-Structure Relationship of Single Mismatches in RNA/DNA Duplexes," Biochem. 39(37):11270-11281 (2000).
Szczepek, M., et al., "Structure-Based Redesign of the Dimerization Interface Reduces the Toxicity of Zinc-Finger Nucleases," Nat. Biotechnol. 25:786-793 (2007).
Tang, L., et al., "CRISPR/Cas9-Mediated Gene Editing in Human Zygotes Using Cas9 Protein," Mol. Genet. Genom. 292(3):525-533 (2017).
Teng, F., et al., "Repurposing CRISPR-Cas12b for Mammalian Genome Engineering," Cell Discov. 4:63 (2018).
Terns, M. P., et al., "CRISPR-based Adaptive Immune Systems," Curr. Opin. Microbiol. 14:321-327 (2011).
Thurman, R. E., et al., "The Accessible Chromatin Landscape of the Human Genome," Nature 489(7414):75-82 (2012).
Tolia, N. H., et al., "Slicerand the Argonautes," Nat. Chem. Biol. 3(1):36-43 (2007).
Tolpin, Thomas W., Third Party Observation for EP13793997.1, Jan. 6, 2015, 50 pages.
Truong, L. N., et al., "Microhomology-Mediated End Joining and Homologous Recombination Share the Initial End Resection Step to Repair DNA Double-Strand Breaks in Mammalian Cells," PNAS 110(19):7720-7725 (2013).
Tsai, S. Q., et al., "Dimeric CRISPR RNA-Guided FokI Nucleases for Highly Specific Genome Editing," Nat. Biotechnol. 32(6):569-576 (2014).
Tsai, S.Q., et al., "Open-Source GuideSeq Software for Analysis of GUIDE-Seq Data," Nat. Biotechnol. 34(5):483 (2016).
Urnov, F. D., et al., "Highly Efficient Endogenous Human Gene Correction Using Designed Zinc-Finger Nucleases," Nature 435:646-651 (2005).
Valente, E.M., et al., "Mutations of CEP290, Which Encodes a Centrosomal Protein, Cause Pleiotropic Forms of Joubert Syndrome," Nat. Genet. 38(6):623-625 (2006).
Van Der Oost, J., "New Tool for Genome Surgery," Science 336:768-768 (2013).
Van Der Ploeg, J. R., "Analysis of CRISPR in *Streptococcus* Mutans Suggests Frequent Occurrence of Acquired Immunity Against Infection by M102-Like Bacteriophages," Microbiology 155:1966-1976 (2009).
Van Overbeek, M., et al., "DNA Repair Profiling Reveals Nonrandom Outcomes at Cas9-Mediated Breaks," Mol. Cell 63:633-646 (2016).
Wang, H., et al., "One-Step Generation of Mice Carrying Mutations in Multiple Genes by CRISPR/Cas-Mediated Genome Engineering," Cell 153(4):910-918 (2013).
Wang, J., et al., "Homology-Driven Genome Editing in Hematopoietic Stem and Progenitor Cells Using ZFN mRNA and AAV6 Donors," Nat. Biotechnol. 33(12):1256-1263 (2015).
Wang, J., et al., "Highly Efficient Homology-Driven Genome Editing in Human T Cells by Combining Zinc-Finger Nuclease mRNA and AAV6 Donor Delivery," Nucleic Acids Res. 44(3):e30 (2016).
Wang, T., et al., "Genetic Screens in Human Cells Using the CRISPR-Cas9 System," Science 343(6166):80-84 (2013).
Wang, J., et al., "xCas9 Expands the Scope of Genome Editing with Reduced Efficiency in Rice," Plant Biotechnol. J. 17:709-711 (2019).
Wiedenheft, B., et al., "RNA-Guided Genetic Silencing Systems in Bacteria and Archaea," Nature 482:331-338 (2012).
Wu, X., et al., "Genome-Wide Binding of the CRISPR Endonuclease Cas9 in Mammalian Cells," Nat. Biotechnol. 32(7):670-676 (2014).
Wu, Y., et al., "Correction of a Genetic Disease in Mouse via Use of CRISPR-Cas9," Cell Stem Cell 13(6):659-662 (2013).
Xiao, A., et al., "CasOT: A Genome-Wide Cas9/gRNA Off-Target Searching Tool," Bioinformatics 30(8):1180-1182 (2014).
Xu, Q., et al., "Design of 240,000 Orthogonal 25mer DNA Barcode Probes," Proc. Natl. Acad. Sci.106(7):2289-2294 (2009).
Yamano, T., et al., "Crystal Structure of Cpf1 in Complex with Guide RNA and Target DNA," Cell 165(4):949-962 (2016).
Yan, W. X., et al., "Functionally Diversse Type V CRISPR-Cas Systems," Science 363:88-91 (2019).
Yang, H., et al., "One-Step Generation of Mice Carrying Reporter and Conditional Alleles by CRISPR/Cas-Mediated Genome Engineering," Cell 154(6):1370-1390 (2013).
Zetsche, B., et al., "A Split-Cas9 Architecture for Inducible Genome Editing and Transcription Modulation," Nat. Biotechnol. 33(2):139-142 (2015).
Zetsche, B., et al., "Cpf1 Is a Single RNA-Guided Endonuclease of a Class 2 CRISPR-Cas System," Cell 163(3):759-771 (2015).
Zheng, A., et al., "Personalized Therapeutic Strategies for Patients with Retinitis Pigmentosa," Expert Opin. Biol. Ther. 15(3):391-402 (2015).
Zou, J., et al., "Gene Targeting of a Disease-Related Gene in Human Induced Pluripotent Stem and Embryonic Stem Cells," Cell Stem Cell 5(1):97-110 (2009).
7th Annual 2014 Midwest Eye Research Symposium Program, Aug. 8, 2014, retrieved from: http://webeye.ophth.uiowa.edU/eig/MERS_2014.html#Back.
European Patent Office, International Search Report and Written Opinion dated Jun. 24, 2015 for PCT/US2015/019064.
European Patent Office, International Search Report and Written Opinion dated Jul. 1, 2015 for PCT/US2015/019790.
European Patent Office, International Search Report and Written Opinion dated Sep. 28, 2015 for PCT/US2015/022856.
European Patent Office, International Search Report and Written Opinion dated Jul. 31, 2015 for PCT/US2015/022851.
European Patent Office, International Search Report and Written Opinion dated Aug. 10, 2015 for PCT/US2015/023906.
European Patent Office, International Search Report and Written Opinion dated Jun. 12, 2017 for PCT/US2017/024163.
European Patent Office, International Search Report and Written Opinion dated Jul. 28, 2016 for PCT/US2016/029252.
European Patent Office, International Search Report and Written Opinion dated May 29, 2017 for PCT/US2017/022377.
European Patent Office, International Search Report and Written Opinion dated Oct. 26, 2017 for PCT/US2017/045191.
Guo, Q., et al., "'Cold shock' increases the frequency of homology directed repair gene editing in induced pluripotent stem cells," Sci. Rep. 8(1):2080 (2018).

(56) References Cited

OTHER PUBLICATIONS

Maeder, M. L., et al., "Development of a gene-editing approach to restore vision loss in Leber congenital amaurosis type 10," Nat. Med. 25(2):229-233 (2019).
Paix, A., et al., "Precision Genome Editing Using CRISPR-Cas9 and Linear Repair Templates in C. Elegans," Methods 121-121:86-93 (2017).
Weleber, R. G., et al. "Leber Congenital Amaurosis." GeneReviews® [Internet]., U.S. National Library of Medicine, May 2, 2013, https://www.ncbi.nlm.nih.gov/books/NBK1298/. 32 pages.
European Patent Office, International Search Report and Written Opinion dated Dec. 12, 2019 for PCT/US2019/040641.
United States Patent and Trademark Office, International Search Report and Written Opinion for PCT/US2013/075317, dated Apr. 15, 2014, 12 pages.
United States Patent and Trademark Office, International Search Report and Written Opinion for PCT/US2013/075326, dated Aug. 22, 2014, 13 pages.
United States Patent and Trademark Office, International Search Report and Written Opinion for PCT/US2014/027335, dated Jul. 16, 2014, 13 pages.
United States Patent and Trademark Office, International Search Report and Written Opinion for PCT/US2014/028630, dated Jul. 24, 2014, 9 pages.
Ding, Q., et al., "Enhanced Efficiency of Human Pluripotent Stem Cell Genme Editing through Replacing TALENs with CRIPSRs," Cell Stem Cell 12:393-394 (2013).
Heintze, J., et al., "A Crispr CASe for High-Throughput Silencing," Front. Genet. 4(193):1-6 (2013).
Mukherjee-Clavin, B., et al., "Current Approaches for Efficient Genetic Editing in Human Pluripotent Stem Cells," Front. Biol. 8(5):461-467 (2013).
Bothmer, A., et al., "Detection and Modulation of DNA Translocations During Multi-Gene Genome Editing in T Cells," The CRISPR Journal 3(3):177-187 (2020).
Burnight, E. R., et al., "Using CRIPSR-Cas9 to Generate Gene-Corrected Autologous iPSCs for the Treatment of Inherited Retinal Degeneration," Mol. Ther. 25(9):1999-2013 (2017).
Cost, G. J., et al., Geneseq Accession No. BBD49192 (2014), 2 pages.
Fu, B. X. H., et al., "Landscape of Target: Guide Homology Effects on Cas9-Mediated Cleavage," Nucl. Acids Res. 42(22):13778-13787 (2014).
Giannoukos, G., et al., "UDiTaS™, a genome editing detection method for indels and genome rearrangements," BMC Genomics 19:212 (2018).
Kleinstiver, B. P., et al., "Engineered CRISPR-Cas12a variants with increased activities and improved targeting ranges for gene, epigenetic and base editing," Nat. Biotechnol. 37(3):276-282 (2019).
Kosicki, M., et al., "Repair of Double-Strand Breaks Induced by CRISPR-Cas9 Leads to Large Deletions and Complex Rearrangements," Nat. Biotechnol. 36(8):765-771 (2018).
Krieg, A. M., et al., GeneSeq Accession No. BAY71542 (2013).
Lee, J. H., et al., "Gene Therapy for Visual Loss: Opportunities and Concerns," Progress in Retinal and Eye Research 68:31-53 (2019).
Pausch, P., et al., "CRISPR-CasФ from Huge Phages is a Hypercompact Genome Editor," Science ;369(6501):333-337 (2020).
Reeks, J., et al., "Structure of a Dimeric Crenarchaeal Cas6 Enzyme with an Atypical Active Site for CRISPR RNA Processing," Biochem. J. 452:223-230 (2013).

Reichel, F. F., et al., "AAV8 Can Induce Innate and Adaptive Immune Response in the Primate Eye," Mol. Ther. 25(12):2648-1660 (2017).
Strohkendl, I., et al., "Kinetic Basis for DNA Target Specificity of CRISPR-Cas12a,"Mol Cell. 71(5):816-824 (2018).
Swarts, D. C., et al., "Cas9 Versus Cas12a/Cpf1: Structure-Function Comparisons and Implications for Genome Editing," WIREs RNA 9:e1481 (2018).
Vidigal, J. A, et al.,"Rapid and Efficient One-Step Generation of Paired gRNA CRISPR-Cas9 Libraries," Nat. Commun. 6:8083 (2015).
Weber, L., et al., "Editing a y-Globin Repressor Binding Site Restores Fetal Hemoglobin Synthesis and Corrects the Sickle Cell Disease Phenotype," Sci. Adv. 6:eaay9392 (2020).
Wu, W., et al., "Application of CRISPR-Cas9 in Eye Disease," Exp. Eye Res. 161:116-123 (2017).
European Patent Office, International Search Report and Written Opinion dated Jun. 17, 2020 for PCT/US2020/019766, 18 pages.
Cramer, M. L., et al., "Induction of T-Cell Infiltration and Programmed Death Ligand 2 Expression by Adeno-Associated Virus in Rhesus Macaque Skeletal Muscle and Modulation by Prednisone," Hum. Gene Ther. 28(6):493-509 (2017).
Kumar, S. R.P., et al., "Clinical development of gene therapy: results and Tessons from recent successes," Mol. Ther. Methods Clin. Dev. 3:16034 (2016).
Li, W., et al., "Gene Therapy Following Subretinal AAV5 Vector Delivery is Not Affected By a Previous Intravitreal AAV5 Vector Administration in the Partner Eye," Mol. Vision 15:267-275 (2009).
Lopes, V. S., et al., "Retinal Gene Therapy with a Large MYO7A cDNA Using Adeno-Associated Virus," Gene Ther. 20(8):824-833 (2013).
Sobrevals, L., et al., "AAV Vectors Transduce Hepatocytes In Vivo as Efficiently in Cirrhotic as in Healthy Rat Livers," Gene Ther. 19:411-417 (2012).
Vandenberghe, L. H., et al., "Dosage Thresholds for AAV2 and AAV8 Photoreceptor Gene Therapy in Monkey," Sci. Transl. Med. 3(88):88ra54 (2011).
Xue, K., et al., "Technique of Retinal Gene Therapy: Delivery of Viral Vector Into the Subretinal Space," Eye 31 (9):1308-1316 (2017).
Zetsche, B., et al., "Multiplex Gene Editing by CRISPR-Cpf1 Through Autonomous Processing of a Single crRNA Array," Nat. Biotechnol. 35(1):31-34 (2017).
Jeon, C.J., et al., "The Major Cell Populations of the Mouse Retina," J. Neurosci. 18(21):8936-8946 (1998).
Kim, D., et al., "Genome-wide analysis reveals specificities of Cpf1 endonucleases in human cells," Nat. Biotechnol. 34(8):863-868 (2016).
Kleinstiver, B.P., et al., "Genome-Wide Specificities of CRISPR-Cas Cpf1 Nucleases in Human Cells," Nat. Biotechnol. 34(8):869-874 (2016).
Packer, O., et al., "Photoreceptor Topography of the Retina in the Adult Pigtail Macaque (*Macaca nemestrina*)," J. Comp. Neurol. 288(1):165-183 (1989).
Sakuma, T., et al., "Multiplex Genome Engineering in Human Cells Using All-in-One CRISPR/Cas9 Vector System," Sci. Rep. 4(5400):1-6 (2014).
Wikler, K. C., et al., "Photoreceptor Mosaic: Number and Distribution of Rods and Cones in the Rhesus Monkey Retina," J. Comp. Neurol. 297(4):499-508 (1990).

\* cited by examiner

```
NNNNNNNNNNNNNNNNNNNNNGUUUUAGUA C UCUGG
                     ||||||||| |||| A
                                    A
        ACGGAACAAAAUCAUCUAAGACA
   A A  ||||
    A
        UGCCGUGUUUAUCUCGUCAAC
        |||||| |||| U
                     U
        UUUUUUAGAGCGGUUG
```

*S. aureus* gRNA

FIG. 3

COMPOSITIONS AND METHODS FOR TREATING CEP290 ASSOCIATED DISEASE

CROSS REFERENCE TO RELATED APPLICATIONS

The present application claims the benefit of U.S. Provisional Appl. No. 62/370,202, filed Aug. 2, 2016; U.S. Provisional Appl. No. 62/400,526, filed Sep. 27, 2016; U.S. Provisional Appl. No. 62/443,568, filed Jan. 6, 2017; U.S. Provisional Appl. No. 62/503,800, filed May 9, 2017; and U.S. Provisional Appl. No. 62/535,193, filed Jul. 20, 2017; the contents of which are hereby incorporated by reference in their entirety.

SEQUENCE LISTING

This disclosure includes a sequence listing, which was submitted in ASCII format via EFS-Web, and is hereby incorporated by reference in its entirety. The ASCII copy, created on Aug. 2, 2017, is named SequenceListing.txt and is 47.4 kilobytes in size.

FIELD

The disclosure relates to CRISPR/CAS-related methods and components for editing of a target nucleic acid sequence, and applications thereof in connection with CEP290 associated disease.

BACKGROUND

CEP290 is a 290 kilodalton (kDa) protein encoded by a 90 kilobase-pair (kb) gene, which is thought to be involved in the normal function of the eye and kidney. In cells, the CEP290 protein associates with the centrosome and with cellular scaffold proteins, and is implicated in a variety of cellular processes including cell division, the DNA damage response, and ciliogenesis. Mutations of CEP290 are observed in several diseases, including Senior-Loken syndrome, Meckel Gruber syndrome, Bardet-Biedle syndrome, Joubert Syndrome, and Leber Congenital Amaurosis 10 (LCA10).

LCA10 is an inherited retinal degenerative disease characterized by severe visual impairment or blindness at birth. The disease is inherited in an autosomal recessive fashion and is caused by a C.2991+1655A to G mutation (the "IVS26" mutation) in the CEP290 gene. IVS26 is a loss-of-function mutation in which a cryptic splice donor site is formed in intron 26 of the CEP290 gene, resulting in prematurely truncated CEP290 mRNA transcripts that include an aberrant 128 bp exon. The consequent loss of CEP290 function is thought to disrupt sensory cilia function in photoreceptor cells, leading to the disease.

There are currently no approved therapies for LCA10. Gene therapy strategies for treating CEP290 associated disease are complicated by the size of the protein and the difficulty of packaging large sequences into currently used gene therapy vectors, and no small molecule therapies have been approved for the disease. To address the lack of treatment options for LCA10, the inventors have developed a strategy for correcting the IVS26 mutation in cells using CRISPR/Cas9 genome editing, and have shown deletion of the mutation in up to 60% of HEK293 cells in vitro. See International Patent Publication No. WO2015/138510 by Maeder et al. ("Maeder"), which is incorporated by reference herein.

SUMMARY

The inventors have addressed a key unmet need in the field by providing new and effective means of delivering genome editing systems to the affected tissues of subjects suffering from CEP290 associated diseases and other inherited retinal dystrophies. This disclosure provides nucleic acids and vectors for efficient transduction of genome editing systems in retinal cells and cells in other tissues, as well as methods of using these vectors to treat subjects. These nucleic acids, vectors and methods represent an important step forward in the development of treatments for CEP290 associated diseases.

In one aspect, the disclosure relates to a method for treating or altering a cell in a subject (e.g., a human subject or an animal subject) that includes administering to the subject a nucleic acid encoding a Cas9 and first and second guide RNAs (gRNAs) targeted to the CEP290 gene of the subject. In certain embodiments, the first and second gRNAs are targeted to one or more target sequences that encompass or are proximal to a CEP290 target position. The first gRNA may include a targeting domain selected from SEQ ID NOS: 1-3 (corresponding RNA sequences in SEQ ID NOS: 26-28, respectively), while the targeting domain of the second gRNA may be selected from SEQ ID NOS: 4-6 (corresponding RNA sequences in SEQ ID NOS: 29-31, respectively). The Cas9, which may be a modified Cas9 (e.g., a Cas9 engineered to alter PAM specificity, improve fidelity, or to alter or improve another structural or functional aspect of the Cas9), may include one or more of a nuclear localization signal (NLS) and/or a polyadenylation signal. Certain embodiments are characterized by Cas9s that include both a C-terminal and an N-terminal NLS. The Cas9 is encoded, in certain embodiments, by SEQ ID NO: 10, and its expression is optionally driven by one of a CMV, EFS, or hGRK1 promoter, as set out in SEQ ID NOS: 13-15 respectively. The nucleic acid also includes, in various cases, first and second inverted terminal repeat sequences (ITRs).

Continuing with this aspect of the disclosure, a nucleic acid comprising any or all of the features described above may be administered to the subject via an adeno-associated viral (AAV) vector, such as an AAV5 vector. The vector may be delivered to the retina of the subject (for example, by subretinal injection). Various embodiments of the method may be used in the treatment of human subjects. For example, the methods may be used to treat subjects suffering from a CEP290 associated disease such as LCA10, to restore CEP290 function in a subject in need thereof, and/or to alter a cell in the subject, such as a retinal cell and/or a photoreceptor cell.

In another aspect, this disclosure relates to a nucleic acid encoding a Cas9, a first gRNA with a targeting domain selected from SEQ ID NOS: 1-3 (corresponding RNA sequences in SEQ ID NOS: 26-28, respectively), and a second gRNA with a targeting domain selected from SEQ ID NOS: 4-6 (corresponding RNA sequences in SEQ ID NOS: 29-31, respectively). The nucleic acid may, in various embodiments, incorporate any or all of the features described above (e.g., the NLS and/or polyadenylation signal; the CMV, EFS or hGRK1 promoter; and/or the ITRs). The nucleic acid may be part of an AAV vector, which vector may be used in medicine, for example to treat a CEP290 associated disease such as LCA10, and/or may be used to edit specific cells including retinal cells, for instance retinal photoreceptor cells. The nucleic acid may also be used for the production of a medicament.

In yet another aspect, this disclosure relates to a method of treating a subject that includes the step of contacting a retina of the subject with one or more recombinant viral vectors (e.g., AAV vectors) that encode a Cas9 and first and second gRNAs. The first and second gRNAs are adapted to form first and second ribonucleoprotein complexes with the Cas9, and the first and second complexes in turn are adapted to cleave first and second target sequences, respectively, on either side of a CEP290 target position as that term is defined below. This cleavage results in the alteration of the nucleic acid sequence of the CEP290 target position. In some embodiments, the step of contacting the retina with one or more recombinant viral vectors includes administering to the retina of the subject, by subretinal injection, a composition comprising the one or more recombinant viral vectors. The alteration of the nucleic acid sequence of the CEP290 target position can include formation of an indel, deletion of part or all of the CEP290 target position, and/or inversion of a nucleotide sequence in the CEP290 target position. The subject, in certain embodiments, is a primate.

The genome editing systems, compositions, and methods of the present disclosure can support high levels of productive editing in retinal cells, e.g., in photoreceptor cells. In certain embodiments, 10%, 15%, 20%, or 25% of retinal cells in samples modified according to the methods of this disclosure (e.g., in retinal samples contacted with a genome editing system of this disclosure) comprise a productive alteration of an allele of the CEP290 gene. A productive alteration may include, variously, a deletion and/or inversion of a sequence comprising an IVS26 mutation, or another modification that results in an increase in the expression of functional CEP290 protein in a cell. In certain embodiments, 25%, 30%, 35%, 40%, 45%, 50%, or more than 50% of photoreceptor cells in retinal samples modified according to the methods of this disclosure (e.g., in retinal samples contacted with a genome editing system of this disclosure) comprise a productive alteration of an allele of the CEP290 gene.

In another aspect, this disclosure relates to a nucleic acid encoding a Cas9 and first and second gRNAs targeted to a CEP290 gene of a subject for use in therapy, e.g. in the treatment of CEP290-associated disease. The CEP290 associated disease may be, in some embodiments, LCA10, and in other embodiments may be selected from the group consisting of Senior-Loken syndrome, Meckel Gruber syndrome, Bardet-Biedle syndrome and Joubert Syndrome. Targeting domains of the first and second gRNAs may comprise the sequences of SEQ ID NOS: 1-3 and NOS: 4-6, respectively, and in certain embodiments the first and second gRNA targeting domains comprise: SEQ ID NOS: 1 and 4. In other embodiments, the first and second gRNA targeting domains comprise the sequences of SEQ ID NOS: 1 and 5, SEQ ID NOS: 1 and 6, SEQ ID NOS: 2 and 4, SEQ ID NOS 3 and 4, or SEQ ID NOS: 3 and 5. In still other embodiments, the first and second targeting domains comprise the sequences of SEQ ID NOS: 2 and 5, SEQ ID NOS: 2 and 6, or SEQ ID NOS: 3 and 6. The gRNAs according to this aspect of the disclosure may be unimolecular, and may comprise RNA sequences according to SEQ ID NO: 7 or SEQ ID NO: 8. Alternatively, the gRNAs may be two-part modular gRNAs according to either sequence, where the crRNA component comprises the portion of SEQ ID NO: 7 or 8 that is underlined, and the tracrRNA component comprises the portion that is double-underlined.

Continuing with this aspect of the disclosure, the Cas9 encoded by the nucleic acid is, in certain embodiments, a *Staphylococcus aureus* Cas9, which may be encoded by a sequence comprising SEQ ID NO: 10, or having at least 80%, 85%, 90%, 95% or 99% sequence identity thereto. The Cas9 encoded by the nucleic acid may comprise the amino acid sequence of SEQ ID NO: 11 or may share at least 80%, 85%, 90%, 95% or 99% sequence identity therewith. The Cas9 may be modified in some instances, for example to include one or more nuclear localization signals (NLSs) (e.g., a C-terminal and an N-terminal NLS) and/or a polyadenylation signal. Cas9 expression may be driven by a promoter sequence such as the promoter sequence comprising SEQ ID NO: 13, the promoter sequence comprising SEQ ID NO: 14, or the promoter sequence comprising SEQ ID NO: 15.

Staying with this aspect of the disclosure, the promoter sequence for driving the expression of the Cas9 comprises, in certain embodiments, the sequence of a human GRK1 promoter. In other embodiments, the promoter comprises the sequence of a cytomegalovirus (CMV) promoter or an EFS promoter. For example, the nucleic acid may comprise, in various embodiments, a) a CMV promoter for Cas9 and gRNAs comprising (or differing by no more than 3 nucleotides from) targeting domains according to SEQ ID NOs: 1 and 5, or b) a CMV promoter for Cas9 and gRNAs comprising targeting domains according to SEQ ID NOs: 1 and 6, or c) a CMV promoter for Cas9 and gRNAs comprising targeting domains according to SEQ ID NOs: 2 and 4, or d) a CMV promoter for Cas9 and gRNAs comprising targeting domains according to SEQ ID NOs: 3 and 4, or e) a CMV promoter for Cas9 and gRNAs comprising targeting domains according to SEQ ID NOs: 3 and 5, or f) an EFS promoter for Cas9 and gRNAs comprising targeting domains according to SEQ ID NOs: 1 and 5, or g) an EFS promoter for Cas9 and gRNAs comprising targeting domains according to SEQ ID NOs: 1 and 6, or h) an EFS promoter for Cas9 and gRNAs comprising targeting domains according to SEQ ID NOs: 2 and 4, or i) an EFS promoter for Cas9 and gRNAs comprising targeting domains according to SEQ ID NOs: 3 and 4, or j) an EFS promoter for Cas9 and gRNAs comprising targeting domains according to SEQ ID NOs: 3 and 5, or k) an hGRK1 promoter for Cas9 and gRNAs comprising targeting domains according to SEQ ID NOs: 1 and 5, or g) an hGRK1promoter for Cas9 and gRNAs comprising targeting domains according to SEQ ID NOs: 1 and 6, or h) an hGRK1promoter for Cas9 and gRNAs comprising targeting domains according to SEQ ID NOs: 2 and 4, or i) an hGRK1 promoter for Cas9 and gRNAs comprising targeting domains according to SEQ ID NOs: 3 and 4, or j) an hGRK1 promoter for Cas9 and gRNAs comprising targeting domains according to SEQ ID NOs: 3 and 5. In other embodiments, the nucleic acid comprises a CMV promoter and guide RNA targeting sequences according to SEQ ID NOS: 1 and 4. In still other embodiments, the nucleic acid comprises an hGRK promoter and guide RNA targeting sequences according to SEQ ID NOS: 2 and 5, or it comprises a CMV promoter and guide RNA targeting sequences according to SEQ ID NOS: 2 and 5, or an hGRK promoter and guide RNA targeting sequences according to SEQ ID NOS: 2 and 6, or it comprises a CMV promoter and guide RNA targeting sequences according to SEQ ID NOS: 3 and 6, or an hGRK promoter and guide RNA targeting sequences according to SEQ ID NOS: 3 and 6, or it comprises a CMV promoter and guide RNA targeting sequences according to SEQ ID NOS: 2 and 5. And in further embodiments, the promoter is hGRK or CMV while the first and second gRNA targeting domains comprise the sequences of SEQ ID NOS: 1 and 5, SEQ ID NOS: 1 and 6, SEQ ID NOS: 2 and 4, SEQ ID NOS 3 and 4, or SEQ ID NOS: 3 and 5.

In another aspect, the present disclosure relates to adeno-associated virus (AAV) vectors comprising the nucleic acids described above. AAV vectors comprising the foregoing nucleic acids may be administered to a variety of tissues of a subject, though in certain embodiments the AAV vectors are administered to a retina of the subject, and/or are administered by subretinal injection. The AAV vector may comprise an AAV5 capsid.

An additional aspect of this disclosure relates to a nucleic acid as described above, for delivery via an AAV vector also as described above. The nucleic acid includes in some embodiments, first and second inverted terminal repeat sequences (ITRs), a first guide RNA comprising a targeting domain sequence selected from SEQ ID NOS: 1-3, a second guide RNA comprising a targeting domain sequence selected from SEQ ID NOS: 4-6, and a promoter for driving Cas9 expression comprising a sequence selected from SEQ ID NOS: 13-15. In certain embodiments, the nucleic acid includes first and second ITRs and first and second guide RNAs comprising a guide RNA sequence selected from SEQ ID NOS: 7 and 8 (e.g., both first and second guide RNAs comprise the sequence of SEQ ID NO: 8). The nucleic acid may be used in the treatment of human subjects, and/or in the production of a medicament.

The nucleic acids and vectors according to these aspects of the disclosure may be used in medicine, for instance in the treatment of disease. In some embodiments, they are used in the treatment of a CEP290-associated disease, in the treatment of LCA10, or in the treatment of one or more of the following: Senior-Loken syndrome, Meckel Gruber syndrome, Bardet-Biedle syndrome, and/or Joubert Syndrome. Vectors and nucleic acids according to this disclosure may be administered to the retina of a subject, for instance by subretinal injection.

This disclosure also relates to recombinant viral vectors comprising the nucleic acids described above, and to the use of such viral vectors in the treatment of disease. In some embodiments, one or more viral vectors encodes a Cas9, a first gRNA and a second gRNA for use in a method of altering a nucleotide sequence of a CEP 290 target position wherein (a) the first and second gRNAs are adapted to form first and second ribonucleoprotein complexes with the Cas9, and (b) the first and second ribonucleoprotein complexes are adapted to cleave first and second cellular nucleic acid sequences on first and second sides of a CEP290 target position, thereby altering a nucleotide sequence of the CEP290 target position. In use, the one or more recombinant viral vectors is contacted to the retina of a subject, for instance by subretinal injection.

Another aspect of this disclosure relates to AAV vectors, AAV vector genomes and/or nucleic acids that may be carried by AAV vectors, which encode one or more guide RNAs, each comprising a sequence selected from—or having at least 90% sequence identity to—one of SEQ ID NOS: 7 or 8 (corresponding RNA sequences in SEQ ID NOS: 32 and 33, respectively), a sequence encoding a Cas9 and a promoter sequence operably coupled to the Cas9 coding sequence, which promoter sequence comprises a sequence selected from—or having at least 90% sequence identity to—one of SEQ ID NOS: 13-15. The Cas9 coding sequence may comprise the sequence of SEQ ID NO: 10, or it may share at least 90% sequence identity therewith. Alternatively or additionally, the Cas9 coding sequence may encode an amino acid sequence comprising SEQ ID NO: 11, or sharing at least 90% sequence identity therewith. In certain embodiments, the AAV vector, vector genome or nucleic acid further comprises one or more of the following: left and right ITR sequences, optionally selected from—or having at least 90% sequence identity to—SEQ ID NOS: 16 and 17, respectively; and one or more U6 promoter sequences operably coupled to the one or more guide RNA sequences. The U6 promoter sequences may comprise, or share at least 90% sequence identity with, SEQ ID NO: 9.

This listing is intended to be exemplary and illustrative rather than comprehensive and limiting. Additional aspects and embodiments may be set out in, or apparent from, the remainder of this disclosure and the claims.

DESCRIPTION OF THE DRAWINGS

The accompanying drawings exemplify certain aspects and embodiments of the present disclosure. The depictions in the drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic, two- or three-dimensional structures; these depictions are intended to be illustrative, rather than limiting or binding to any particular model or theory regarding their structure.

FIG. 1A shows an AAV genome for use in altering a CEP290 target position which encodes, inter alia, two guide RNAs having specific targeting domains selected from SEQ ID NOS: 1-3 and 4-6 and an *S. aureus* Cas9.

FIG. 1B shows an AAV genome that may be used for a variety of applications, including without limitation the alteration of the CEP290 target position, encoding two guide RNAs comprising the sequences of SEQ ID NOS. 7 and/or 8 and an *S. aureus* Cas9. FIG. 1C shows an AAV genome encoding one or two guide RNAs, each driven by a U6 promoter, and an *S. aureus* Cas9. In the figure, N may be 1 or two.

FIG. 3 schematically depicts a gRNA used in certain embodiments of the disclosure.

DETAILED DESCRIPTION

Definitions and Abbreviations

Figure 1A:
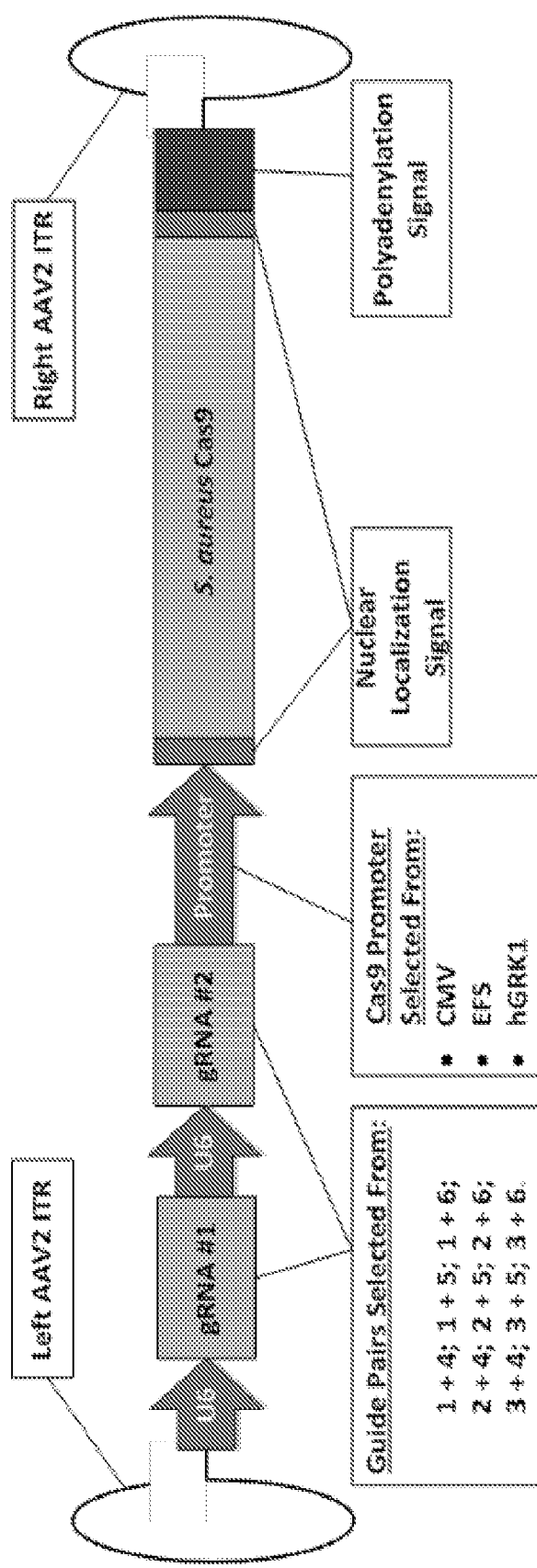
FIGS. 1A-C include schematic depictions of exemplary AAV viral genome according to certain embodiments of the disclosure.

Unless otherwise specified, each of the following terms has the meaning set forth in this section.

The indefinite articles "a" and "an" denote at least one of the associated noun, and are used interchangeably with the terms "at least one" and "one or more." For example, the phrase "a module" means at least one module, or one or more modules.

The conjunctions "or" and "and/or" are used interchangeably.

"Domain" is used to describe a segment of a protein or nucleic acid. Unless otherwise indicated, a domain is not required to have any specific functional property.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below. Indels are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing can be prepared by a variety of methods known in the art, and may involve the amplification of sites of interest by polymerase chain reaction (PCR) or the capture of DNA ends generated by double strand breaks, as in the GUIDEseq process described in Tsai 2016 (incorporated by reference herein). Other sample preparation methods are known in the art. Indels may also be assessed by other methods, including in situ hybridization methods such as the FiberComb™ system commercialized by Genomic Vision (Bagneux, France), and other methods known in the art.

"CEP290 target position" and "CEP290 target site" are used interchangeably herein to refer to a nucleotide or nucleotides in or near the CEP290 gene that are targeted for alteration using the methods described herein. In certain embodiments, a mutation at one or more of these nucleotides is associated with a CEP290 associated disease. The terms "CEP290 target position" and "CEP290 target site" are also used herein to refer to these mutations. For example, the IVS26 mutation is one non-limiting embodiment of a CEP290 target position/target site.

"Non-homologous end joining" or "NHEJ" as used herein refers to ligation mediated repair and/or non-template mediated repair including canonical NHEJ (cNHEJ), alternative NHEJ (altNHEJ), microhomology-mediated end joining (MMEJ) and synthesis-dependent microhomology-mediated end joining (SD-MMEJ).

"Replacement" or "replaced" as used herein with reference to a modification of a molecule does not require a process limitation but merely indicates that the replacement entity is present.

"Subject" means a human, mouse, or non-human primate. A human subject can be any age (e.g., an infant, child, young adult, or adult), and may suffer from a disease, or may be in need of alteration of a gene.

"Treat," "treating," and "treatment" as used herein mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" as used herein means the prevention of a disease in a subject, e.g., in a human, including (a) avoiding or precluding the disease; (b) affecting the predisposition toward the disease; (c) preventing or delaying the onset of at least one symptom of the disease.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic DNA, RNA, any synthetic and genetically manipulated polynucleotide, and both sense and antisense polynucleotides. This also includes nucleic acids containing modified bases.

Conventional IUPAC notation is used in nucleotide sequences presented herein, as shown in Table 1, below (see also Cornish-Bowden 1985, incorporated by reference herein). It should be noted, however, that "T" denotes "Thymine or Uracil" insofar as a given sequence (such as a gRNA sequence) may be encoded by either DNA or RNA.

TABLE 1

| IUPAC nucleic acid notation | |
| --- | --- |
| Character | Base |
| A | Adenine |
| T | Thymine |

TABLE 1-continued

IUPAC nucleic acid notation

| Character | Base |
|---|---|
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G, or T/U |
| V | A, C, or G | disease. Exemplary AAV vector genomes are schematized in FIGS. 1A through 1C, which illustrates certain fixed and variable elements of these vectors: inverted terminal repeats (ITRs), one or two gRNA sequences and promoter sequences to drive their expression, a Cas9 coding sequence and another promoter to drive its expression. Each of these elements is discussed in detail below.

Turning first to the gRNA pairs utilized in the nucleic acids or AAV vectors of the present disclosure, one of three "left" or "upstream" guides may be used to cut upstream (between exon 26 and the IVS26 mutation), and one of three "right" or "downstream" guides is used to cut downstream (between the IVS26 mutation and exon 27). Targeting domain sequences of these guides are presented in Table 2, below:

TABLE 2

Upstream (left) and Downstream (right) gRNA Targeting Domain Sequences

| Upstream (left) guides | | |
|---|---|---|
| Targeting domain | DNA | RNA |
| CEP290-323 | GTTCTGTCCTCAGTAAAAGGTA (SEQ ID NO: 1) | GUUCUGUCCUCAGUAAAAGGUA (SEQ ID NO: 26) |
| CEP290-490 | GAATAGTTTGTTCTGGGTAC (SEQ ID NO: 2) | GAAUAGUUUGUUCUGGGUAC (SEQ ID NO: 27) |
| CEP290-492 | GAGAAAGGGATGGGCACTTA (SEQ ID NO: 3) | GAGAAAGGGAUGGGCACUUA (SEQ ID NO: 28) |
| Downstream (right) guides | | |
| Targeting domain | DNA | RNA |
| CEP290-64 | GTCAAAAGCTACCGGTTACCTG (SEQ ID NO: 4) | GUCAAAAGCUACCGGUUACCUG (SEQ ID NO: 29) |
| CEP290-496 | GATGCAGAACTAGTGTAGAC (SEQ ID NO: 5) | GAUGCAGAACUAGUGUAGAC (SEQ ID NO: 30) |
| CEP290-504 | GAGTATCTCCTGTTTGGCA (SEQ ID NO: 6) | GAGUAUCUCCUGUUUGGCA (SEQ ID NO: 31) |

TABLE 1-continued

IUPAC nucleic acid notation

| Character | Base |
|---|---|
| H | A, C, or T/U |
| D | A, G, or T/U |
| N | A, C, G, or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments, variants, derivatives and analogs of such proteins. Peptide sequences are presented using conventional notation, beginning with the amino or N-terminus on the left, and proceeding to the carboxyl or C-terminus on the right. Standard one-letter or three-letter abbreviations may be used.

Overview

In certain aspects, the present disclosure focuses on AAV vectors encoding CRISPR/Cas9 genome editing systems, and on the use of such vectors to treat CEP290 associated The left and right guides can be used in any combination, though certain combinations may be more suitable for certain applications. Table 3 sets forth several upstream+downstream guide pairs used in the embodiments of this disclosure. It should be noted, notwithstanding the use of "left" and "right" as nomenclature for gRNAs, that any guide in a pair, upstream or downstream, may be placed in either one of the gRNA coding sequence positions illustrated in FIG. 1.

TABLE 3

Upstream (Left) + Downstream (Right) Guide Pairs

| | | Downstream | | |
|---|---|---|---|---|
| | | 4 | 5 | 6 |
| Upstream | 1 | 1 + 4 | 1 + 5 | 1 + 6 |
| | 2 | 2 + 4 | 2 + 5 | 2 + 6 |
| | 3 | 3 + 4 | 3 + 5 | 3 + 6 |

In some embodiments, the gRNAs used in the present disclosure are derived from *S. aureus* gRNAs and can be unimolecular or modular, as described below. An exemplary unimolecular *S. aureus* gRNA is shown in FIG. 3, and exemplary DNA and RNA sequences corresponding to unimolecular *S. aureus* gRNAs are shown below:

DNA:
(SEQ ID NO: 7)
[N]₁₆₋₂₄GTTTTAGTACTCTGGAAA<u>CAGAATCTACTAAAACAAGGCAAA</u>

<u>ATGCCGTGTTTATCTCGTCAACTTGTTGGCGAGATTTTTT</u>
and

RNA:
(SEQ ID NO: 32)
[N]₁₆₋₂₄GUUUUAGUACUCUGGAAA<u>CAGAAUCUACUAAAACAAGGCAAA</u>

<u>AUGCCGUGUUUAUCUCGUCAACUUGUUGGCGAGAUUUUUU</u>.

DNA:
(SEQ ID NO: 8)
[N]₁₆₋₂₄GTTATAGTACTCTGGAAA<u>CAGAATCTACTATAACAAGGCAAA</u>

<u>ATGCCGTGTTTATCTCGTCAACTTGTTGGCGAGATTTTTT</u>
and

RNA:
(SEQ ID NO: 33)
[N]₁₆₋₂₄GUUAUAGUACUCUGGAAA<u>CAGAAUCUACUAUAACAAGGCAAA</u>

<u>AUGCCGUGUUUAUCUCGUCAACUUGUUGGCGAGAUUUUUU</u>.

It should be noted that, while the figure depicts a targeting domain of 20 nucleotides, the targeting domain can have any suitable length. gRNAs used in the various embodiments of this disclosure preferably include targeting domains of between 16 and 24 (inclusive) bases in length at their 5' ends, and optionally include a 3' U6 termination sequence as illustrated.

The gRNA in FIG. 3 is depicted as unimolecular, but in some instances modular guides can be used. In the exemplary unimolecular gRNA sequences above, a 5' portion corresponding to a crRNA (underlined) is connected by a GAAA linker to a 3' portion corresponding to a tracrRNA (double underlined). Skilled artisans will appreciate that two-part modular gRNAs can be used that correspond to the underlined and double underlined sections.

Either one of the gRNAs presented above can be used with any of targeting sequences 1-6, and two gRNAs in a pair do not necessarily include the same backbone sequence. Additionally, skilled artisans will appreciate that the exemplary gRNA designs set forth herein can be modified in a variety of ways, which are described below or are known in the art; the incorporation of such modifications is within the scope of this disclosure.

Expression of each of the gRNAs in the AAV vector is driven by a pair of U6 promoters, such as a human U6 promoter. An exemplary U6 promoter sequence, as set forth in Maeder, is presented below:

(SEQ ID NO: 9)
AAGGTCGGGCAGGAAGAGGGCCTATTTCCCATGATTCCTTCATATTTGCA

TATACGATACAAGGCTGTTAGAGAGATAATTAGAATTAATTTGACTGTAA

ACACAAAGATATTAGTACAAAATACGTGACGTAGAAAGTAATAATTTCTT

GGGTAGTTTGCAGTTTTAAAATTATGTTTTAAAATGGACTATCATATGCT

TACCGTAACTTGAAAGTATTTCGATTTCTTGGCTTTATATATCTTGTGGA

AAGGACGAAACACC.

Turning next to Cas9, in some embodiments the Cas9 protein is *S. aureus* Cas9. In further embodiments of this disclosure an *S. aureus* Cas9 sequence is modified to include two nuclear localization sequences (NLSs) at the C- and N-termini of the Cas9 protein, and a mini-polyadenylation signal (or Poly-A sequence). Exemplary *S. aureus* Cas9 sequences (both nucleotide and peptide) are shown below:

TABLE 4 saCas9 Sequences

| | |
|---|---|
| Codon-<br>optimized<br>*S. aureus*<br>Cas9<br>nucleotide<br>(SEQ ID<br>NO: 10) | ATGAAAAGGAACTACATTCTGGGGCTGGACATCGGGATTACAAGCGTGGGG<br>TATGGGATTATTGACTATGAAACAAGGGACGTGATCGACGCAGGCGTCAGA<br>CTGTTCAAGGAGGCCAACGTGGAAAACAATGAGGGACGGAGAAGCAAGAG<br>GGGAGCCAGGCGCCTGAAACGACGGAGAAGGCACAGAATCCAGAGGGTGA<br>AGAAACTGCTGTTCGATTACAACCTGCTGACCGACCATTCTGAGCTGAGTGG<br>AATTAATCCTTATGAAGCCAGGGTGAAAGGCCTGAGTCAGAAGCTGTCAGA<br>GGAAGAGTTTTCCGCAGCTCTGCTGCACCTGGCTAAGCGCCGAGGAGTGCAT<br>AACGTCAATGAGGTGGAAGAGGACACCGGCAACGAGCTGTCTACAAAGGAA<br>CAGATCTCACGCAATAGCAAAGCTCTGGAAGAGAAGTATGTCGCAGAGCTG<br>CAGCTGGAACGGCTGAAGAAAGATGGCGAGGTGAGAGGGTCAATTAATAGG<br>TTCAAGACAAGCGACTACGTCAAAGAAGCCAAGCAGCTGCTGAAAGTGCAG<br>AAGGCTTACCACCAGCTGGATCAGAGCTTCATCGATACTTATATCGACCTGC<br>TGGAGACTCGGAGAACCTACTATGAGGGACCAGGAGAAGGGAGCCCCTTCG<br>GATGGAAAGACATCAAGGAATGGTACGAGATGCTGATGGGACATTGCACCT<br>ATTTTCCAGAAGAGCTGAGAAGCGTCAAGTACGCTTATAACGCAGATCTGTA<br>CAACGCCCTGAATGACCTGAACAACCTGGTCATCACCAGGGATGAAAACGA<br>GAAACTGGAATACTATGAGAAGTTCCAGATCATCGAAAACGTGTTTAAGCAG<br>AAGAAAAAGCCTACACTGAAACAGATTGCTAAGGAGATCCTGGTCAACGAA<br>GAGGACATCAAGGGCTACCGGGTGACAAGCACTGGAAAACCAGAGTTCACC<br>AATCTGAAAGTGTATCACGATATTAAGGACATCACAGCACGGAAAGAAATC<br>ATTGAGAACGCCGAACTGCTGGATCAGATTGCTAAGATCCTGACTATCTACC<br>AGAGCTCCGAGGACATCCAGGAAGAGCTGACTAACCTGAACAGCGAGCTGA<br>CCCAGGAAGAGATCGAACAGATTAGTAATCTGAAGGGGTACACCGGAACAC<br>ACAACCTGTCCCTGAAAGCTATCAATCTGATTCTGGATGAGCTGTGGCATAC<br>AAACGACAATCAGATTGCAATCTTTAACCGGCTGAAGCTGGTCCCAAAAAAG<br>GTGGACCTGAGTCAGCAGAAAGAGATCCCAACCACACTGGTGGACGATTTC<br>ATTCTGTCACCCGTGGTCAAGCGGAGCTTCATCCAGAGCATCAAAGTGATCA<br>ACGCCATCATCAAGAAGTACGGCCTGCCCAATGATATCATTATCGAGCTGGC<br>TAGGGAGAAGAACAGCAAGGACGCACAGAAGATGATCAATGAGATGCAGA<br>AACGAAACCGGCAGACCAATGAACGCATTGAAGAGATTATCCGAACTACCG<br>GGAAAGAGAACGCAAAGTACCTGATTGAAAAAATCAAGCTGCACGATATGC<br>AGGAGGGAAAGTGTCTGTATTCTCTGGAGGCCATCCCCCTGGAGGACCTGCT<br>GAACAATCCATTCAACTACGAGGTCGATCATATTATCCCCAGAAGCGTGTCC<br>TTCGACAATTCCTTTAACAACAAGGTGCTGGTCAAGCAGGAAGAGAACTCTA |

TABLE 4-continued saCas9 Sequences

```
AAAAGGGCAATAGGACTCCTTTCCAGTACCTGTCTAGTTCAGATTCCAAGAT
CTCTTACGAAACCTTTAAAAAGCACATTCTGAATCTGGCCAAAGGAAAGGGC
CGCATCAGCAAGACCAAAAAGGAGTACCTGCTGGAAGAGCGGGACATCAAC
AGATTCTCCGTCCAGAAGGATTTTATTAACCGGAATCTGGTGGACACAAGAT
ACGCTACTCGCGGCCTGATGAATCTGCTGCGATCCTATTTCCGGGTGAACAA
TCTGGATGTGAAAGTCAAGTCCATCAACGGCGGGTTCACATCTTTTCTGAGG
CGCAAATGGAAGTTTAAAAAGGAGCGCAACAAAGGGTACAAGCACCATGCC
GAAGATGCTCTGATTATCGCAAATGCCGACTTCATCTTTAAGGAGTGGAAAA
AGCTGGACAAAGCCAAGAAAGTGATGGAGAACCAGATGTTCGAAGAGAAGC
AGGCCGAATCTATGCCCGAAATCGAGACAGAACAGGAGTACAAGGAGATTT
TCATCACTCCTCACCAGATCAAGCATATCAAGGATTTCAAGGACTACAAGTA
CTCTCACCGGGTGGATAAAAAGCCCAACAGAGACiCTGATCAATGACACCCT
GTATAGTACAAGAAAAGACGATAAGGGGAATACCCTGATTGTGAACAATCT
GAACGGACTGTACGACAAAGATAATGACAAGCTGAAAAAGCTGATCAACAA
AAGTCCCGAGAAGCTGCTGATGTACCACCATGATCCTCAGACATATCAGAAA
CTGAAGCTGATTATGGAGCAGTACGGCGACGAGAAGAACCCACTGTATAAG
TACTATGAAGAGACTGGGAACTACCTGACCAAGTATAGCAAAAAGGATAAT
GGCCCCGTGATCAAGAAGATCAAGTACTATGGGAACAAGCTGAATGCCCAT
CTGGACATCACAGACGATTACCCTAACAGTCGCAACAAGGTGGTCAAGCTGT
CACTGAAGCCATACAGATTCGATGTCTATCTGGACAACGGCGTGTATAAATT
TGTGACTGTCAAGAATCTGGATGTCATCAAAAAGGAGAACTACTATGAAGTG
AATAGCAAGTGCTACGAAGAGGCTAAAAAGCTGAAAAAGATTAGCAACCAG
GCAGAGTTCATCGCCTCCTTTTACAACAACGACCTGATTAAGATCAATGGCG
AACTGTATAGGGTCATCGGGGTGAACAATGATCTGCTGAACCGCATTGAAGT
GAATATGATTGACATCACTTACCGAGAGTATCTGGAAAACATGAATGATAAG
CGCCCCCCTCGAATTATCAAAACAATTGCCTCTAAGACTCAGAGTATCAAA
AGTACTCAACCGACATTCTGGGAAACCTGTATGAGGTGAAGAGCAAAAAGC
ACCCTCAGATTATCAAAAAGGGC
```

S. aureus Cas9 protein (SEQ ID NO: 11)

```
MKRNYILGLDIGITSVGYGIIDYETRDVIDAGVRLFKEANVENNEGRRSKRGARR
LKRRRRHRIQRVKKLLFDYNLLTDHSELSGINPYEARVKGLSQKLSEEEFSAALL
HLAKRRGVHNVNEVEEDTGNELSTKEQISRNSKALEEKYVAELQLERLKKDGE
VRGSINRFKTSDYVKEAKQLLKVQKAYHQLDQSFIDTYIDLLETRRTYYEGPGE
GSPFGWKDIKEWYEMLMGHCTYFPEELRSVKYAYNADLYNALNDLNNLVITRD
ENEKLEYYEKFQIIENVFKQKKKPTLKQIAKEILVNEEDIKGYRVTSTGKPEFTNL
KVYHDIKDITARKEIIENAELLDQIAKILTIYQSSEDIQEELTNLNSELTQEEIEQISN
LKGYTGTHNLSLKAINLILDELWHTNDNQIAIFNRLKLVPKKVDLSQQKEIPTTL
VDDFILSPVVKRSFIQSIKVINAIIKKYGLPNDIIIELAREKNSKDAQKMINEMQKR
NRQTNERIEEIIRTTGKENAKYLIEKIKLHDMQEGKCLYSLEAIPLEDLLNNPFNY
EVDHIIPRSVSFDNSFNNKVLVKQEENSKKGNRTPFQYLSSSDSKISYETFKKHIL
NLAKGKGRISKTKKEYLLEERDINRFSVQKDFINRNLVDTRYATRGLMNLLRSY
FRVNNLDVKVKSINGGFTSFLRRKWKFKKERNKGYKHHAEDALIIANADFIFKE
WKKLDKAKKVMENQMFEEKQAESMPEIETEQEYKEIFITPHQIKHIKDFKDYKY
SHRVDKKPNRELINDTLYSTRKDDKGNTLIVNNLNGLYDKDNDKLKKLINKSPE
KLLMYHHDPQTYQKLKLIMEQYGDEKNPLYKYYEETGNYLTKYSKKDNGPVIK
KIKYYGNKLNAHLDITDDYPNSRNKVVKLSLKPYRFDVYLDNGVYKFVTVKNL
DVIKKENYYEVNSKCYEEAKKLKKISNQAEFIASFYNNDLIKINGELYRVIGVNN
DLLNRIEVNMIDITYREYLENMNDKRPPRIIKTIASKTQSIKKYSTDILGNLYEVKS
KKHPQIIKKG
```

These sequences are exemplary in nature, and are not intended to be limiting. The skilled artisan will appreciate that modifications of these sequences may be possible or desirable in certain applications; such modifications are described below, or are known in the art, and are within the scope of this disclosure.

Skilled artisans will also appreciate that polyadenylation signals are widely used and known in the art, and that any suitable polyadenylation signal can be used in the embodiments of this disclosure. One exemplary polyadenylation signal is set forth below:

(SEQ ID NO: 12)
TAGCAATAAAGGATCGTTTATTTTCATTGGAAGCGTGTGTTGGTTTTTG
ATCAGGCGCG.

Cas9 expression is driven, in certain vectors of this disclosure, by one of three promoters: cytomegalovirus (CMV), elongation factor-1 (EFS), or human g-protein receptor coupled kinase-1 (hGRK1), which is specifically expressed in retinal photoreceptor cells. Nucleotide sequences for each of these promoters are provided in Table 5. Modifications of these sequences may be possible or desirable in certain applications, and such modifications are within the scope of this disclosure.

TABLE 5

Cas9 Promoter Sequences

| | |
|---|---|
| CMV (SEQ ID NO: 13) | CATTGATTATTGACTAGTTATTAATAGTAATCAATTACGGGGTCATTAG TTCATAGCCCATATATGGAGTTCCGCGTTACATAACTTACGGTAAATGG CCCGCCTGGCTGACCGCCCAACGACCCCCGCCCATTGACGTCAATAAT GACGTATGTTCCCATAGTAACGCCAATAGGGACTTTCCATTGACGTCAA |

TABLE 5-continued

Cas9 Promoter Sequences

|  |  |
|---|---|
|  | TGGGTGGACTATTTACGGTAAACTGCCCACTTGGCAGTACATCAAGTGT<br>ATCATATGCCAAGTACGCCCCCTATTGACGTCAATGACGGTAAATGGC<br>CCGCCTGGCATTATGCCCAGTACATGACCTTATGGGACTTTCCTACTTG<br>GCAGTACATCTACGTATTAGTCATCGCTATTACCATGGTGATGCGGTTT<br>TGGCAGTACATCAATGGGCGTGGATAGCGGTTTGACTCACGGGGATTT<br>CCAAGTCTCCACCCCATTGACGTCAATGGGAGTTTGTTTTGGCACCAAA<br>ATCAACGGGACTTTCCAAAATGTCGTAACAACTCCGCCCCATTGACGC<br>AAATGGGCGGTAGGCGTGTACGGTGGGAGGTCTATATAAGCAGAGCTG<br>GTTTAGTGAACCGTCAGATCCGCTAGAGATCCGC |
| EFS<br>(SEQ ID NO: 14) | TCGAGTGGCTCCGGTGCCCGTCAGTGGGCAGAGCGCACATCGCCCACA<br>GTCCCCGAGAAGTTGGGGGGAGGGGTCGGCAATTGAACCGGTGCCTAG<br>AGAAGGTGGCGCGGGGTAAACTGGGAAAGTGATGTCGTGTACTGGCTC<br>CGCCTTTTTCCCGAGGGTGGGGGAGAACCGTATATAAGTGCAGTAGTC<br>GCCGTGAACGTTCTTTTTCGCAACGGGTTTGCCGCCAGAACACAGGTGT<br>CGTGACCGCGG |
| hGRK1<br>(SEQ ID NO: 15) | GGGCCCCAGAAGCCTGGTGGTTGTTTGTCCTTCTCAGGGGAAAAGTGA<br>GGCGGCCCCTTGGAGGAAGGGGCCGGGCAGAATGATCTAATCGGATTC<br>CAAGCAGCTCAGGGGATTGTCTTTTTCTAGCACCTTCTTGCCACTCCTA<br>AGCGTCCTCCGTGACCCCGGCTGGGATTTCGCCTGGTGCTGTGTCAGCC<br>CCGGTCTCCCAGGGGCTTCCCAGTGGTCCCCAGGAACCCTCGACAGGG<br>CCCGGTCTCTCTCGTCCAGCAAGGGCAGGGACGGGCCACAGGCCAAGG<br>GC |

AAV genomes according to the present disclosure generally incorporate inverted terminal repeats (ITRs) derived from the AAV2 serotype. Exemplary left and right ITRs are presented in Table 6. It should be noted, however, that numerous modified versions of the AAV2 ITRs are used in the field, and the ITR sequences shown below are exemplary and are not intended to be limiting. Modifications of these sequences are known in the art, or will be evident to skilled artisans, and are thus included in the scope of this disclosure.

TABLE 6

AAV2 ITR Sequences

| AAV2<br>Left<br>ITR<br>(SEQ ID<br>NO: 16) | TTGGCCACTCCCTCTCTGCGCGCTCGCTCGCTCACTGAGG<br>CCGGGCGACCAAAGGTCGCCCGACGCCCGGGCTTTGCCC<br>GGGCGGCCTCAGTGAGCGAGCGAGCGCGCAGAGAGGGA<br>GTGGCCAACTCCATCACTAGGGGTTCCT |
|---|---|
| AAV2<br>Right<br>ITR<br>(SEQ ID<br>NO: 17) | AGGAACCCCTAGTGATGGAGTTGGCCACTCCCTCTCTGCG<br>CGCTCGCTCGCTCACTGAGGCCGCCCGGGCAAAGCCCGG<br>GCGTCGGGCGACCTTTGGTCGCCCGGCCTCAGTGAGCGA<br>GCGAGCGCGCAGAGAGGGAGTGGCCAA |

As FIG. 1 illustrates, the gRNA pairs and the Cas9 promoter are variable and can be selected from the lists presented above. For clarity, this disclosure encompasses nucleic acids and/or AAV vectors comprising any combination of these elements, though certain combinations may be preferred for certain applications. Accordingly, in various embodiments of this disclosure, a nucleic acid or AAV vector encodes a CMV promoter for the Cas9, and gRNAs comprising targeting domains according to SEQ ID NOS: 1 and 4; a CMV promoter and gRNAs comprising targeting domains according to SEQ ID NOS: 1 and 5; a CMV promoter and gRNAs comprising targeting domains according to SEQ ID NOS: 1 and 6; a CMV promoter and gRNAs comprising targeting domains according to SEQ ID NOS: 2 and 4; a CMV promoter and gRNAs comprising targeting domains according to SEQ ID NOS: 2 and 5; a CMV promoter and gRNAs comprising targeting domains according to SEQ ID NOS: 2 and 6; a CMV promoter and gRNAs comprising targeting domains according to SEQ ID NOS: 3 and 4; a CMV promoter and gRNAs comprising targeting domains according to SEQ ID NOS: 3 and 5; a CMV promoter and gRNAs comprising targeting domains according to SEQ ID NOS: 3 and 6; an EFS promoter and gRNAs comprising targeting domains according to SEQ ID NOS: 1 and 4; an EFS promoter and gRNAs comprising targeting domains according to SEQ ID NOS: 1 and 5; an EFS promoter and gRNAs comprising targeting domains according to SEQ ID NOS: 1 and 6; an EFS promoter and gRNAs comprising targeting domains according to SEQ ID NOS: 2 and 4; an EFS promoter and gRNAs comprising targeting domains according to SEQ ID NOS: 2 and 5; an EFS promoter and gRNAs comprising targeting domains according to SEQ ID NOS: 2 and 6; an EFS promoter and gRNAs comprising targeting domains according to SEQ ID NOS: 3 and 4; an EFS promoter and gRNAs comprising targeting domains according to SEQ ID NOS: 3 and 5; an EFS promoter and gRNAs comprising targeting domains according to SEQ ID NOS: 3 and 6; an hGRK1 promoter and gRNAs comprising targeting domains according to SEQ ID NOS: 1 and 4; an hGRK1 promoter and gRNAs comprising targeting domains according to SEQ ID NOS: 1 and 5; an hGRK1 promoter and gRNAs comprising targeting domains according to SEQ ID NOS: 1 and 6; an hGRK1 promoter and gRNAs comprising targeting domains according to SEQ ID NOS: 2 and 4; an hGRK1 promoter and gRNAs comprising targeting domains according to SEQ ID NOS: 2 and 5; an hGRK1 promoter and gRNAs comprising targeting domains according to SEQ ID NOS: 2 and 6; an hGRK1 promoter and gRNAs comprising targeting domains according to SEQ ID NOS: 3 and 4; an hGRK1 promoter and gRNAs comprising targeting domains according to SEQ ID NOS: 3 and 5; or an hGRK1 promoter and gRNAs comprising targeting domains according to SEQ ID NOS: 3 and 6.

In various embodiments, the nucleic acid or AAV vector encodes the following: left and right AAV2 ITR sequences, a first U6 promoter to drive expression of a first guide RNA having a sequence selected from SEQ ID NOS: 7 and 8 (corresponding RNA sequences in SEQ ID NOs: 32, and 33, respectively) and/or comprising a targeting domain sequence according to one of SEQ ID NOS: 1-3 (corresponding RNA sequences in SEQ ID NOs: 26-28, respectively), a second U6 promoter to drive expression of a second guide RNA comprising a sequence selected from SEQ ID NOS: 7 and 8 and/or comprising a targeting domain sequence according to one of SEQ ID NOS: 4-6 (corresponding RNA sequences in SEQ ID NOs: 29-31, respectively), and a CMV promoter to drive expression of an S. aureus Cas9 encoded by SEQ ID NO: 10; or left and right AAV2 ITR sequences, a first U6 promoter to drive expression of a first guide RNA having a sequence selected from SEQ ID NOS: 7 and 8 and/or comprising a targeting domain sequence according to one of SEQ ID NOS: 1-3, a second U6 promoter to drive expression of a second guide RNA comprising a sequence selected from SEQ ID NOS: 7 and 8 and/or comprising a targeting domain sequence according to one of SEQ ID NOS: 4-6, and an hGRK promoter to drive expression of an S. aureus Cas9 encoded by SEQ ID NO: 10; or left and right AAV2 ITR sequences, a first U6 promoter to drive expression of a first guide RNA having a sequence selected from SEQ ID NOS: 7 and 8 and/or comprising a targeting domain sequence according to one of SEQ ID NOS: 1-3, a second U6 promoter to drive expression of a second guide RNA comprising a sequence selected from SEQ ID NOS: 7 and 8 and/or comprising a targeting domain sequence according to one of SEQ ID NOS: 4-6, and an EFS promoter to drive expression of an S. aureus Cas9 encoded by SEQ ID NO: 10.

In some embodiments, the nucleic acid or AAV vector shares at least 80%, 85%, 90%, 95%, 96%, 97%, 98%, 99% or greater sequence identity with one of the nucleic acids or AAV vectors recited above.

It should be noted that these sequences described above are exemplary, and can be modified in ways that do not disrupt the operating principles of elements they encode. Such modifications, some of which are discussed below, are within the scope of this disclosure. Without limiting the foregoing, skilled artisans will appreciate that the DNA, RNA or protein sequences of the elements of this disclosure may be varied in ways that do not interrupt their function, and that a variety of similar sequences that are substantially similar (e.g., greater than 90%, 95%, 96%, 97%, 98% or 99% sequence similarity, or in the case of short sequences such as gRNA targeting domains, sequences that differ by no more than 1, 2 or 3 nucleotides) can be utilized in the various systems, methods and AAV vectors described herein. Such modified sequences are within the scope of this disclosure.

The AAV genomes described above can be packaged into AAV capsids (for example, AAV5 capsids), which capsids can be included in compositions (such as pharmaceutical compositions) and/or administered to subjects. An exemplary pharmaceutical composition comprising an AAV capsid according to this disclosure can include a pharmaceutically acceptable carrier such as balanced saline solution (BSS) and one or more surfactants (e.g., Tween 20) and/or a thermosensitive or reverse-thermosensitive polymer (e.g., pluronic). Other pharmaceutical formulation elements known in the art may also be suitable for use in the compositions described here.

Compositions comprising AAV vectors according to this disclosure can be administered to subjects by any suitable means, including without limitation injection, for example, subretinal injection. The concentration of AAV vector within the composition is selected to ensure, among other things, that a sufficient AAV dose is administered to the retina of the subject, taking account of dead volume within the injection apparatus and the relatively limited volume that can be safely administered to the retina. Suitable doses may include, for example, $1 \times 10^{11}$ viral genomes (vg)/mL, $2 \times 10^{11}$ viral genomes (vg)/mL, $3 \times 10^{11}$ viral genomes (vg)/mL, $4 \times 10^{11}$ viral genomes (vg)/mL, $5 \times 10^{11}$ viral genomes (vg)/mL, $6 \times 10^{11}$ viral genomes (vg)/mL, $7 \times 10^{11}$ viral genomes (vg)/mL, $8 \times 10^{11}$ viral genomes (vg)/mL, $9 \times 10^{11}$ viral genomes (vg)/mL, $1 \times 10^{12}$ vg/mL, $2 \times 10^{12}$ viral genomes (vg)/mL, $3 \times 10^{12}$ viral genomes (vg)/mL, $4 \times 10^{12}$ viral genomes (vg)/mL, $5 \times 10^{12}$ viral genomes (vg)/mL, $6 \times 10^{12}$ viral genomes (vg)/mL, $7 \times 10^{12}$ viral genomes (vg)/mL, $8 \times 10^{12}$ viral genomes (vg)/mL, $9 \times 10^{12}$ viral genomes (vg)/mL, $1 \times 10^{13}$ vg/mL, $2 \times 10^{13}$ viral genomes (vg)/mL, $3 \times 10^{13}$ viral genomes (vg)/mL, $4 \times 10^{13}$ viral genomes (vg)/mL, $5 \times 10^{13}$ viral genomes (vg)/mL, $6 \times 10^{13}$ viral genomes (vg)/mL, $7 \times 10^{13}$ viral genomes (vg)/mL, $8 \times 10^{13}$ viral genomes (vg)/mL, or $9 \times 10^{13}$ viral genomes (vg)/mL. Any suitable volume of the composition may be delivered to the subretinal space. In some instances, the volume is selected to form a bleb in the subretinal space, for example 1 microliter, 10 microliters, 50 microliters, 100 microliters, 150 microliters, 200 microliters, 250 microliters, 300 microliters, etc.

Any region of the retina may be targeted, though the fovea (which extends approximately 1 degree out from the center of the eye) may be preferred in certain instances due to its role in central visual acuity and the relatively high concentration of cone photoreceptors there relative to peripheral regions of the retina. Alternatively or additionally, injections may be targeted to parafoveal regions (extending between approximately 2 and 10 degrees off center), which are characterized by the presence of all three types of retinal photoreceptor cells. In addition, injections into the parafoveal region may be made at comparatively acute angles using needle paths that cross the midline of the retina. For instance, injection paths may extend from the nasal aspect of the sclera near the limbus through the vitreal chamber and into the parafoveal retina on the temporal side, from the temporal aspect of the sclera to the parafoveal retina on the nasal side, from a portion of the sclera located superior to the cornea to an inferior parafoveal position, and/or from an inferior portion of the sclera to a superior parafoveal position. The use of relatively small angles of injection relative to the retinal surface may advantageously reduce or limit the potential for spillover of vector from the bleb into the vitreous body and, consequently, reduce the loss of the vector during delivery. In other cases, the macula (inclusive of the fovea) can be targeted, and in other cases, additional retinal regions can be targeted, or can receive spillover doses.

For pre-clinical development purposes, systems, compositions, nucleotides and vectors according to this disclosure can be evaluated ex vivo using a retinal explant system, or in vivo using an animal model such as a mouse, rabbit, pig, nonhuman primate, etc. Retinal explants are optionally maintained on a support matrix, and AAV vectors can be delivered by injection into the space between the photoreceptor layer and the support matrix, to mimic subretinal injection. Tissue for retinal explantation can be obtained from human or animal subjects, for example mouse.

Explants are particularly useful for studying the expression of gRNAs and/or Cas9 following viral transduction, and for studying genome editing over comparatively short intervals. These models also permit higher throughput than may be possible in animal models, and can be predictive of expression and genome editing in animal models and subjects. Small (mouse, rat) and large animal models (such as rabbit, pig, nonhuman primate) can be used for pharmacological and/or toxicological studies and for testing the systems, nucleotides, vectors and compositions of this disclosure under conditions and at volumes that approximate those that will be used in clinic. Because model systems are selected to recapitulate relevant aspects of human anatomy and/or physiology, the data obtained in these systems will generally (though not necessarily) be predictive of the behavior of AAV vectors and compositions according to this disclosure in human and animal subjects.

Figure 1B:
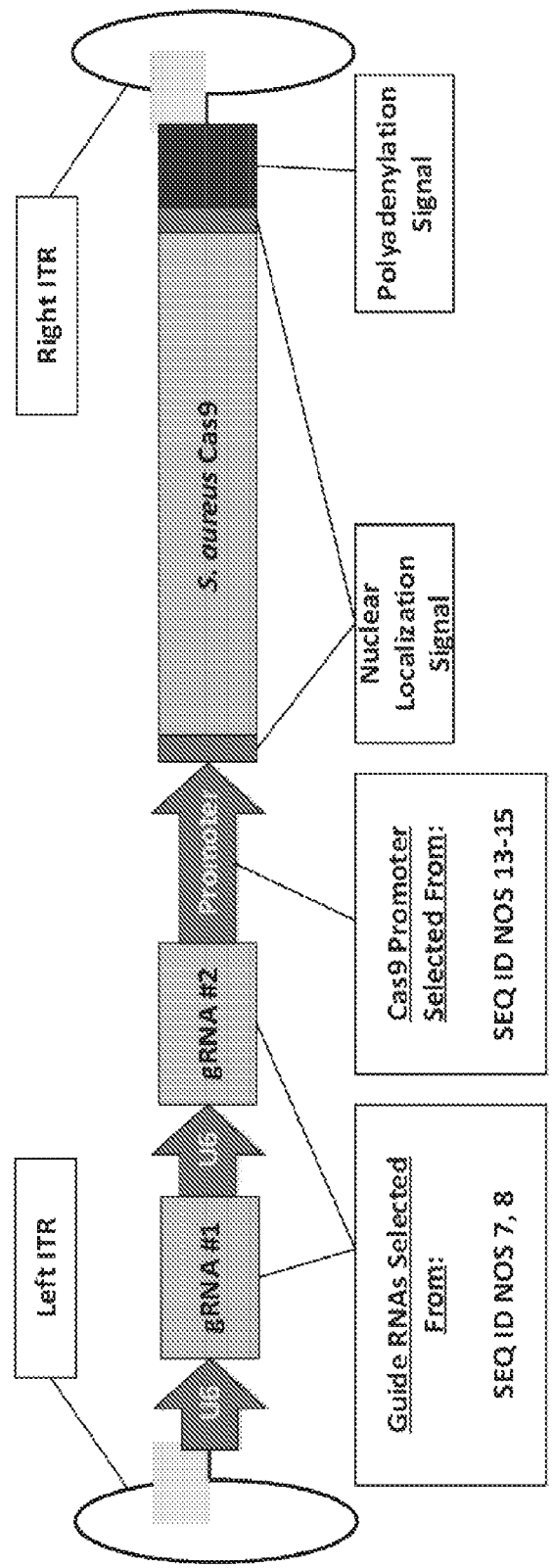
Figure 1C:
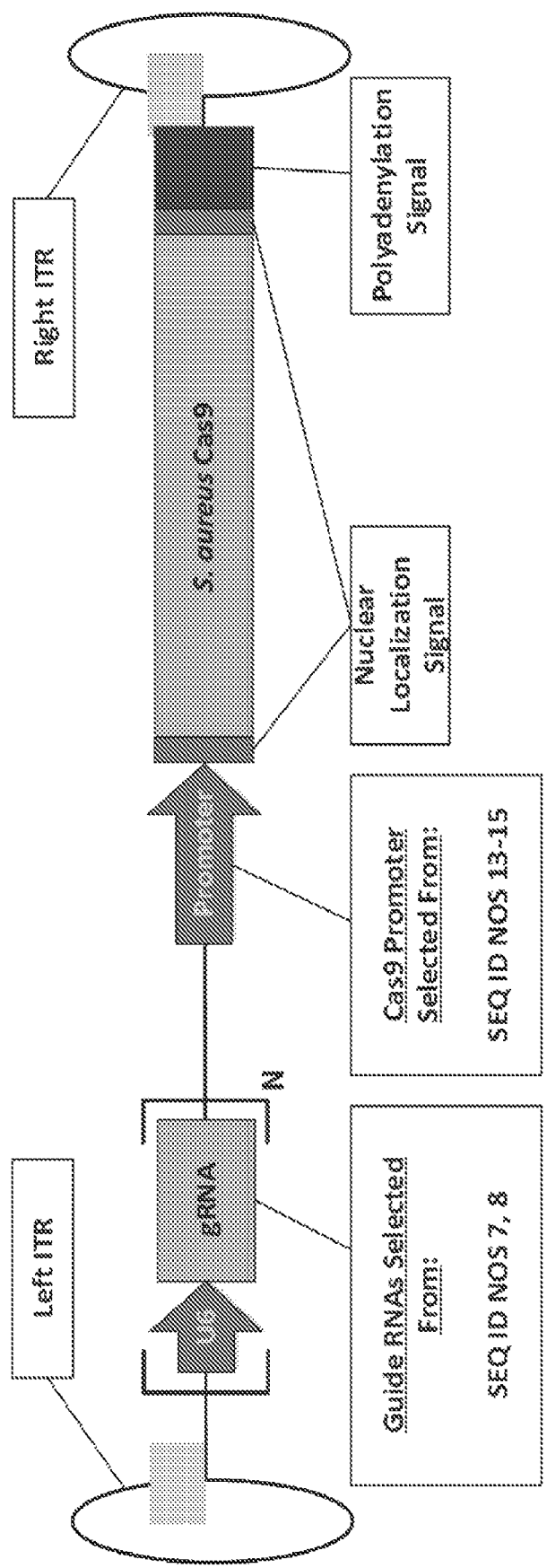
Figure 2:
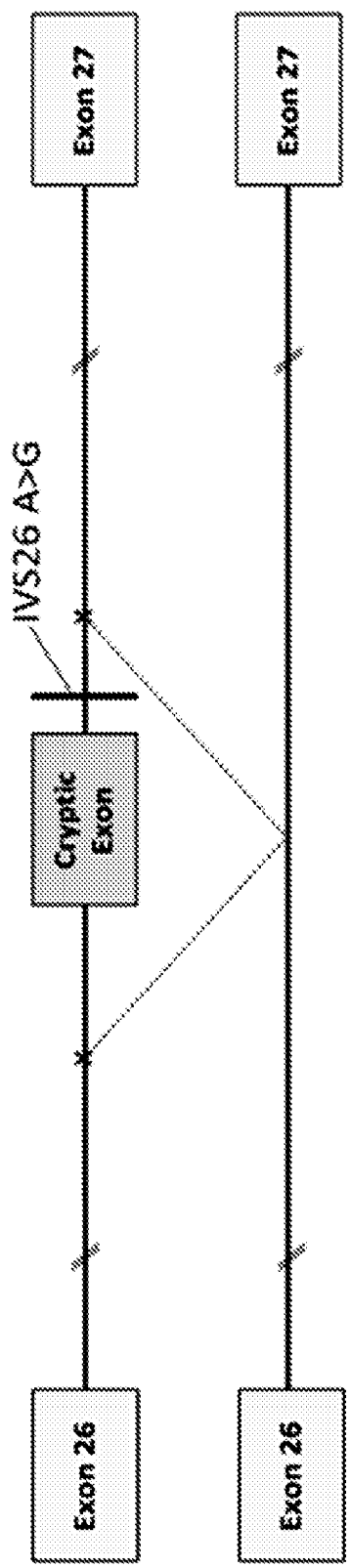
FIG. 2 illustrates the genome editing strategy implemented in certain embodiments of this disclosure.

While the foregoing exemplary embodiments have focused on guide RNAs, nucleic acids and AAV vectors targeted to the CEP290 gene, it will be appreciated by those of skill in the art that the nucleic acids and vectors of this disclosure may be used in the editing of other gene targets and the treatment of other diseases such as hereditary retinopathies that may be treated by editing of genes other than CEP290. FIGS. 1B and 1C illustrate two exemplary AAV vectors that may be used to transduce retinal cells, including without limitation retinal photoreceptor cells such as rod photoreceptors and/or cone photoreceptors, and/or other retinal cell types. The AAV genome of FIG. 1B comprises two guide RNAs according to SEQ ID NOS: 7 and/or 8, and a promoter sequence according to one of SEQ ID NOS: 13-15 driving expression of an S. aureus Cas9 comprising one or two nuclear localization signals and, optionally, a polyadenylation signal. The vector may additionally include ITRs such as AAV2 ITRs, or other sequences that may be selected for the specific application to which the vector will be employed. As is shown in FIG. 1C, other vectors within the scope of this disclosure may include only 1 guide RNA. Thus, in specific embodiments, an AAV genome of this disclosure may encode a CMV promoter for the Cas9 and one guide RNA having a sequence comprising, or sharing at least 90% sequence identity with, a sequence selected from SEQ ID NOS: 7 and 8; a CMV promoter for the Cas9 and two guide RNAs, each having a sequence comprising, or sharing at least 90% sequence identity with, a sequence selected from SEQ ID NOS: 7 and 8; an hGRK promoter for the Cas9 and one guide RNA having a sequence comprising, or sharing at least 90% sequence identity with, a sequence selected from SEQ ID NOS: 7 and 8; an hGRK promoter for the Cas9 and two guide RNAs, each having a sequence comprising, or sharing at least 90% sequence identity with, a sequence selected from SEQ ID NOS: 7 and 8; an EFS promoter for the Cas9 and one guide RNA having a sequence comprising, or sharing at least 90% sequence identity with, a sequence selected from SEQ ID NOS: 7 and 8; an EFS promoter for the Cas9 and two guide RNAs, each having a sequence comprising, or sharing at least 90% sequence identity with, a sequence selected from SEQ ID NOS: 7 and 8.

Genome Editing Systems

The term "genome editing system" refers to any system having RNA-guided DNA editing activity. Genome editing systems of the present disclosure include at least two components adapted from naturally occurring CRISPR systems: a gRNA and an RNA-guided nuclease. These two components form a complex that is capable of associating with a specific nucleic acid sequence in a cell and editing the DNA in or around that nucleic acid sequence, for example by making one or more of a single-strand break (an SSB or nick), a double-strand break (a DSB) and/or a base substitution.

Naturally occurring CRISPR systems are organized evolutionarily into two classes and five types (Makarova 2011, incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) that form ribonucleoprotein (RNP) complexes with gRNAs. gRNAs, which are discussed in greater detail below, can include single crRNAs in the case of Cpf1 or duplexed crRNAs and tracrRNAs in the case of Cas9. RNP complexes, in turn, associate with (i.e., target) and cleave specific loci complementary to a targeting (or spacer) sequence of the crRNA. Genome editing systems according to the present disclosure similarly target and edit cellular DNA sequences. but differ significantly from CRISPR systems occurring in nature. For example, the unimolecular gRNAs described herein do not occur in nature, and both gRNAs and RNA-guided nucleases according to this disclosure can incorporate any number of non-naturally occurring modifications.

Genome editing systems can be implemented in a variety of ways, and different implementations may be suitable for any particular application. For example, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In other embodiments, a genome editing system is implemented as one or more nucleic acids encoding the RNA-guided nuclease and gRNA components described above (optionally with one or more additional components); in still other embodiments, the genome editing system is implemented as one or more vectors comprising such nucleic acids, for example a viral vector such as an AAV; and in still other embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present invention can be targeted to a single specific nucleotide sequence, or can be targeted to—and capable of editing in parallel—two or more specific nucleotide sequences through the use of two or more gRNAs. The use of two or more gRNAs targeted to different sites is referred to as "multiplexing" throughout this disclosure, and can be employed to target multiple, unrelated target sequences of interest, or to form multiple SSBs and/or DSBs within a single target domain and, in some cases, to generate specific edits within such target domain. For example, this disclosure and Maeder both describe a genome editing system for correcting a point mutation (C.2991+1655A to G) in the human CEP290 gene that results in the creation of a cryptic splice site, which in turn reduces or eliminates the function of the gene. The genome editing system of Maeder utilizes two gRNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, International Patent Publication No. WO2016/073990 by Cotta-Ramusino et al. ("Cotta-Ramusino"), incorporated by reference herein, describes a genome editing system that utilizes two gRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, International Patent Publication No. WO2015/070083 by Zhang et al., incorporated by reference herein, describes a gRNA targeted to a nucleotide sequence encoding Cas9 (referred to as a "governing" gRNA), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as non-homologous end joining (NHEJ), or homology directed repair (HDR). These mechanisms are described throughout the literature (see, e.g., Davis 2014 (describing Alt-HDR), Frit 2014 (describing Alt-NHEJ), and Iyama 2013 (describing canonical HDR and NHEJ pathways generally), all of which are incorporated by reference herein).

Where genome editing systems operate by forming DSBs, such systems optionally include one or more components that promote or facilitate a particular mode of double-strand break repair or a particular repair outcome. For example, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In other cases, genome editing systems modify a target sequence, or modify expression of a gene in or near the target sequence, without causing single- or double-strand breaks. For example, a genome editing system can include an RNA-guided nuclease/cytidine deaminase fusion protein, and can operate by generating targeted C-to-A substitutions. Suitable nuclease/deaminase fusions are described in Komor 2016, which is incorporated by reference. Alternatively, a genome editing system can utilize a cleavage-inactivated (i.e., a "dead") nuclease, such as a dead Cas9, and can operate by forming stable complexes on one or more targeted regions of cellular DNA, thereby interfering with functions involving the targeted region(s) such as mRNA transcription and chromatin remodeling.

Guide RNA (gRNA)

The terms guide RNA and gRNA refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for example by duplexing). gRNAs and their component parts are described throughout the literature (see, e.g., Briner 2014, which is incorporated by reference; see also Cotta-Ramusino).

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric gRNA, for example by means of a four nucleotide (e.g., GAAA) "tetraloop" or "linker" sequence bridging complementary regions of the crRNA (at its 3' end) and the tracrRNA (at its 5' end) (Mali 2013; Jiang 2013; Jinek 2012; all incorporated by reference herein).

gRNAs, whether unimolecular or modular, include a targeting domain that is fully or partially complementary to a target domain within a target sequence, such as a DNA sequence in the genome of a cell where editing is desired. In certain embodiments, this target sequence encompasses or is proximal to a CEP290 target position. Targeting domains are referred to by various names in the literature, including without limitation "guide sequences" (Hsu 2013, incorporated by reference herein), "complementarity regions" (Cotta-Ramusino), "spacers" (Briner 2014), and generically as "crRNAs" (Jiang 2013). Irrespective of the names they are given, targeting domains are typically 10-30 nucleotides in length, preferably 16-24 nucleotides in length (for example, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that influence the formation or activity of gRNA/Cas9 complexes. For example, as mentioned above, the duplexed structure formed by first and secondary complementarity domains of a gRNA (also referred to as a repeat: anti-repeat duplex) interacts with the recognition (REC) lobe of Cas9 and may mediate the formation of Cas9/gRNA complexes (Nishimasu 2014; Nishimasu 2015; both incorporated by reference herein). It should be noted that the first and/or second complementarity domains can contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for example through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are necessary for nuclease activity in vivo but not necessarily in vitro (Nishimasu 2015). A first stem-loop near the 3' portion of the second complementarity domain is referred to variously as the "proximal domain," (Cotta-Ramusino) "stem loop 1" (Nishimasu 2014; Nishimasu 2015) and the "*nexus*" (Briner 2014). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while s. *aureus* and other species have only one (for a total of three).

A description of conserved stem loop structures (and gRNA structures more generally) organized by species is provided in Briner 2014.

Skilled artisans will appreciate that gRNAs can be modified in a number of ways, some of which are described below, and these modifications are within the scope of disclosure. For economy of presentation in this disclosure, gRNAs may be presented by reference solely to their targeting domain sequences.

gRNA Modifications

The activity, stability, or other characteristics of gRNAs can be altered through the incorporation of chemical and/or sequential modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into a population of cells, particularly the cells of the present invention. As noted above, the term "innate immune response" includes a cellular response to exogenous nucleic acids, including single stranded nucleic acids, generally of viral or bacterial origin, which involves the induction of cytokine expression and release, particularly the interferons, and cell death.

One common 3' end modification is the addition of a poly A tract comprising one or more (and typically 5-200) adenine (A) residues. The poly A tract can be contained in the nucleic acid sequence encoding the gRNA, or can be added to the gRNA during chemical synthesis, or following in vitro transcription using a polyadenosine polymerase (e.g., *E. coli* Poly(A)Polymerase). In vivo, poly-A tracts can be added to sequences transcribed from DNA vectors through the use of polyadenylation signals. Examples of such signals are provided in Maeder.

RNA-Guided Nucleases

RNA-guided nucleases according to the present disclosure include, without limitation, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity).

Turning to the PAM sequence, this structure takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 5' of the protospacer as visualized relative to the top or complementary strand.

In addition to recognizing specific sequential orientations of PAMs and protospacers, RNA-guided nucleases generally recognize specific PAM sequences. *S. aureus* Cas9, for example, recognizes a PAM sequence of NNGRRT, wherein the N sequences are immediately 3' of the region recognized by the gRNA targeting domain. *S. pyogenes* Cas9 recognizes NGG PAM sequences. It should also be noted that engineered RNA-guided nucleases can have PAM specificities that differ from the PAM specificities of similar nucleases (such as the naturally occurring variant from which an RNA-guided nuclease is derived, or the naturally occurring variant having the greatest amino acid sequence homology to an engineered RNA-guided nuclease). Modified Cas9s that recognize alternate PAM sequences are described below.

RNA-guided nucleases are also characterized by their DNA cleavage activity: naturally-occurring RNA-guided nucleases typically form DSBs in target nucleic acids, but engineered variants have been produced that generate only SSBs (discussed above; see also Ran 2013, incorporated by reference herein), or that do not cut at all.

Cas9

Crystal structures have been determined for *S. pyogenes* Cas9 (Jinek 2014), and for *S. aureus* Cas9 in complex with a unimolecular gRNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in *s. pyogenes* and *s. aureus*). The HNH domain, meanwhile, is structurally similar to HNH endonuclease motifs, and cleaves the complementary (i.e., top) strand of the target nucleic acid. The PI domain contributes to PAM specificity.

Modifications of RNA-Guided Nucleases

The RNA-guided nucleases described above have activities and properties that are useful in a variety of applications, but the skilled artisan will appreciate that RNA-guided nucleases may also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary strand, while inactivation of a Cas9 HNH domain results in a nickase that cleaves the non-complementary strand.

Modifications of PAM specificity relative to naturally occurring Cas9 reference molecules has been described for both *S. pyogenes* (Kleinstiver 2015a) and *S. aureus* (Kleinstiver 2015b). Modifications that improve the targeting fidelity of Cas9 have also been described (Kleinstiver 2016). Each of these references is incorporated by reference herein.

RNA-guided nucleases have been split into two or more parts (see, e.g., Zetsche 2015; Fine 2015; both incorporated by reference).

RNA-guided nucleases are, in some cases, size-optimized or truncated, for example via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. RNA-guided nucleases also optionally include a tag, such as a nuclear localization signal to facilitate movement of RNA-guided nuclease protein into the nucleus.

The foregoing list of modifications is intended to be exemplary in nature, and the skilled artisan will appreciate that other modifications may be possible or desirable in certain applications. For brevity, therefore, certain systems, methods and compositions of the present disclosure are exemplified by reference to particular RNA-guided nucleases, but it should be understood that the RNA-guided nucleases used may be modified in ways that do not alter the exemplified operating principles. Such modifications are within the scope of the present disclosure.

EXAMPLES

The following Examples are illustrative and are not intended to limit the scope or content of the invention in any way.

Example 1: AAV Transduction of Genome Editing Systems in Mouse Retinal Explants

Figure 4A:
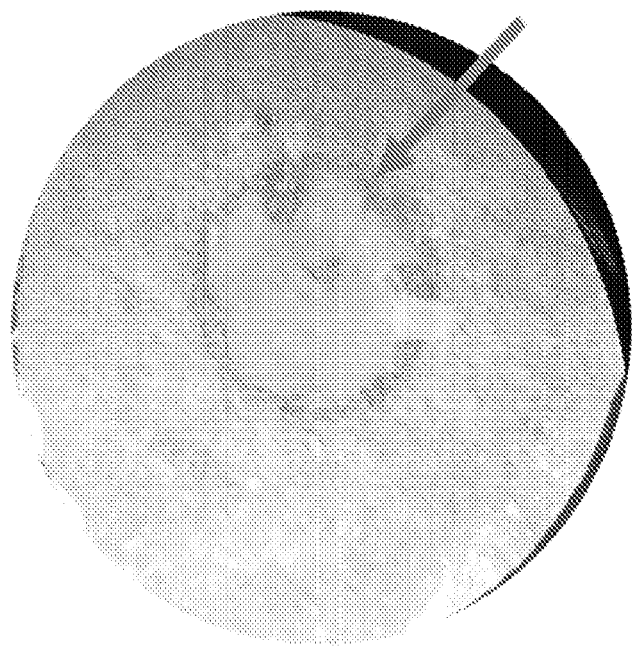
FIG. 4A shows a photomicrograph of a mouse retinal explant on a support matrix; retinal tissue is indicated by the arrow.
Figure 4B:
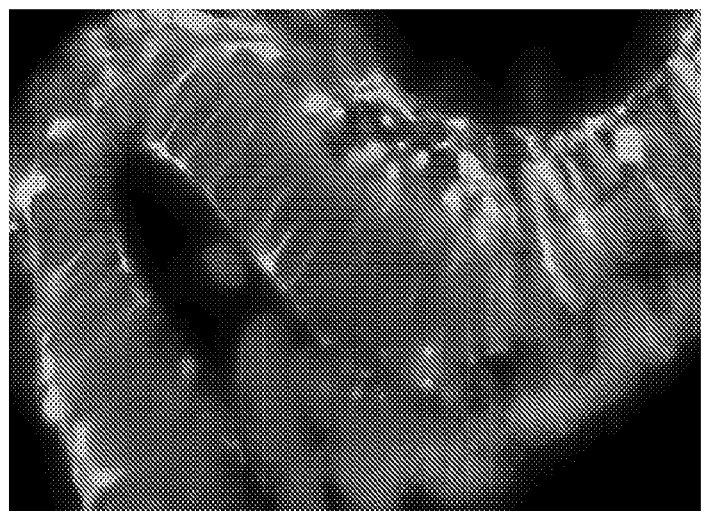
FIG. 4B shows a fluorescence micrograph from a histological section of a mouse retinal explant illustrating AAV transduction of cells in multiple retinal layers with a GFP reporter.
Figure 5A:
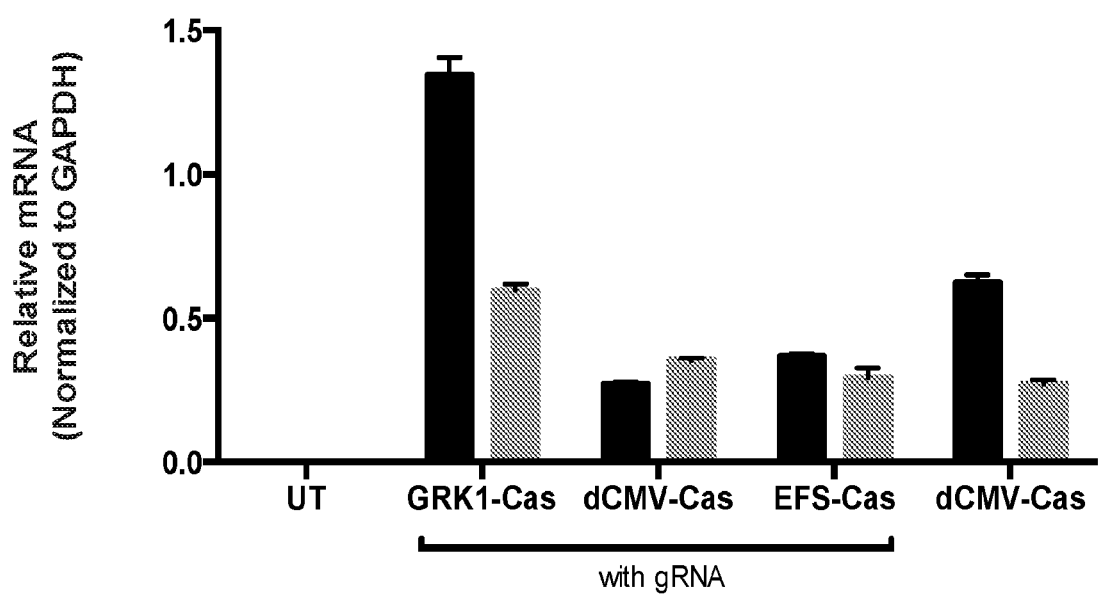
FIG. 5A and FIG. 5B show expression of Cas9 mRNA and gRNA, respectively, normalized to GAPDH mRNA expression. UT denotes untreated; GRK1-Cas refers to a vector in which Cas9 expression is driven by the photoreceptor-specific hGRK1 promoter; dCMV-Cas and EFS-Cas similarly refer to vectors in which Cas9 expression is driven by the dCMV promoter or the EFS promoter. Conditions in which gRNAs are included in the vector are denoted by the bar captioned "with gRNA." Light and dark bars depict separate experimental replicates.
Figure 5B:
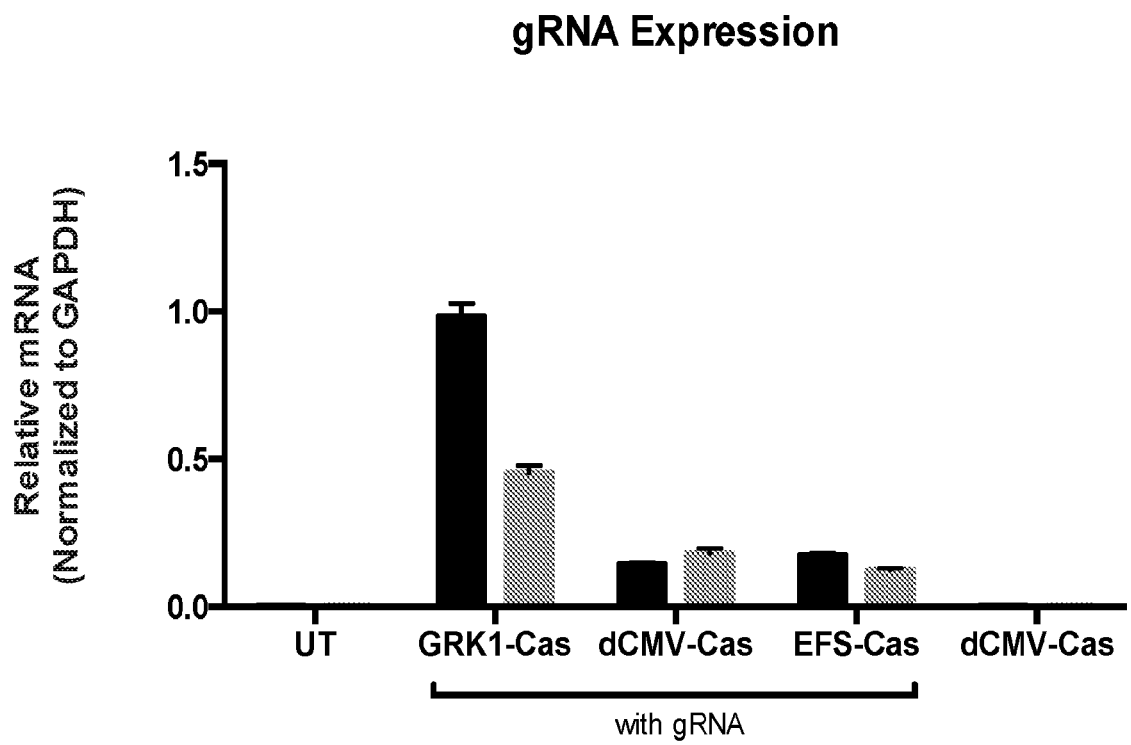

To assess the ability of the AAV vectors described above to transduce CRISPR/Cas9 genome editing systems into retinal cells in situ, an ex vivo explant system was developed. FIG. 4A shows a representative image of an explanted mouse retina on a support matrix, with the tissue indicated by the gray arrow. Explants were harvested at 7- or 10-day time points, and histological, DNA, RNA and/or protein samples were produced. FIG. 4B shows a representative fluorescence micrograph from a retinal explant treated with an AAV vector carrying a GFP reporter, demonstrating successful transduction of an AAV payload in cells in multiple layers of the retina.

mRNA samples taken from retinal explants further demonstrate that genome editing systems according to the present disclosure are effectively transduced by these AAV vectors: FIG. 5A and FIG. 5B show expression of Cas9 mRNA and gRNA, respectively, normalized to the expression of GAPDH. As expected, untreated samples did not express Cas9 or gRNA, and gRNA was not detected in samples that were not transduced with gRNA coding sequences. Cas9 expression was observed in three AAV constructs in which Cas9 expression was driven by hGRK1, CMV or EFS promoters. The observation of Cas9 mRNA and gRNA in samples transduced with vectors in which Cas9 expression is driven by the retinal photoreceptor cell specific hGRK1 promoter indicates that these vectors can transduce genome editing systems in photoreceptor cells in situ.

DNA samples from retinal explants treated with AAV vectors were sequenced, and indel species were identified. The AAV vectors used in the mouse explant system included guides with targeting domains specific to the mouse CEP290 gene but targeted to the same region of intron 26 as the human guides presented above; aside from the specific guide sequences used, the AAV vectors used were the same as those described above. Table 7 shows a wild type (WT) mouse sequence, with left and right guide sequences italicized, and three representative indels of +1, −4 and −246 aligned with the WT sequence. In the table, three periods ( . . . ) represent an abbreviation of the sequence read for ease of presentation, while dashes (-) represent alignment gaps and underlined nucleotides represent insertions. Insofar as DNA sequencing of explants treated with AAV vectors utilizing the photoreceptor specific hGRK1 promoter revealed indel formation, these data demonstrate genome editing of a CEP290 target site in retinal photoreceptors.

TABLE 7

Representative Indels in Mouse Retinal Explants

| | | |
|---|---|---|
| WT | CCCTCAAACACATGTCTCACGCAGCTTAGACATTCT . . . CATGCTACAGATAGCTTATCT | CAGAACTCGGTCAG- |
| | (SEQ ID NO: 18) | (SEQ ID NO: 19) |
| +1 | CCCTCAAACACATGTCTCACGCAGCTTAGACATTCT . . . T | CAGAACTCGGTCAGGCATGCTACAGATAGCTTATC |
| | (SEQ ID NO: 18) | (SEQ ID NO: 34) |

TABLE 7-continued

Representative Indels in Mouse Retinal Explants

```
-4    CCCTCAAACACATGTCTCACGCAGCTTAGACATTCT . . . CAGAACTCGG-----
      CATGCTACAGATAGCTTATCT
            (SEQ ID NO: 18)                        (SEQ ID NO: 35)

-246  CCCTCAAAG-------------------------- . . . ---------------
      CATGCTACAGATAGCTTATCT
            (SEQ ID NO: 36)                        (SEQ ID NO: 37)
```

Figure 6:
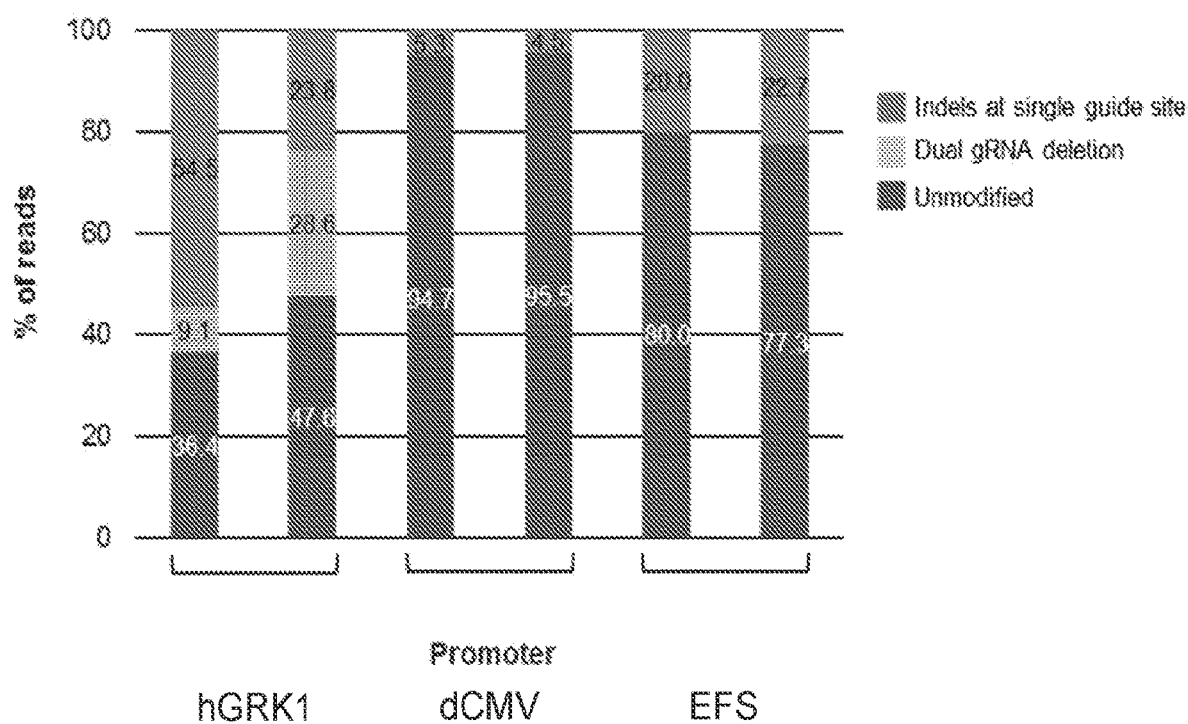
FIG. 6 summarizes the edits observed in mouse retinal explants 7 days after transduction with AAV5-mCEPgR-NAs-Cas9. Edits were binned into one of three categories: no edit, indel at one of two guide sites, and deletion of sequence between the guide sites. Each bar graph depicts the observed edits as a percentage of sequence reads from individual explants transduced with AAV vectors in which Cas9 was driven by the promoter listed (hGRK1, CMV or EFS).

FIG. 6 summarizes the estimated frequencies of particular editing events in individual mouse explants transduced with AAV vectors according to the present disclosure. In samples transduced with AAV vectors in which Cas9 expression was driven by the hGRK1 promoter, deletions of sequences between gRNAs (guide sites) were consistently observed, as were indels at one of the two guide sites. Indels at one of the two guide sites were also observed in explants transduced with CMV and EFS vectors.

Taken together, these results demonstrate the transduction of CRISPR/Cas9 genome editing systems into cells, including photoreceptor cells, in the intact mouse retina and the editing (including deletion) of a CEP290 target site in retinal photoreceptors in situ.

Example 2: AAV Transduction of Genome Editing Systems in Primate Retina In Vivo

To assess the ability of the AAV vectors described above to transduce CRISPR/Cas9 genome editing systems into retinal cells in vivo, a primate subretinal injection procedure was developed. Cynomolgus macaques received a bilateral subretinal injections of an AAV5 vector encoding S. aureus Cas9 operably linked to an EFS, CMV or hGRK promoter sequence, and gRNAs C1 and C2, targeted to an intronic region of the cynomolgus CEP290 gene and comprising targeting sequences as set forth in Table 8. AAV injections were given at dosages of $4\times10^{10}$ (low) or $4\times10^{11}$ (high) viral genomes (vg). Experimental conditions are summarized in Table 9.

TABLE 8

Cynomolgus gRNA Targeting Domain Sequences

| gRNA | Targeting Domain Sequence (DNA) | Targeting Domain Sequence (RNA) |
|---|---|---|
| C1 | GGCCGGCTAATTTAGTAGAGA (SEQ ID NO: 20) | GGCCGGCUAAUUUAGUAGAGA (SEQ ID NO: 38) |
| C2 | GTTATGAAGAATAATACAAA (SEQ ID NO: 21) | GUUAUGAAGAAUAAUACAAA (SEQ ID NO: 39) |

TABLE 9

Cynomolgus Treatment Conditions

| Group | Vector | Dose (vg/eye) |
|---|---|---|
| CMV-low | CEPgRNAs-dCMV-Cas9 | $4 \times 10^{10}$ |
| CMV-high | CEPgRNAs-dCMV-Cas9 | $4 \times 10^{11}$ |
| EFS-low | CEPgRNAs-EFS-Cas9 | $4 \times 10^{10}$ |
| EFS-high | CEPgRNAs-EFS-Cas9 | $4 \times 10^{11}$ |
| GRK-low | CEPgRNAs-GRK1-Cas9 | $4 \times 10^{10}$ |
| GRK-high | CEPgRNAs-GRK1-Cas9 | $4 \times 10^{11}$ |
| Vehicle | GRK1-GFP/Vehicle | $4 \times 10^{11}$ |

6 or 8 mm retinal tissue punches were obtained from AAV-treated and Vehicle-treated retinas at 6 and 13 weeks post injection, and genomic DNA was harvested. Sequencing was performed by using a proprietary methodology (Uni-Directional Targeted Sequencing, or UDiTaS) described in commonly assigned, U.S. Provisional Patent Application No. 62/443,212, which is incorporated by reference herein in its entirety. Data from two UDiTaS sequencing reactions with individual upstream or downstream primers was combined by assuming complete overlap of indels at the two different gRNA cut sites and by averaging the rates of inversions and deletions observed in the two sequencing reactions.

Figure 4C:
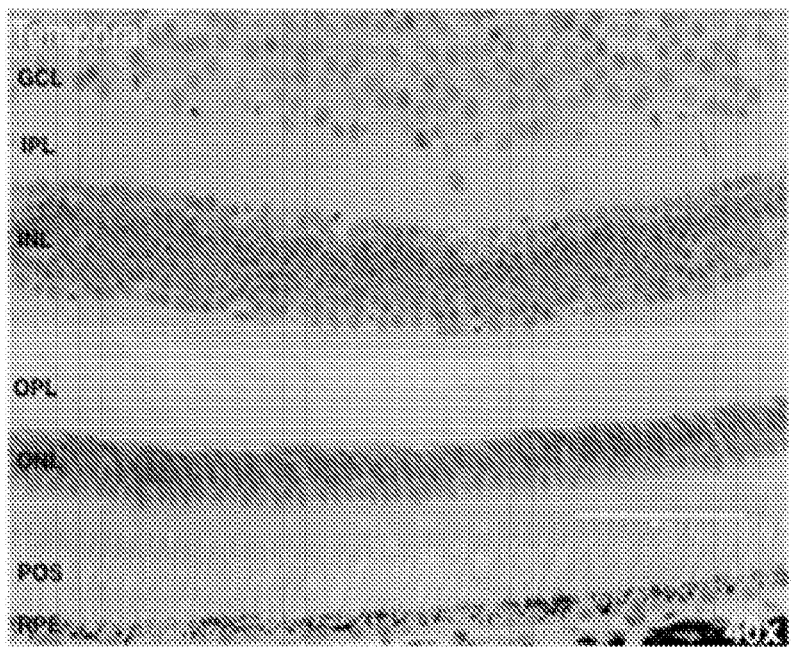
FIG. 4C shows a micrograph from a histological section of a primate retinal tissue treated with vehicle.
Figure 4D:
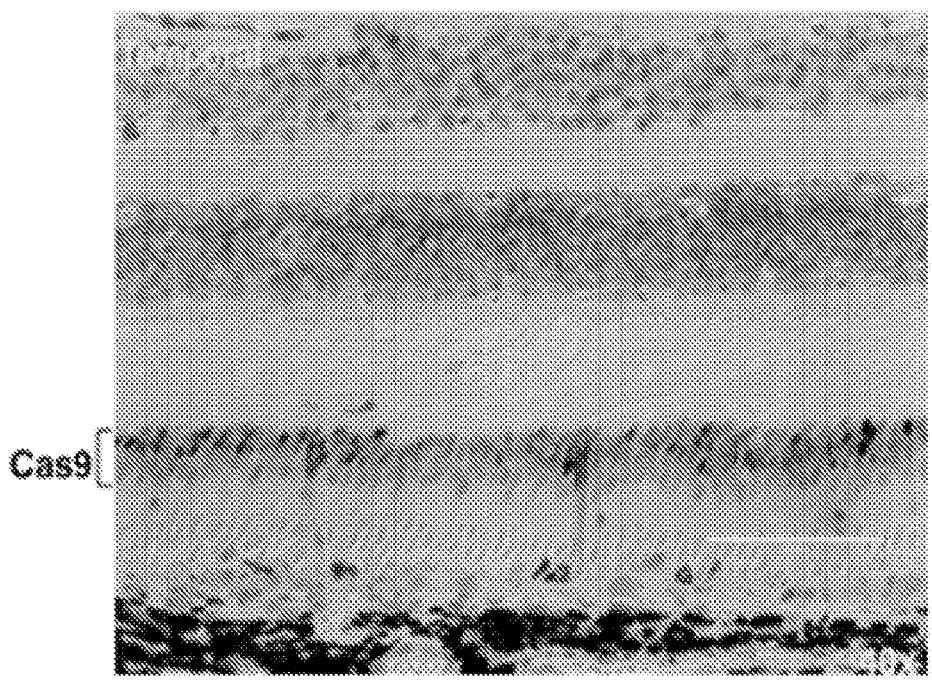
FIG. 4D shows a micrograph from a histological section of a primate retinal tissue treated with AAV5 vector encoding *S. aureus* Cas9 operably linked to the photoreceptor-specific hGRK1 promoter. Dark staining in the outer nuclear layer (ONL) indicates that cells were successfully transduced with AAV and express Cas9.

Histological analysis demonstrated successful transduction of primate photoreceptor cells using genome editing systems as disclosed herein. FIG. 4C depicts Cas9 antibody staining in a vehicle-control tissue punch from a primate retina, while FIG. 4D shows Cas9 expression in a punch from a primate retina treated with an AAV5 vector encoding S. aureus Cas9 operably linked to an hGRK promoter sequence. The figures show that the outer nuclear layer (ONL) in the AAV5 vector-treated punch contains Cas9 protein, while the ONL from the vehicle control punch does not. This demonstrates successful transduction of cells in this layer. No detectable Cas9 expression was detected in cells outside the ONL. Because the hGRK promoter is photoreceptor specific, these data indicate that the systems and methods of this disclosure result in Cas9 expression among retinal photoreceptor cells in primates.

Figure 7:
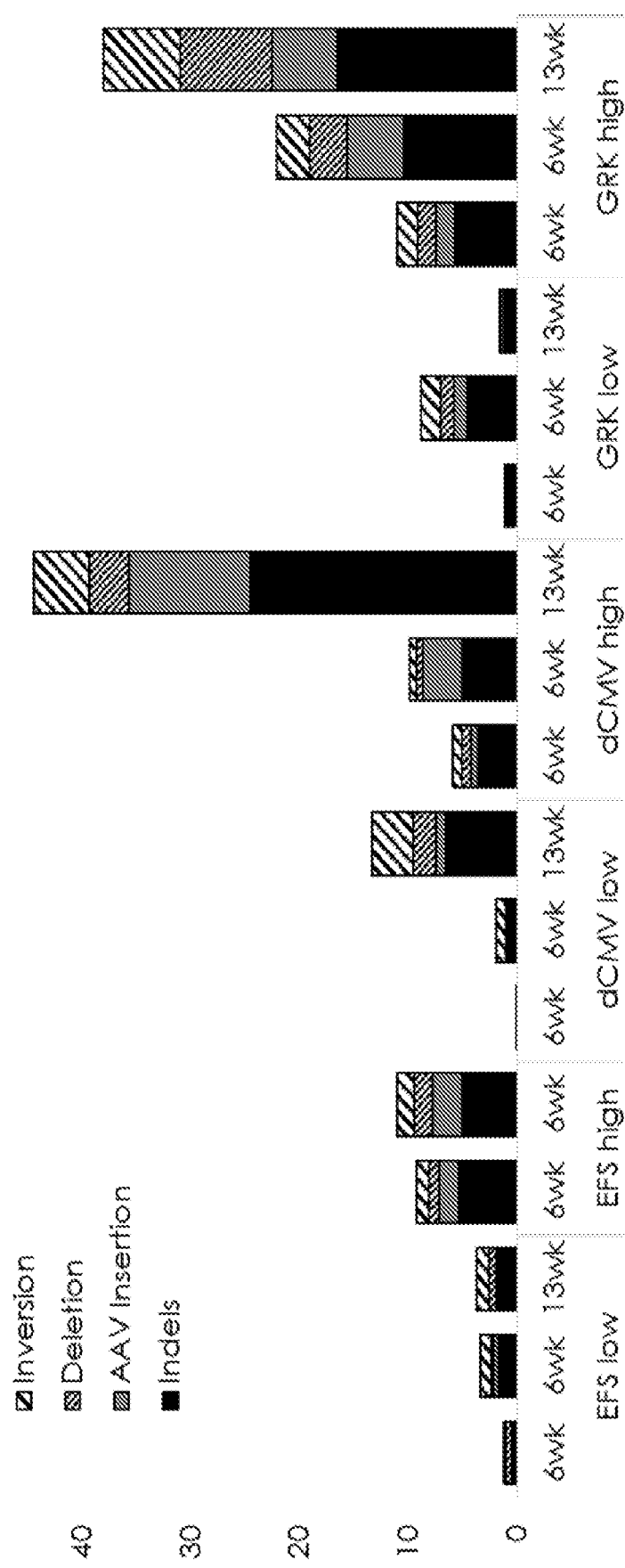
FIG. 7 summarizes the edits observed in the CEP290 gene in retinal punch samples obtained from cynomolgus monkeys treated with AAV vectors encoding genome editing systems according to the present disclosure.

FIG. 7 shows the frequency with which specific edits (indels, insertions, deletions and inversions, were observed in each condition. In both the CMV-high and GRK-high conditions, the frequency of editing events approached or exceeded 40% of reads at the 13-week timepoints. Frequencies of specific edits observed in each experimental condition at each timepoint are listed in Table 10, below. 13 weeks timepoints for the EFS-high condition were not obtained.

TABLE 10

Editing Frequencies Observed in Cynomolgus Treatment Conditions at 6 and 13 Weeks

| | | Total editing | Inversions | Deletions | Insertions | Indels |
|---|---|---|---|---|---|---|
| EFS-low | 6 week | 2.4% | 0.6% | 0.4% | 0.3% | 1.1% |
| | 13 week | 3.8% | 1.2% | 0.6% | 0.0% | 2.0% |
| EFS-high | 6 week | 10.2% | 1.4% | 1.3% | 2.3% | 5.3% |
| | 13 week | — | — | — | — | — |
| CMV-low | 6 week | 1.1% | 0.5% | 0.0% | 0.1% | 0.5% |
| | 13 week | 13.4% | 3.7% | 2.1% | 0.9% | 6.6% |
| CMV-high | 6 week | 8.0% | 0.7% | 0.7% | 2.1% | 4.4% |
| | 13 week | 44.5% | 5.1% | 3.7% | 11.2% | 24.5% |
| GRK-low | 6 week | 5.0% | 0.9% | 0.7% | 0.7% | 2.7% |
| | 13 week | 1.6% | 0.0% | 0.0% | 0.3% | 1.3% |

TABLE 10-continued

Editing Frequencies Observed in Cynomolgus Treatment Conditions at 6 and 13 Weeks

| | | Total editing | Inversions | Deletions | Insertions | Indels |
|---|---|---|---|---|---|---|
| GRK-high | 6 week | 16.6% | 2.5% | 2.5% | 3.5% | 8.1% |
| | 13 week | 38.0% | 7.0% | 8.5% | 5.9% | 16.7% |

It should be noted that the hGRK1 promoter is photoreceptor specific, and that the genome editing system encoded by the AAV5 vector would only be functional in photoreceptor cells. It is reasonable to conclude, therefore, that the percentages of reads obtained from tissue punches, which include other retinal cell types, are lower than the percentages that would be observed in photoreceptor cells alone. Together, these data demonstrate transduction of a CRISPR/Cas9 system into a primate retina by subretinal injection of AAV, in vivo, and the generation of targeted alterations in a CEP290 gene sequence in primate photoreceptor cells in vivo.

Example 3: Correction of IVS26 Splicing Defect by Inversions and Deletions

Figure 8A:
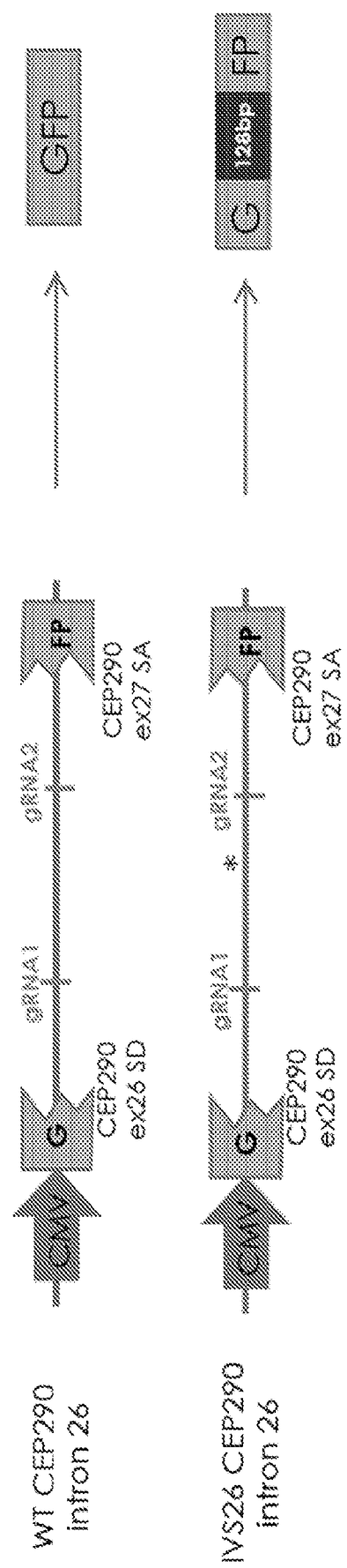
FIG. 8A depicts a reporter construct that was used to assess the effect of certain editing outcomes, including inversions and deletions, on the IVS26 splicing defect.
Figure 8B:
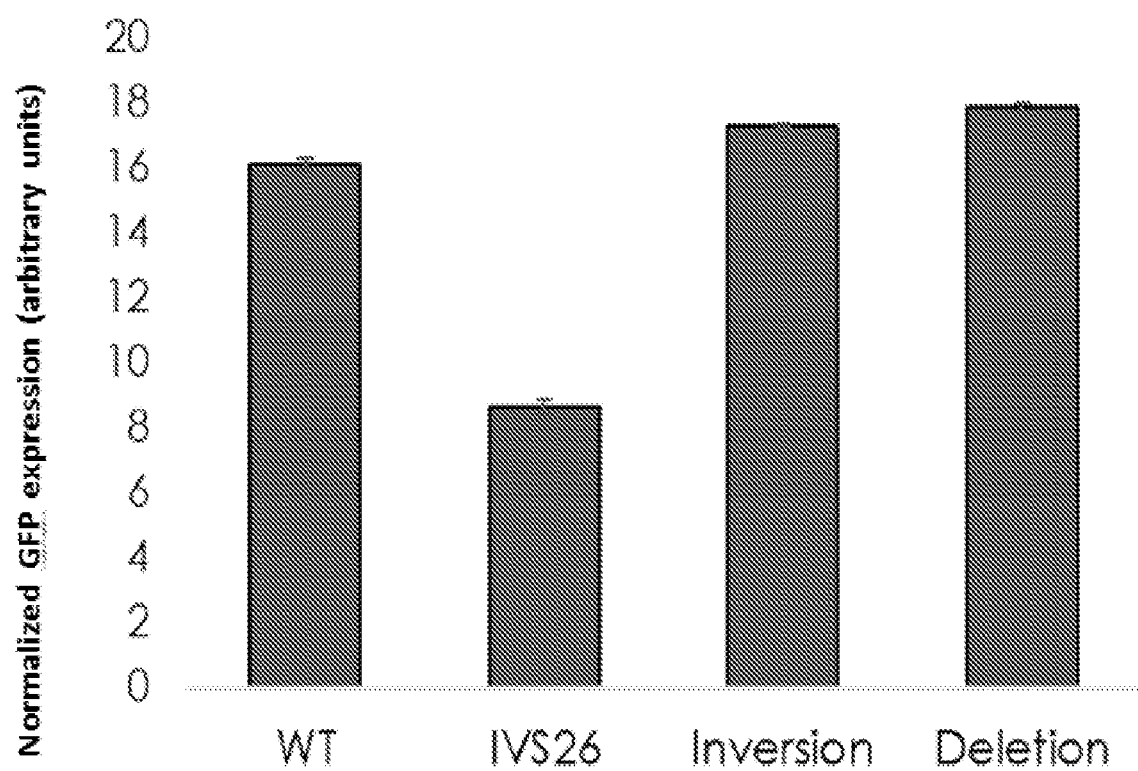
FIG. 8B depicts the relative levels of GFP reporter expression in WT, IVS26, deletion and inversion conditions, normalized to mCherry expression.

To verify that deletions and inversions of the intronic region including the IVS26 mutation correct the splicing defect observed in CEP290 associated disease, a reporter assay was developed utilizing four reporter constructs having the general design depicted in FIG. 8A pAD26_SplitGFP+WildType_CEP290_Kan (SEQ ID NO:22); pAD27_SplitGFP+Mutant_CEP290_Kan (SEQ ID NO:23); pAD28_SplitGFP+Mutant_CEP290_Inverted_Kan (SEQ ID NO:24); and pAD29_SplitGFP+DeletionCEP290_Kan (SEQ ID NO:25). These constructs were transfected into U2OS cells at the concentrations shown in FIG. 8B, and GFP and mCherry expression was quantitated for each condition across three bioreplicates. Each of the four reporter constructs included a sequence encoding a split-green-fluorescent protein (GFP) reporter gene incorporating a 2217 bp human CEP 290 intron sequence corresponding to (a) wild type (WT), (b) the IVS26 mutation, (c) a deletion of the intronic sequence between two human CEP290 target sites, including the IVS26 mutation and the cryptic exon observed in mRNAs from subjects with CEP290 associated disease, as would result from the use of a genome editing system according to the present disclosure, or (d) an inversion of the intronic sequence between the two human CEP290 target sites, including the IVS26 mutation and the cryptic exon as would result from the use of a genome editing system of this disclosure. The construct is designed such that correct splicing is necessary for GFP expression. Thus, the presence of the cryptic splice acceptor site in the IVS26 condition, but not the WT condition, will result in disrupted GFP transcripts encoding non-functional GFP proteins; modifications at CEP290 target sites that result in the removal or alteration of the IVS26 mutation would rescue the expression of functional GFP protein. As shown in FIG. 8B, functional GFP protein is expressed at a high baseline level in cells treated with the WT construct, expression is reduced in the IVS26 condition, and is returned to the WT baseline level in the deletion and inversion conditions. These data indicate that the aberrant mRNA splicing caused by the IVS26 mutation is rescued by either deletion or inversion of the intronic sequence comprising that mutation.

Example 4: AAV5 Transduction of Genome Editing Systems in Human Retinal Explants To further establish that the genome editing systems of the present disclosure supported targeted gene editing in human retinal cells, e.g., fully mature human photoreceptors in situ, an ex vivo human retina explant system was developed. Purified AAV5 vectors were selected that encoded *S. aureus* Cas9 operably linked to an hGRK1 or CMV promoter sequence and first and second gRNAs comprising targeting sequences according to SEQ ID NOS: 1 and 4, respectively, and backbone sequences according to SEQ ID NO: 8. As discussed above, these guides are targeted to the intronic region of the CEP290 gene on opposite sides of the IVS26 A>G mutation (Table 2). Human cadaver donor eyes were obtained within approximately 5 hours post-mortem and 3 mm punches were immobilized on a culture substrate as described above. Retinal explants were treated with AAV vectors at either a low dose of $1\times10^{11}$ vg or a high dose of $5\times10^{11}$ vg. Experimental conditions are summarized in Table 11.

TABLE 11

Human Treatment Conditions

| Group | Vector | Dose (vg/punch) |
|---|---|---|
| CMV-low | CEPgRNAs-dCMV-Cas9 | $1 \times 10^{11}$ |
| CMV-high | CEPgRNAs-dCMV-Cas9 | $5 \times 10^{11}$ |
| GRK-low | CEPgRNAs-GRK1-Cas9 | $1 \times 10^{11}$ |
| GRK-high | CEPgRNAs-GRK1-Cas9 | $5 \times 10^{11}$ |
| Vehicle | GRK1-GFP/Vehicle | $5 \times 10^{11}$ |

Figure 9:
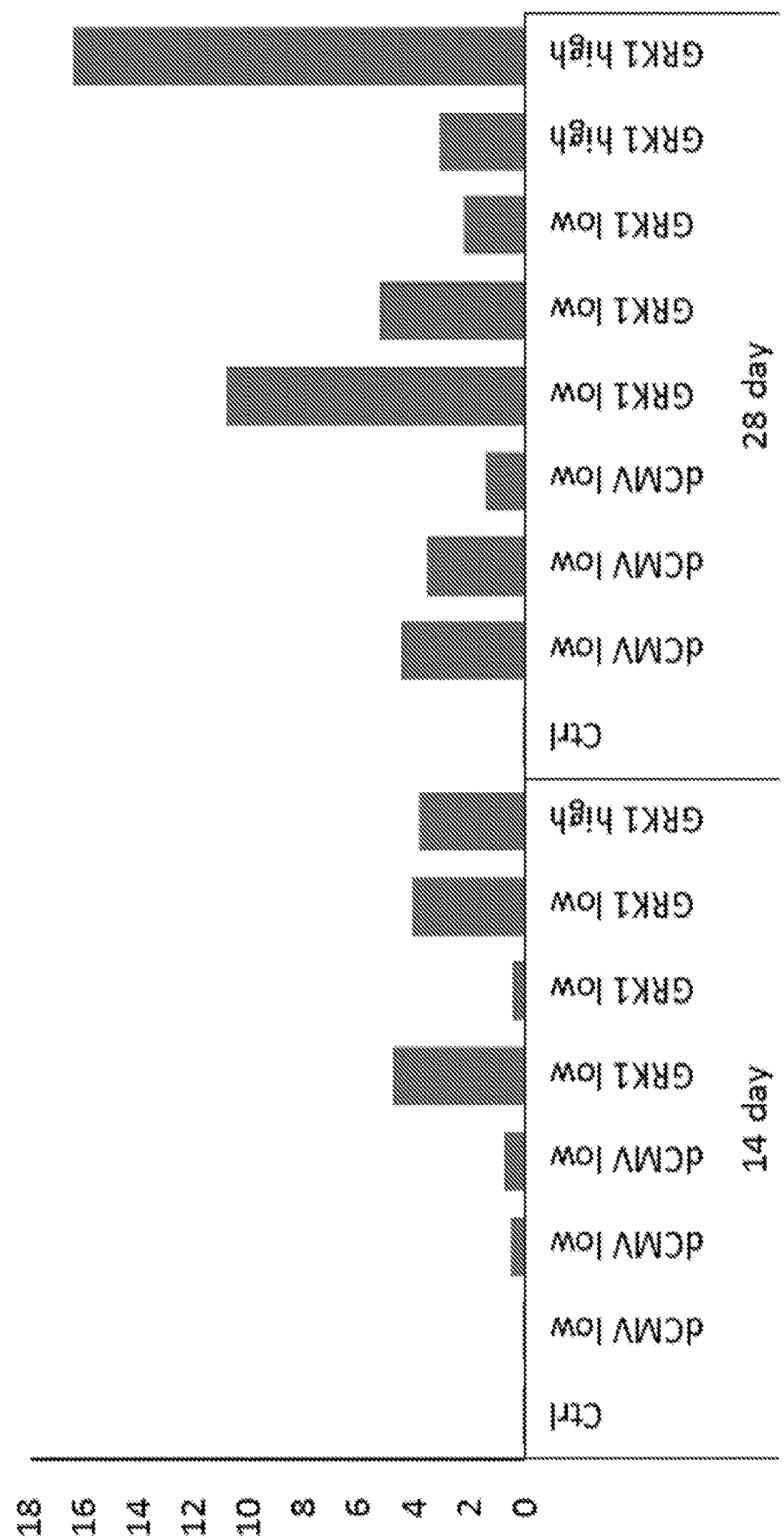
FIG. 9 summarizes the productive CEP290 edits observed in human retinal explants 14 or 28 days after transduction with AAV vectors in which Cas9 was driven by the promoter listed (hGRK1 or CMV).

DNA samples from human retinal explants treated with AAV vectors were sequenced at either 14 or 28 days post-transduction, and inversions and deletions were identified. FIG. 9 summarizes the productive editing observed in human retinal explants 14 and 28 days after transduction with the various AAV vectors. Productive editing was defined as total edits (equal to the sum of the rates of inversions and deletions) capable of correcting the LCA10-associated splice mutation in the CEP290 gene (FIG. 9). The most productive editing was observed at 16.4% at the 28 day time point for the GRK-high condition. These data demonstrate transduction of a CRISPR/Cas9 system into a human retina by subretinal injection of AAV and the generation of targeted alterations in a CEP290 gene sequence in human photoreceptor cells in situ.

Example 5: AAV5 Transduction of Genome Editing Systems in Live Transgenic IVS26 Knock-in Mice To further establish that the genome editing systems of the present disclosure supported targeted gene editing of the human CEP290 target position in mature photoreceptors in vivo, an IVS26 12 KI mouse model was employed. In this model, the human CEP290 exon 26, intron 26 with the IVS26 mutation (13 c.2991+1655A>G) and exon 27 have been inserted into the murine CEP290 gene via homologous recombination. AAV5 vectors encoding (i) *S. aureus* Cas9 operably linked to the photoreceptor-specific hGRK1 promoter sequence, and (ii) first and second gRNAs comprising targeting sequences according to SEQ ID NOS: 1 and 4, respectively, and having gRNA backbone sequences according to SEQ ID NO: 8 were used as described in Example 4. The vectors were administered subretinally (toward the temporal side of the retina near the optic nerve) in both eyes of each animal at doses of 1×10$^{11}$ vg/mL, 1×10$^{12}$ vg/mL or 1×10$^{13}$ vg/mL; a vehicle group (containing BSS with 0.014% Tween20) was also used in the study as a control. Subretinal injections were conducted in anesthetized mice in accordance with NIH animal care guidelines. For each injection, a blunt-ended needle (33-gauge, 0.5 in; Hamilton company) on a 5 ml Hamilton syringe was inserted through the scleral incision, posterior to the lens, and was advanced centrally toward the temporal retina until resistance was felt. Care was taken to avoid the damaging the lens as the cannula was advanced. A volume of 1 microliter of AAV formulation or vehicle control containing 0.2 mg/mL of fluorescein was injected into the subretinal space, forming a bleb; fluorescein was used to visualize the bleb and to confirm successful injection. Animals were euthanized at 6- and 12-week timepoints, and retinal genomic DNA and RNA were isolated for determining the gene editing efficiency (by UDiTaS) and Cas9/gRNA levels (by RT_PCR), respectively.

Experimental conditions are summarized in Table 12, along with rates of insertion and deletion from individual retinas as measured by UDiTaS.

TABLE 12

Inversion and deletion rates in IVS26 KI mouse retinas

|  | Dose | | | |
|---|---|---|---|---|
|  | 1 × 10$^{12}$ vg | | 1 × 10$^{13}$ vg | |
| Timepoint | 6 weeks | 12 weeks | 6 weeks | 12 weeks |
| Inversions | 4.68% | 3.91% | 2.06% | 1.88% |
| Deletions | 6.29% | 5.27% | 7.79% | 4.13% |

These data provide further demonstrate the successful transduction of retinal photoreceptor cells and alteration of the LCA10 target position using the vectors and genome editing systems of the present disclosure.

INCORPORATION BY REFERENCE

All references mentioned herein are hereby incorporated by reference in their entirety as if each individual reference was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Anders et al. Nature 513(7519):569-573 (2014)
Briner et al. Mol Cell 56(2):333-339 (2014)
Cornish-Bowden Nucleic Acids Res 13(9):3021-3030 (1985)
Davis & Maizels Proc Natl Acad Sci USA 111(10):E924-E932 (2014)
Fine et al. Sci Rep 5:10777 (2015)
Frit et al. DNA Repair (Amst.) 17:81-97 (2014)
Hsu et al. Nat Biotechnol 31(9):827-832 (2013)
Iyama & Wilson DNA Repair (Amst.) 12(8):620-636 (2013)
Jiang et al. Nat Biotechnol 31(3):233-239 (2013)
Jinek et al. Science 337(6096):816-821 (2012)
Jinek et al. Science 343(6176):1247997 (2014)
Kleinstiver et al. Nature 523(7561):481-485 (2015a)
Kleinstiver et al. Nat Biotechnol 33(12):1293-1298 (2015b)
Kleinstiver et al. Nature 529(7587):490-495 (2016)
Komor et al. Nature 533(7603):420-424 (2016)
Makarova et al. Nat Rev Microbiol 9(6):467-477 (2011)
Mali et al. Science 339(6121):823-826 (2013)
Nishimasu et al. Cell 156(5):935-949 (2014)
Nishimasu et al. Cell 162(5):1113-1126 (2015)
Ran et al. Cell 154(6):1380-1389 (2013)
Tsai et al. Nat Biotechnol 34(5):483 (2016)
Zetsche et al. Nat Biotechnol 33(2):139-142 (2015)

The invention claimed is:

1. A method of treating a subject, comprising:
   contacting a retina of the subject with one or more recombinant viral vectors comprising one or more nucleic acids encoding a Cas9, a first guide RNA (gRNA) and a second gRNA,
   wherein (a) the first and second gRNAs are adapted to form first and second ribonucleoprotein complexes with the Cas9, and (b) the first and second ribonucleoprotein complexes are adapted to cleave first and second cellular nucleic acid sequences on first and second sides of a CEP290 target position, thereby altering a nucleotide sequence of the CEP290 target position,
   wherein the first cellular nucleic acid sequence is different from the second cellular nucleic acid sequence,
   wherein the one or more recombinant viral vectors contact the retina at a dose of $1 \times 10^{11}$ viral genomes (vg)/mL to $9 \times 10^{13}$ vg/mL.

2. The method of claim 1, wherein the dose is selected from the group consisting of $1 \times 10^{11}$ vg/mL, $2 \times 10^{11}$ vg/mL, $3 \times 10^{11}$ vg/mL, $4 \times 10^{11}$ vg/mL, $5 \times 10^{11}$ vg/mL, $6 \times 10^{11}$ vg/mL, $7 \times 10^{11}$ vg/mL, $8 \times 10^{11}$ vg/mL, $9 \times 10^{11}$ vg/mL, $1 \times 10^{12}$ vg/mL, $2 \times 10^{12}$ vg/mL, $3 \times 10^{12}$ vg/mL, $4 \times 10^{12}$ vg/mL, $5 \times 10^{12}$ vg/mL, $6 \times 10^{12}$ vg/mL, $7 \times 10^{12}$ vg/mL, $8 \times 10^{12}$ vg/mL, $9 \times 10^{12}$ vg/mL, $1 \times 10^{13}$ vg/mL, $2 \times 10^{13}$ vg/mL, $3 \times 10^{13}$ vg/mL, $4 \times 10^{13}$ vg/mL, $5 \times 10^{13}$ vg/mL, $6 \times 10^{13}$ vg/mL, $7 \times 10^{13}$ vg/mL, $8 \times 10^{13}$ vg/mL, and $9 \times 10^{13}$ vg/mL.

3. The method of claim 1, wherein the subject has Leber Congenital Amaurosis-10 (LCA-10).

4. The method of claim 1, wherein the one or more recombinant viral vectors are AAV vectors.

5. The method of claim 4, wherein the AAV vectors are AAV5 vectors.

6. The method of claim 1, wherein
   the first gRNA comprises a targeting domain of SEQ ID NO:1 and the second gRNA comprises a targeting domain of SEQ ID NO:4;
   the first gRNA comprises a targeting domain of SEQ ID NO:2 and the second gRNA comprises a targeting domain of SEQ ID NO:5; or
   the first gRNA comprises a targeting domain of SEQ ID NO:3 and the second gRNA comprises a targeting domain of SEQ ID NO:6.

7. The method of claim 6, wherein the first gRNA comprises a targeting domain of SEQ ID NO:1 and the second gRNA comprises a targeting domain of SEQ ID NO:4.

8. The method of claim 6, wherein the first gRNA comprises a targeting domain of SEQ ID NO:2 and the second gRNA comprises a targeting domain of SEQ ID NO:5.

9. The method of claim 6, wherein the first gRNA comprises a targeting domain of SEQ ID NO:3 and the second gRNA comprises a targeting domain of SEQ ID NO:6.

10. A method of altering a retinal cell, comprising:
    contacting a retina of a subject with one or more recombinant viral vectors comprising one or nucleic acid encoding a Cas9, a first gRNA and a second gRNA, wherein the first gRNA comprises a targeting domain selected from the group consisting of SEQ ID NOS: 1-3 and the second gRNA comprises a targeting domain selected from the group consisting of SEQ ID NOS: 4-6,
    wherein the one or more recombinant viral vectors contact the retina at a dose of $1 \times 10^{11}$ vg/mL to $9 \times 10^{13}$ vg/mL.

11. The method of claim 10, wherein the dose is selected from the group consisting of $1 \times 10^{11}$ vg/mL, $2 \times 10^{11}$ vg/mL, $3 \times 10^{11}$ vg/mL, $4 \times 10^{11}$ vg/mL, $5 \times 10^{11}$ vg/mL, $6 \times 10^{11}$ vg/mL, $7 \times 10^{11}$ vg/mL, $8 \times 10^{11}$ vg/mL, $9 \times 10^{11}$ vg/mL, $1 \times 10^{12}$ vg/mL, $2 \times 10^{12}$ vg/mL, $3 \times 10^{12}$ vg/mL, $4 \times 10^{12}$ vg/mL, $5 \times 10^{12}$ vg/mL, $6 \times 10^{12}$ vg/mL, $7 \times 10^{12}$ vg/mL, $8 \times 10^{12}$ vg/mL, $9 \times 10^{12}$ vg/mL, $1 \times 10^{13}$ vg/mL, $2 \times 10^{13}$ vg/mL, $3 \times 10^{13}$ vg/mL, $4 \times 10^{13}$ vg/mL, $5 \times 10^{13}$ vg/mL, $6 \times 10^{13}$ vg/mL, $7 \times 10^{13}$ vg/mL, $8 \times 10^{13}$ vg/mL, and $9 \times 10^{13}$ vg/mL.

12. The method of claim 10, wherein the one or more recombinant viral vectors are administered to a subretinal space of the retina.

13. The method of claim 10, wherein the subject has Leber Congenital Amaurosis-10 (LCA-10).

14. The method of claim 10, wherein the one or more recombinant viral vectors are AAV vectors.

15. The method of claim 14, wherein the AAV vectors are AAV5 vectors.

16. The method of claim 10, wherein the first gRNA comprises a targeting domain of SEQ ID NO:1 and the second gRNA comprises a targeting domain of SEQ ID NO:4.

17. The method of claim 10, wherein the first gRNA comprises a targeting domain of SEQ ID NO:2 and the second gRNA comprises a targeting domain of SEQ ID NO:5.

18. The method of claim 10, wherein the first gRNA comprises a targeting domain of SEQ ID NO:3 and the second gRNA comprises a targeting domain of SEQ ID NO:6.

19. A method of treating a subject having an inherited retinal dystrophy, comprising:
administering to a retina of the subject with one or more recombinant viral vectors comprising one or more nucleic acids encoding a Cas9 and a first gRNA comprising a sequence having at least 90% sequence identity to a sequence selected from SEQ ID NOS: 7 and 8;
wherein (a) the first gRNA is adapted to form a first ribonucleoprotein complex with the Cas9, and (b) the first ribonucleoprotein complex is adapted to cleave a first cellular nucleic acid sequence associated with the inherited retinal dystrophy, thereby altering the first cellular nucleic acid sequence,
wherein the one or more recombinant viral vectors are administered to the retina at a dose of $1\times10^{11}$ vg/mL to $9\times10^{13}$ vg)/mL.

20. The method of claim 19, wherein the dose is selected from the group consisting of $1\times10^{11}$ vg/mL, $2\times10^{11}$ vg/mL, $3\times10^{11}$ vg/mL, $4\times10^{11}$ vg/mL, $5\times10^{11}$ vg/mL, $6\times10^{11}$ vg/mL, $7\times10^{11}$ vg/mL, $8\times10^{11}$ vg/mL, $9\times10^{11}$ vg/mL, $1\times10^{12}$ vg/mL, $2\times10^{12}$ vg/mL, $3\times10^{12}$ vg/mL, $4\times10^{12}$ vg/mL, $5\times10^{12}$ vg/mL, $6\times10^{12}$ vg/mL, $7\times10^{12}$ vg/mL, $8\times10^{12}$ vg/mL, $9\times10^{12}$ vg/mL, $1\times10^{13}$ vg/mL, $2\times10^{13}$ vg/mL, $3\times10^{13}$ vg/mL, $4\times10^{13}$ vg/mL, $5\times10^{13}$ vg/mL, $6\times10^{13}$ vg/mL, $7\times10^{13}$ vg/mL, $8\times10^{13}$ vg/mL, and $9\times10^{13}$ vg/mL.

21. The method of claim 20, further comprising (a) a second gRNA adapted to form a second ribonucleoprotein complex with the Cas9, and (b) the second ribonucleoprotein complex adapted to cleave a second cellular nucleic acid sequence associated with the inherited retinal dystrophy, thereby altering the second cellular nucleic acid sequence.

22. The method of claim 21, wherein the first gRNA comprises a targeting domain selected from the group consisting of SEQ ID NOS: 1-3 and the second gRNA comprises a targeting domain selected from the group consisting of SEQ ID NOS: 4-6.

23. The method of claim 22, wherein the first gRNA comprises a targeting domain of SEQ ID NO:1 and the second gRNA comprises a targeting domain of SEQ ID NO:4.

24. The method of claim 22, wherein the first gRNA comprises a targeting domain of SEQ ID NO:2 and the second gRNA comprises a targeting domain of SEQ ID NO:5.

25. The method of claim 22, wherein the first gRNA comprises a targeting domain of SEQ ID NO:3 and the second gRNA comprises a targeting domain of SEQ ID NO:6.

26. The method of claim 19, wherein the inherited retinal dystrophy is Leber Congenital Amaurosis-10 (LCA-10).

27. The method of claim 19, wherein the one or more recombinant viral vectors are AAV vectors.

28. The method of claim 27, wherein the AAV vectors are AAV5 vectors.

* * * * *

SEQUENCE LISTING

<160> NUMBER OF SEQ ID NOS: 39

<210> SEQ ID NO 1
<211> LENGTH: 22
<212> TYPE: DNA
<213> ORGANISM: Artificial Sequence
<220> FEATURE:
<223> OTHER INFORMATION: Targeting domain

<400> SEQUENCE: 1
gttctgtcct cagtaaaagg ta                                                22

<210> SEQ ID NO 2
<211> LENGTH: 20
<212> TYPE: DNA
<213> ORGANISM: Artificial Sequence
<220> FEATURE:
<223> OTHER INFORMATION: Targeting domain

<400> SEQUENCE: 2
gaatagtttg ttctgggtac                                                   20

```
<210> SEQ ID NO 3
<211> LENGTH: 20
<212> TYPE: DNA
<213> ORGANISM: Artificial Sequence
<220> FEATURE:
<223> OTHER INFORMATION: Targeting domain

<400> SEQUENCE: 3
gagaaaggga tgggcactta                                                     20

<210> SEQ ID NO 4
<211> LENGTH: 22
<212> TYPE: DNA
<213> ORGANISM: Artificial Sequence
<220> FEATURE:
<223> OTHER INFORMATION: Targeting domain

<400> SEQUENCE: 4
gtcaaaagct accggttacc tg                                                  22

<210> SEQ ID NO 5
<211> LENGTH: 20
<212> TYPE: DNA
<213> ORGANISM: Artificial Sequence
<220> FEATURE:
<223> OTHER INFORMATION: Targeting domain

<400> SEQUENCE: 5
gatgcagaac tagtgtagac                                                     20

<210> SEQ ID NO 6
<211> LENGTH: 19
<212> TYPE: DNA
<213> ORGANISM: Artificial Sequence
<220> FEATURE:
<223> OTHER INFORMATION: Targeting domain

<400> SEQUENCE: 6
gagtatctcc tgtttggca                                                      19

<210> SEQ ID NO 7
<211> LENGTH: 102
<212> TYPE: DNA
<213> ORGANISM: Artificial Sequence
<220> FEATURE:
<223> OTHER INFORMATION: S. aureus gRNA
<220> FEATURE:
<221> NAME/KEY: misc_feature
<222> LOCATION: (1)..(20)
<223> OTHER INFORMATION: Targeting domain of 16-24 nts, each n is a, c,
      t, g, unknown, or other

<400> SEQUENCE: 7
nnnnnnnnnn nnnnnnnnnn gttttagtac tctggaaaca gaatctacta aacaaggca          60 aaatgccgtg tttatctcgt caacttgttg gcgagatttt tt                           102

<210> SEQ ID NO 8
<211> LENGTH: 102
<212> TYPE: DNA
<213> ORGANISM: Artificial Sequence
<220> FEATURE:
<223> OTHER INFORMATION: S. aureus gRNA
<220> FEATURE:
<221> NAME/KEY: misc_feature
<222> LOCATION: (1)..(20)
<223> OTHER INFORMATION: Targeting domain of 16-24 nts, each n is a, c,
      t, g, unknown, or other
```

<400> SEQUENCE: 8

| | | |
|---|---|---|
| nnnnnnnnnn nnnnnnnnnn gttatagtac tctggaaaca gaatctacta taacaaggca | 60 |
| aaatgccgtg tttatctcgt caacttgttg gcgagatttt tt | 102 |

<210> SEQ ID NO 9
<211> LENGTH: 264
<212> TYPE: DNA
<213> ORGANISM: Artificial Sequence
<220> FEATURE:
<223> OTHER INFORMATION: U6 promoter

<400> SEQUENCE: 9

| | |
|---|---|
| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |
| aaaatggact atcatatgct taccgtaact tgaaagtatt tcgatttctt ggctttatat | 240 |
| atcttgtgga aaggacgaaa cacc | 264 |

<210> SEQ ID NO 10
<211> LENGTH: 3159
<212> TYPE: DNA
<213> ORGANISM: Artificial Sequence
<220> FEATURE:
<223> OTHER INFORMATION: Codon optimized S. aureus Cas9

<400> SEQUENCE: 10

| | |
|---|---|
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca tgagggacg gagaagcaag aggggagcca ggcgcctgaa cgacgggaga | 180 |
| aggcacagaa tccagagggt gaagaaactg ctgttcgatt acaacctgct gaccgaccat | 240 |
| tctgagctga gtggaattaa tccttatgaa gccagggtga aggcctgag tcagaagctg | 300 |
| tcagaggaag agttttccgc agctctgctg cacctggcta agcgccgagg agtgcataac | 360 |
| gtcaatgagt ggaagagga caccggcaac gagctgtcta caaaggaaca gatctcacgc | 420 |
| aatagcaaag ctctggaaga gaagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca aaggcttac caccagctgg atcagagctt catcgatact | 600 |
| tatatcgacc tgctggagac tcggagaacc tactatgagg gaccaggaga agggagcccc | 660 |
| ttcggatgga aagacatcaa ggaatggtac gagatgctga tgggacattg cacctatttt | 720 |
| ccagaagagc tgagaagcgt caagtacgct tataacgcag atctgtacaa cgcccctgaat | 780 |
| gacctgaaca acctggtcat caccagggat gaaaacgaga actggaata ctatgagaag | 840 |
| ttccagatca tcgaaaacgt gtttaagcag aagaaaagc ctacactgaa acagattgct | 900 |
| aaggagatcc tggtcaacga agaggacatc aagggctacc gggtgacaag cactggaaaa | 960 |
| ccagagttca ccaatctgaa agtgtatcac gatattaagg acatcacagc acggaaagaa | 1020 |
| atcattgaga cgccgaact gctggatcag attgctaaga tcctgactat ctaccagagc | 1080 |
| tccgaggaca tccaggaaga gctgactaac ctgaacagcg agctgaccca ggaagagatc | 1140 |
| gaacagatta gtaatctgaa ggggtacacc ggaacacaca acctgtccct gaaagctatc | 1200 |
| aatctgattc tggatgagct gtggcataca acgacaatc agattgcaat ctttaaccgg | 1260 |
| ctgaagctgg tcccaaaaaa ggtggacctg agtcagcaga aagagatccc aaccacactg | 1320 |

```
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620 atcccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
tctaaaaagg gcaataggac tcctttccag tacctgtcta gttcagattc caagatctct   1800
tacgaaacct ttaaaaagca cattctgaat ctggccaaag gaagggccg catcagcaag   1860 accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca gtccatcaa cggcgggttc   2040 acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaatacccttg   2400 attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
aagtactatg gaacaagct gaatgcccat ctggacatca cagacgatta ccctaacagt   2700
cgcaacaagg tggtcaagct gtcactgaag ccatacagat cgatgtcta tctggacaac   2760 ggcgtgtata aatttgtgac tgtcaagaat ctggatgtca tcaaaaagga gaactactat   2820
gaagtgaata gcaagtgcta cgaagaggct aaaaagctga aaagattagc aaccaggca   2880 gagttcatcg cctcctttta caacaacgac ctgattaaga tcaatggcga actgtatagg   2940
gtcatcgggg tgaacaatga tctgctgaac cgcattgaag tgaatatgat tgacatcact   3000
taccgagagt atctggaaaa catgaatgat aagcgcccc ctcgaattat caaaacaatt   3060
gcctctaaga ctcagagtat caaaaagtac tcaaccgaca ttctgggaaa cctgtatgag   3120
gtgaagagca aaaagcaccc tcagattatc aaaaagggc                         3159
```

<210> SEQ ID NO 11
<211> LENGTH: 1053
<212> TYPE: PRT
<213> ORGANISM: Staphylococcus aureus

<400> SEQUENCE: 11

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

```
Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
 65                  70                  75                  80

Ser Glu Leu Ser Gly Ile Asn Pro Tyr Glu Ala Arg Val Lys Gly Leu
                 85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
            130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
            290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
            370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
450                 455                 460
```

```
Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Arg Thr Thr
        500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
            530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880
```

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val
    915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 12
<211> LENGTH: 60
<212> TYPE: DNA
<213> ORGANISM: Artificial Sequence
<220> FEATURE:
<223> OTHER INFORMATION: Polyadenylation signal

<400> SEQUENCE: 12
tagcaataaa ggatcgttta ttttcattgg aagcgtgtgt tggttttttg atcaggcgcg    60

<210> SEQ ID NO 13
<211> LENGTH: 617
<212> TYPE: DNA
<213> ORGANISM: Artificial Sequence
<220> FEATURE:
<223> OTHER INFORMATION: CMV promoter

<400> SEQUENCE: 13
cattgattat tgactagtta ttaatagtaa tcaattacgg ggtcattagt tcatagccca    60
tatatggagt tccgcgttac ataacttacg gtaaatggcc cgcctggctg accgcccaac   120
gacccccgcc cattgacgtc aataatgacg tatgttccca tagtaacgcc aatagggact   180
ttccattgac gtcaatgggt ggactattta cggtaaactg cccacttggc agtacatcaa   240
gtgtatcata tgccaagtac gccccctatt gacgtcaatg acggtaaatg gcccgcctgg   300
cattatgccc agtacatgac cttatgggac tttcctactt ggcagtacat ctacgtatta   360
gtcatcgcta ttaccatggt gatgcggttt tggcagtaca tcaatgggcg tggatagcgg   420
tttgactcac ggggatttcc aagtctccac cccattgacg tcaatgggag tttgttttgg   480
caccaaaatc aacgggactt tccaaaatgt cgtaacaact ccgccccatt gacgcaaatg   540
ggcggtaggc gtgtacggtg ggaggtctat ataagcagag ctggtttagt gaaccgtcag   600
atccgctaga gatccgc                                                  617

```
<210> SEQ ID NO 14
<211> LENGTH: 252
<212> TYPE: DNA
<213> ORGANISM: Artificial Sequence
<220> FEATURE:
<223> OTHER INFORMATION: EFS promoter

<400> SEQUENCE: 14
tcgagtggct ccggtgcccg tcagtgggca gagcgcacat cgcccacagt ccccgagaag     60 ttgggggggag gggtcggcaa ttgaaccggt gcctagagaa ggtggcgcgg ggtaaactgg   120
gaaagtgatg tcgtgtactg gctccgcctt tttcccgagg gtgggggaga accgtatata   180
agtgcagtag tcgccgtgaa cgttcttttt cgcaacgggt ttgccgccag aacacaggtg   240
tcgtgaccgc gg                                                       252

<210> SEQ ID NO 15
<211> LENGTH: 292
<212> TYPE: DNA
<213> ORGANISM: Homo sapiens

<400> SEQUENCE: 15
gggccccaga agcctggtgg ttgtttgtcc ttctcagggg aaaagtgagg cggccccttg     60
gaggaagggg ccgggcagaa tgatctaatc ggattccaag cagctcaggg gattgtcttt   120
ttctagcacc ttcttgccac tcctaagcgt cctccgtgac cccggctggg atttcgcctg   180
gtgctgtgtc agccccggtc tcccaggggc ttcccagtgg tccccaggaa ccctcgacag   240
ggcccggtct ctctcgtcca gcaagggcag ggacgggcca caggccaagg gc          292

<210> SEQ ID NO 16
<211> LENGTH: 145
<212> TYPE: DNA
<213> ORGANISM: Artificial Sequence
<220> FEATURE:
<223> OTHER INFORMATION: AAV2 left ITR sequence

<400> SEQUENCE: 16
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcct                                         145

<210> SEQ ID NO 17
<211> LENGTH: 145
<212> TYPE: DNA
<213> ORGANISM: Artificial Sequence
<220> FEATURE:
<223> OTHER INFORMATION: AAV2 right ITR sequence

<400> SEQUENCE: 17
aggaacccct agtgatggag ttggccactc cctctctgcg cgctcgctcg ctcactgagg     60
ccgcccgggc aaagcccggg cgtcgggcga cctttggtcg cccggcctca gtgagcgagc   120
gagcgcgcag agagggagtg gccaa                                         145

<210> SEQ ID NO 18
<211> LENGTH: 36
<212> TYPE: DNA
<213> ORGANISM: Mus musculus

<400> SEQUENCE: 18
ccctcaaaca catgtctcac gcagcttaga cattct                              36
```

<210> SEQ ID NO 19
<211> LENGTH: 35
<212> TYPE: DNA
<213> ORGANISM: Mus musculus

<400> SEQUENCE: 19
cagaactcgg tcagcatgct acagatagct tatct          35

<210> SEQ ID NO 20
<211> LENGTH: 21
<212> TYPE: DNA
<213> ORGANISM: Artificial Sequence
<220> FEATURE:
<223> OTHER INFORMATION: C1 targeting domain

<400> SEQUENCE: 20
ggccggctaa tttagtagag a          21

<210> SEQ ID NO 21
<211> LENGTH: 20
<212> TYPE: DNA
<213> ORGANISM: Artificial Sequence
<220> FEATURE:
<223> OTHER INFORMATION: C2 targeting domain

<400> SEQUENCE: 21
gttatgaaga ataatacaaa          20

<210> SEQ ID NO 22
<211> LENGTH: 5120
<212> TYPE: DNA
<213> ORGANISM: Artificial Sequence
<220> FEATURE:
<223> OTHER INFORMATION: Reporter construct
      pAD26/SplitGFP+WildType/CEP290/Kan

<400> SEQUENCE: 22
acataactta cggtaaatgg cccgcctggc tgaccgccca acgaccccg cccattgacg     60 tcaataatga cgtatgttcc catagtaacg ccaataggga cttttccattg acgtcaatgg   120 gtggactatt tacggtaaac tgcccacttg gcagtacatc aagtgtatca tatgccaagt   180 acgccccta ttgacgtcaa tgacggtaaa tggcccgcct ggcattatgc ccagtacatg    240
accttatggg actttcctac ttggcagtac atctacgtat tagtcatcgc tattaccatg   300
gtgatgcggt tttggcagta catcaatggg cgtggatagc ggtttgactc acggggattt   360
ccaagtctcc accccattga cgtcaatggg agtttgtttt ggcaccaaaa tcaacgggac   420
tttccaaaat gtcgtaacaa ctccgcccca ttgacgcaaa tgggcggtag gcgtgtacgg   480
tgggaggtct atataagcag agctggttta gtgaaccgtc agatccgcta gagatccgcg   540
gccgctaata cgactcacta tagggagagc cgccaccatg gtgagcaagg gcgaggagct   600
gttcaccggg gtggtgccca tcctggtcga gctggacggc gacgtaaacg ccacaagtt    660 cagcgtgtcc ggcgagggcg agggcgatgc cacctacggc aagctgaccc tgaagttcat   720
ctgcaccacc ggcaagctgc ccgtgccctg gcccaccctc gtgaccaccc tgacctacgg   780
aggtaagttt gtgtgattct tgaaccttgt gaaattagca ttttcttc aatatttttg     840 tgtttggggg gatttggcag attttaatta agtttgcct gcatttatat aaatttaaca    900
gagatataat tatccatatt attcattgtg gctgaatgac ttctgaatga ttatctagat   960
cattctcctt aggtcacttg catgatttag ctgaatcaaa cctcttttaa ccagacatct  1020

```
aagagaaaaa ggagcatgaa acaggtagaa tattgtaatc aaaggaggga agcactcatt   1080
aagtgcccat ccctttctct taccectgta cccagaacaa actattctcc catggtccct   1140
ggcttttgtt ccttggaatg gatgtagcca acagtagctg aaatattaag ggctcttcct   1200
ggaccatgga tgcactctgt aaattctcat catttttat tgtagaataa atgtagaatt    1260
ttaatgtaga ataaatttat ttaatgtaga ataaaaata aaaaaactag agtagaatat    1320
cataagttac aatctgtgaa tatggaccag acccttgta gttatcttac agccacttga    1380
actctatacc ttttactgag gacagaacaa gctcctgatt tgttcatctt cctcatcaga   1440
aatagaggct tatggatttt ggattattct tatctaagat cctttcacag gagtagaata   1500
agatctaatt ctattagctc aaaagctttt gctggctcat agagacacat tcagtaaatg   1560
aaaacgttgt tctgagtagc tttcaggatt cctactaaat tatgagtcat gtttatcaat   1620
attatttaga agtaatcata atcagtttgc tttctgctgc ttttgccaaa gagaggtgat   1680
tatgttactt tttatagaaa attatgccta tttagtgtgg tgataattta ttttttttcca  1740 ttctccatgt cctctgtcct atcctctcca gcattagaaa gtcctaggca agagacatct   1800
tgtggataat gtatcaatga gtgatgttta acgttatcat ttttcccaaag agtattttttc 1860 atctttccta aagatttttt ttttttttt ttgagatgga gtttcattct gtcacccagg    1920
ctgagtgcag tggcacgatc tcggcttaac gcttactgca tcctctgcct cccagattca   1980
agcagttctc ctgcctcagc ctctgagtag ctgggattac aggtgtgcac caccacacca   2040 gctaatttt tttttttttt tttttttttt gaggcagagt ctcgctctgt cacccaggct    2100
ggagtgcagt ggcgccatct tggctcactg caagctccac ctcccgggtt caggccgttc   2160
tcctgcctca gcctcctgag tagctggtac cacaggcacc caccatcatg cccggctaat   2220
tttttgtatt tttagtagag atgggggtttc accttgttag ccaggatggt gtcgatctcc   2280
tgaactcgtg atccacccgc ctcggcctcc taaagtgctg ggattacaga tgtgagccac   2340
cgcacctggc cccagttgta attgtgaata tctcatacct atccctattg gcagtgtctt   2400
agttttattt tttattatct ttattgtggc agccattatt cctgtctcta tctccagtct    2460
tacatcctcc ttactgccac aagaatgatc attctaaaca tgaatcctac cctgtgactc    2520
ccatgtgact ccccgcctta aaaactgtca aaagctaccg gttacctgaa gggtaaaagt    2580
caagtcccct acttacctca tgtcatctag agcaagagat gaactagctg agttttctga    2640
ccacagtgtt ctttcttatg tatgttcttt tgtacgtgct cttttctata tagggaac     2700 catttctctc ttccagttgt tttgctcagt gaatttctat tcctgtttca aaacttgttc    2760
aggcattacc ttttttttct taagcatact ttttttaatg gaacaaagtc actcctgtct    2820
acactagttc tgcatcttat acataggttt tgtacatagt acatatttat atcacatcaa    2880
attatatgtg tttacatatc tgtcttcctt aatggaatat aagtctttg atataaggaa    2940 ctatttaatt tgtttctgtg tgttgagtat ctcctgtttg gcacagagtt caagctaata    3000
catgagagtg attagtggtg gagagccaca gtgcatgtgg tgtcaaatat ggtgcttagg    3060
aaattattgt tgcttttttga gaggtaaagg ttcatgagac tagaggtcac gaaaatcaga   3120
tttcatgtgt gaagaatgga atagatgtat tatatatgga ggaaattcta attttgtaaa   3180
aaactggatt gtgagttta aggagatgtt atataaagtt aagacaatgt cattttgtgg    3240
tattggtctg aattacaatg tagttttctta gtgatattt tcctttattc agtgcagtgc   3300
ttcagccgct accccgacca catgaagcag cacgacttct tcaagtccgc catgcccgaa   3360
ggctacgtcc aggagcgcac catcttcttc aaggacgacg gcaactacaa gaccgcgcc   3420
```

-continued

```
gaggtgaagt tcgagggcga caccctggtg aaccgcatcg agctgaaggg catcgacttc      3480
aaggaggacg gcaacatcct ggggcacaag ctggagtaca actacaacag ccacaacgtc      3540
tatatcatgg ccgacaagca gaagaacggc atcaaggtga acttcaagat ccgccacaac      3600
atcgaggacg gcagcgtgca gctcgccgac cactaccagc agaacacccc catcggcgac      3660
ggccccgtgc tgctgcccga caaccactac ctgagcaccc agtccgccct gagcaaagac      3720
cccaacgaga agcgcgatca catggtcctg ctggagttcg tgaccgccgc cgggatcact      3780
ctcggcatgg acgagctgta caagtcgagc tagcaataaa ggatcgttta ttttcattgg      3840
aagcgtgtgt tggtttttg atcaggcgcg tccaagcttg catgctgggg agagatctgc      3900
ggccgctcga gtggctccgg tgcccgtcag tgggcagagc gcacatcgcc cacagtcccc      3960
gagaagttgg ggggagggt cggcaattga accggtgcct agagaaggtg gcgcggggta      4020
aactgggaaa gtgatgtcgt gtactggctc cgccttttc ccgagggtgg gggagaaccg      4080
tatataagtg cagtagtcgc cgtgaacgtt cttttcgca acgggtttgc cgccagaaca      4140
caggtgtcgt gaccgcgggc ggccgccgct agcgctaccg gtcgccacca tggtgagcaa      4200
gggcgaggag gataacatgg ccatcatcaa ggagttcatg cgcttcaagg tgcacatgga      4260
gggctccgtg aacggccacg agttcgagat cgagggcgag ggcgagggcc gcccctacga      4320
gggcacccag accgccaagc tgaaggtgac caagggtggc cccctgccct tcgcctggga      4380
catcctgtcc cctcagttca tgtacggctc caaggcctac gtgaagcacc ccgccgacat      4440
ccccgactac ttgaagctgt ccttccccga gggcttcaag tgggagcgcg tgatgaactt      4500
cgaggacggc ggcgtggtga ccgtgaccca ggactcctcc ctgcaggacg gcgagttcat      4560
ctacaaggtg aagctgcgcg gcaccaactt cccctccgac ggccccgtaa tgcagaagaa      4620
gaccatgggc tgggaggcct cctccgagcg gatgtacccc gaggacggcg ccctgaaggg      4680
cgagatcaag cagaggctga agctgaagga cggcggccac tacgacgctg aggtcaagac      4740
cacctacaag gccaagaagc ccgtgcagct gcccggcgcc tacaacgtca acatcaagtt      4800
ggacatcacc tcccacaacg aggactacac catcgtggaa cagtacgaac gcgccgaggg      4860
ccgccactcc accggcggca tggacgagct gtacaagtga ccggtcatca tcaccatcac      4920
cattgagttt aaacccgctg atcagcctcg actgtgcctt ctagttgcca gccatctgtt      4980
gtttgcccct cccccgtgcc ttccttgacc ctggaaggtg ccactcccac tgtccttttcc      5040 taataaaatg aggaaattgc atcgcattgt ctgagtaggt gtcattctat tctggggggt      5100
ggggtggggc aggacagcaa                                                  5120
```

<210> SEQ ID NO 23
<211> LENGTH: 5120
<212> TYPE: DNA
<213> ORGANISM: Artificial Sequence
<220> FEATURE:
<223> OTHER INFORMATION: Reporter construct
      pAD27/SplitGFP+Mutant/CEP290/Kan

<400> SEQUENCE: 23

```
acataactta cggtaaatgg cccgcctggc tgaccgccca acgaccccg cccattgacg        60 tcaataatga cgtatgttcc catagtaacg ccaataggga ctttccattg acgtcaatgg      120
gtggactatt tacggtaaac tgcccacttg gcagtacatc aagtgtatca tatgccaagt      180 acgccccta ttgacgtcaa tgacggtaaa tggcccgcct ggcattatgc ccagtacatg      240
accttatggg actttcctac ttggcagtac atctacgtat tagtcatcgc tattaccatg      300
```

```
gtgatgcggt tttggcagta catcaatggg cgtggatagc ggtttgactc acggggattt     360
ccaagtctcc accccattga cgtcaatggg agtttgtttt ggcaccaaaa tcaacgggac     420 ttttccaaaat gtcgtaacaa ctccgcccca ttgacgcaaa tgggcggtag gcgtgtacgg    480
tgggaggtct atataagcag agctggttta gtgaaccgtc agatccgcta gagatccgcg     540
gccgctaata cgactcacta tagggagagc cgccaccatg gtgagcaagg gcgaggagct     600
gttcaccggg gtggtgccca tcctggtcga gctggacggc gacgtaaacg ccacaagtt      660 cagcgtgtcc ggcgagggcg agggcgatgc cacctacggc aagctgaccc tgaagttcat     720
ctgcaccacc ggcaagctgc ccgtgccctg gcccaccctc gtgaccaccc tgacctacgg     780
aggtaagttt gtgtgattct tgaaccttgt gaaattagcc attttttcttc aatatttttg    840 tgtttggggg gatttggcag attttaatta aagtttgcct gcatttatat aaatttaaca     900
gagatataat tatccatatt attcattgtg gctgaatgac ttctgaatga ttatctagat     960
cattctcctt aggtcacttg catgatttag ctgaatcaaa cctcttttaa ccagacatct     1020
aagagaaaaa ggagcatgaa acaggtagaa tattgtaatc aaaggaggga agcactcatt    1080
aagtgcccat ccctttctct taccctgta cccagaacaa actattctcc catggtccct      1140
ggcttttgtt ccttggaatg gatgtagcca acagtagctg aaatattaag ggctcttcct     1200
ggaccatgga tgcactctgt aaattctcat catttttat tgtagaataa atgtagaatt      1260
ttaatgtaga ataaatttat ttaatgtaga ataaaaaata aaaaaactag agtagaatat     1320
cataagttac aatctgtgaa tatggaccag acccttgta gttatcttac agccacttga      1380
actctatacc ttttactgag gacagaacaa gctcctgatt tgttcatctt cctcatcaga     1440
aatagaggct tatggatttt ggattattct tatctaagat cctttcacag gagtagaata     1500
agatctaatt ctattagctc aaaagctttt gctggctcat agagacacat tcagtaaatg     1560
aaaacgttgt tctgagtagc tttcaggatt cctactaaat tatgagtcat gtttatcaat     1620
attatttaga agtaatcata atcagtttgc tttctgctgc ttttgccaaa gagaggtgat     1680
tatgttactt tttatagaaa attatgccta tttagtgtgg tgataattta ttttttttcca    1740 ttctccatgt cctctgtcct atcctctcca gcattagaaa gtcctaggca agagacatct     1800
tgtggataat gtatcaatga gtgatgttta acgttatcat tttcccaaag agtattttc      1860 atctttccta aagatttttt tttttttttt ttgagatgga gtttcattct gtcacccagg     1920
ctgagtgcag tggcacgatc tcggcttaac gcttactgca tcctctgcct cccagattca     1980
agcagttctc ctgcctcagc ctctgagtag ctgggattac aggtgtgcac caccacacca    2040
gctaattttt tttttttttt ttttttttt gaggcagagt ctcgctctgt cacccaggct      2100
ggagtgcagt ggcgccatct ggctcactg caagctccac ctcccgggtt caggccgttc      2160
tcctgcctca gcctcctgag tagctggtac acaggcacc caccatcatg cccggctaat       2220
tttttgtatt tttagtagag atgggggtttc accttgttag ccaggatggt gtcgatctcc     2280
tgaactcgtg atccacccgc ctcggcctcc taaagtgctg ggattacaga tgtgagccac      2340
cgcacctggc cccagttgta attgtgagta tctcatacct atccctattg gcagtgtctt      2400
agttttattt tttattatct ttattgtggc agccattatt cctgtctcta tctccagtct     2460
tacatcctcc ttactgccac aagaatgatc attctaaaca tgaatcctac cctgtgactc     2520
ccatgtgact ccccgcctta aaaactgtca aaagctaccg gttacctgaa gggtaaaagt    2580
caagtcccct acttacctca tgtcatctaa agcaagagat gaactagctg agttttctga    2640
```

-continued

```
ccacagtgtt ctttcttatg tatgttcttt tgtacgtgct cttttctata tatagggaac    2700
catttctctc ttccagttgt tttgctcagt gaatttctat tcctgtttca aaacttgttc    2760
aggcattacc ttttttttct taagcatact tttttttaatg gaacaaagtc actcctgtct   2820
acactagttc tgcatcttat acataggttt tgtacatagt acatatttat atcacatcaa    2880
attatatgtg tttacatatc tgtcttcctt aatggaatat aagtcttttg atataaggaa    2940
ctatttaatt tgtttctgtg tgttgagtat ctcctgtttg gcacagagtt caagctaata    3000
catgagagtg attagtggtg gagagccaca gtgcatgtgg tgtcaaatat ggtgcttagg    3060
aaattattgt tgcttttttga gaggtaaagg ttcatgagac tagaggtcac gaaaatcaga   3120
tttcatgtgt gaagaatgga atagatgtat tatatatgga ggaaattcta attttgtaaa    3180
aaactggatt gtgagtttta aggagatgtt atataaagtt aagacaatgt cattttgtgg    3240
tattggtctg aattacaatg tagtttctta gtgatatttt tcctttattc agtgcagtgc    3300
ttcagccgct accccgacca catgaagcag cacgacttct tcaagtccgc catgcccgaa    3360
ggctacgtcc aggagcgcac catcttcttc aaggacgacg gcaactacaa gacccgcgcc    3420
gaggtgaagt tcgagggcga caccctggtg aaccgcatcg agctgaaggg catcgacttc    3480
aaggaggacg gcaacatcct ggggcacaag ctggagtaca actacaacag ccacaacgtc    3540
tatatcatgg ccgacaagca gaagaacggc atcaaggtga acttcaagat ccgccacaac    3600
atcgaggacg gcagcgtgca gctcgccgac cactaccagc agaacacccc catcggcgac    3660
ggccccgtgc tgctgcccga caaccactac ctgagcaccc agtccgccct gagcaaagac    3720
cccaacgaga agcgcgatca catggtcctg ctggagttcg tgaccgccgc cgggatcact    3780
ctcggcatgg acgagctgta caagtcgagc tagcaataaa ggatcgttta ttttcattgg    3840
aagcgtgtgt tggttttttg atcaggcgcg tccaagcttg catgctgggg agagatctgc    3900
ggccgctcga gtggctccgg tgcccgtcag tgggcagagc gcacatcgcc cacagtcccc    3960
gagaagttgg ggggaggggt cggcaattga accggtgcct agagaaggtg gcgcggggta    4020
aactgggaaa gtgatgtcgt gtactggctc cgcctttttc ccgagggtgg gggagaaccg    4080
tatataagtg cagtagtcgc cgtgaacgtt ctttttcgca acgggtttgc cgccagaaca    4140
caggtgtcgt gaccgcgggc ggccgccgct agcgctaccg gtcgccacca tggtgagcaa    4200
gggcgaggag gataacatgg ccatcatcaa ggagttcatg cgcttcaagg tgcacatgga    4260
gggctccgtg aacggccacg agttcgagat cgagggcgag ggcgagggcc gcccctacga    4320
gggcacccag accgccaagc tgaaggtgac caagggtggc cccctgccct tcgcctggga    4380
catcctgtcc cctcagttca tgtacggctc caaggcctac gtgaagcacc ccgccgacat    4440
ccccgactac ttgaagctgt ccttccccga gggcttcaag tgggagcgcg tgatgaactt    4500
cgaggacggc ggcgtggtga ccgtgaccca ggactcctcc ctgcaggacg gcgagttcat    4560
ctacaaggtg aagctgcgcg gcaccaactt cccctccgac ggccccgtaa tgcagaagaa    4620
gaccatgggc tgggaggcct cctccgagcg gatgtacccc gaggacggcg ccctgaaggg    4680
cgagatcaag cagaggctga agctgaagga cggcggccac tacgacgctg aggtcaagac    4740
cacctacaag gccaagaagc ccgtgcagct gcccggcgcc tacaacgtca acatcaagtt    4800
ggacatcacc tcccacaacg aggactacac catcgtggaa cagtacgaac gcgccgaggg    4860
ccgccactcc accggcggca tggacgagct gtacaagtga ccggtcatca tcaccatcac    4920
cattgagttt aaacccgctg atcagcctcg actgtgcctt ctagttgcca gccatctgtt    4980
gtttgcccct cccccgtgcc ttccttgacc ctggaaggtg ccactcccac tgtcctttcc    5040
```

```
taataaaatg aggaaattgc atcgcattgt ctgagtaggt gtcattctat tctgggggt      5100 ggggtggggc aggacagcaa                                                  5120

<210> SEQ ID NO 24
<211> LENGTH: 5120
<212> TYPE: DNA
<213> ORGANISM: Artificial Sequence
<220> FEATURE:
<223> OTHER INFORMATION: Reporter construct
      pAD28/SplitGFP+Mutant/CEP290/Inverted/Kan

<400> SEQUENCE: 24
acataactta cggtaaatgg cccgcctggc tgaccgccca acgaccccg cccattgacg        60 tcaataatga cgtatgttcc catagtaacg ccaataggga cttccattg acgtcaatgg       120 gtggactatt tacggtaaac tgcccacttg gcagtacatc aagtgtatca tatgccaagt     180 acgccccta ttgacgtcaa tgacggtaaa tggcccgcct ggcattatgc ccagtacatg      240
accttatggg actttcctac ttggcagtac atctacgtat tagtcatcgc tattaccatg     300
gtgatgcggt tttggcagta catcaatggg cgtggatagc ggtttgactc acggggattt     360
ccaagtctcc accccattga cgtcaatggg agtttgtttt ggcaccaaaa tcaacgggac     420
tttccaaaat gtcgtaacaa ctccgcccca ttgacgcaaa tgggcggtag gcgtgtacgg     480
tgggaggtct atataagcag agctggttta gtgaaccgtc agatccgcta gagatccgcg    540
gccgctaata cgactcacta tagggagagc cgccaccatg gtgagcaagg gcgaggagct    600
gttcaccggg gtggtgccca tcctggtcga gctggacggc gacgtaaacg ccacaagtt    660 cagcgtgtcc ggcgagggcg agggcgatgc cacctacggc aagctgaccc tgaagttcat    720
ctgcaccacc ggcaagctgc ccgtgccctg gcccaccctc gtgaccaccc tgacctacgg    780
aggtaagttt gtgtgattct tgaaccttgt gaaattagcc attttctc aatattttg       840 tgtttggggg gatttggcag attttaatta agtttgcct gcatttatat aaatttaaca     900
gagatataat tatccatatt attcattgtg gctgaatgac ttctgaatga ttatctagat    960
cattctcctt aggtcacttg catgatttag ctgaatcaaa cctcttttaa ccagacatct   1020
aagagaaaaa ggagcatgaa acaggtagaa tattgtaatc aaaggaggga agcactcatt   1080
aagtgcccat ccctttctct tacccctgta cccagaacaa actattctcc catggtccct   1140
ggcttttgtt ccttggaatg gatgtagcca acagtagctg aaatattaag ggctcttcct   1200
ggaccatgga tgcactctgt aaattctcat catttttat tgtagaataa atgtagaatt    1260
ttaatgtaga ataaatttat ttaatgtaga ataaaaaata aaaaaactag agtagaatat   1320
cataagttac aatctgtgaa tatgaccag acctttgta gttatcttac agccacttga   1380
actctatacg taaccggtag cttttgacag tttttaaggc ggggagtcac atgggagtca   1440
cagggtagga ttcatgttta gaatgatcat tcttgtggca gtaaggagga tgtaagactg   1500
gagatagaga caggaataat ggctgccaca ataaagataa taaaaaataa aactaagaca   1560
ctgccaatag ggataggtat gagatactca caattacaac tggggccagg tgcggtggct   1620
cacatctgta atcccagcac tttaggaggc cgaggcgggt ggatcacgag ttcaggagat   1680
cgacaccatc ctggctaaca aggtgaaacc ccatctctac taaaaataca aaaattagc    1740 cgggcatgat ggtgggtgcc tgtggtacca gctactcagg aggctgaggc aggagaacgg   1800
cctgaacccg ggaggtggag cttgcagtga gccaagatgg cgccactgca ctccagcctg   1860
ggtgacagag cgagactctg cctcaaaaaa aaaaaaaaa aaaaaaaat tagctggtgt     1920
```

```
ggtggtgcac acctgtaatc ccagctactc agaggctgag gcaggagaac tgcttgaatc   1980
tgggaggcag aggatgcagt aagcgttaag ccgagatcgt gccactgcac tcagcctggg   2040
tgacagaatg aaactccatc tcaaaaaaaa aaaaaaaaaa tctttaggaa agatgaaaaa   2100
tactctttgg gaaaatgata acgttaaaca tcactcattg atacattatc cacaagatgt   2160
ctcttgccta ggactttcta atgctggaga ggataggaca gaggacatgg agaatggaaa   2220
aaaataaatt atcaccacac taaataggca taattttcta taaaaagtaa cataatcacc   2280
tctctttggc aaaagcagca gaaagcaaac tgattatgat tacttctaaa taatattgat   2340
aaacatgact cataatttag taggaatcct gaaagctact cagaacaacg ttttcattta   2400
ctgaatgtgt ctctatgagc cagcaaaagc ttttgagcta atagaattag atcttattct   2460
actcctgtga aaggatctta gataagaata atccaaaatc cataagcctc tatttctgat   2520
gaggaagatg aacaaatcag gagcttgttc tgtcctcagt aaaagctgaa gggtaaaagt   2580
caagtcccct acttacctca tgtcatctaa agcaagagat gaactagctg agttttctga   2640
ccacagtgtt ctttcttatg tatgttcttt tgtacgtgct cttttctata tatagggaac   2700
catttctctc ttccagttgt tttgctcagt gaatttctat tcctgtttca aaacttgttc   2760
aggcattacc ttttttttct taagcatact ttttttaatg gaacaaagtc actcctgtct   2820
acactagttc tgcatcttat ataggtttt tgtacatagt acatatttat atcacatcaa   2880
attatatgtg tttacatatc tgtcttcctt aatggaatat aagtcttttg atataaggaa   2940
ctatttaatt tgtttctgtg tgttgagtat ctcctgtttg gcacagagtt caagctaata   3000
catgagagtg attagtggtg gagagccaca gtgcatgtgg tgtcaaatat ggtgcttagg   3060
aaattattgt tgcttttga gaggtaaagg ttcatgagac tagaggtcac gaaaatcaga   3120
tttcatgtgt gaagaatgga atagatgtat tatatatgga ggaaattcta attttgtaaa   3180
aaactggatt gtgagttta aggagatgtt atataaagtt aagacaatgt cattttgtgg   3240
tattggtctg aattacaatg tagtttctta gtgatatttt tcctttattc agtgcagtgc   3300
ttcagccgct acccgacca catgaagcag cacgacttct tcaagtccgc catgcccgaa   3360
ggctacgtcc aggagcgcac catcttcttc aaggacgacg gcaactacaa gacccgcgcc   3420
gaggtgaagt tcgagggcga caccctggtg aaccgcatcg agctgaaggg catcgacttc   3480
aaggaggacg gcaacatcct ggggcacaag ctggagtaca actacaacag ccacaacgtc   3540
tatatcatgg ccgacaagca gaagaacggc atcaaggtga acttcaagat ccgccacaac   3600
atcgaggacg gcagcgtgca gctcgccgac cactaccagc agaacacccc catcggcgac   3660
ggccccgtgc tgctgcccga caaccactac ctgagcaccc agtccgccct gagcaaagac   3720
cccaacgaga agcgcgatca catggtcctg ctggagttcg tgaccgccgc cgggatcact   3780
ctcggcatgg acgagctgta caagtcgagc tagcaataaa ggatcgttta ttttcattgg   3840
aagcgtgtgt tggttttttg atcaggcgcg tccaagcttg catgctgggg agagatctgc   3900
ggccgctcga gtggctccgg tgcccgtcag tgggcagagc gcacatcgcc cacagtcccc   3960
gagaagttgg ggggaggggt cggcaattga accggtgcct agagaaggtg gcgcggggta   4020
aactgggaaa gtgatgtcgt gtactggctc cgcctttttc ccgagggtgg gggagaaccg   4080
tatataagtg cagtagtcgc cgtgaacgtt ctttttcgca acgggtttgc cgccagaaca   4140
caggtgtcgt gaccgcgggc ggcgccgcct agcgctaccg gtcgccacca tggtgagcaa   4200
gggcgaggag gataacatgg ccatcatcaa ggagttcatg cgcttcaagg tgcacatgga   4260
```

-continued

```
gggctccgtg aacggccacg agttcgagat cgagggcgag ggcgagggcc gcccctacga   4320
gggcacccag accgccaagc tgaaggtgac caagggtggc cccctgccct tcgcctggga   4380
catcctgtcc cctcagttca tgtacggctc caaggcctac gtgaagcacc ccgccgacat   4440
ccccgactac ttgaagctgt ccttccccga gggcttcaag tgggagcgcg tgatgaactt   4500
cgaggacggc ggcgtggtga ccgtgaccca ggactcctcc ctgcaggacg gcgagttcat   4560
ctacaaggtg aagctgcgcg gcaccaactt cccctccgac ggccccgtaa tgcagaagaa   4620
gaccatgggc tgggaggcct cctccgagcg gatgtacccc gaggacggcg ccctgaaggg   4680
cgagatcaag cagaggctga agctgaagga cggcggccac tacgacgctg aggtcaagac   4740
cacctacaag gccaagaagc ccgtgcagct gcccggcgcc tacaacgtca acatcaagtt   4800
ggacatcacc tcccacaacg aggactacac catcgtggaa cagtacgaac gcgccgaggg   4860
ccgccactcc accggcggca tggacgagct gtacaagtga ccggtcatca tcaccatcac   4920
cattgagttt aaacccgctg atcagcctcg actgtgcctt ctagttgcca gccatctgtt   4980
gtttgcccct cccccgtgcc ttccttgacc ctggaaggtg ccactcccac tgtcctttcc   5040
taataaaatg aggaaattgc atcgcattgt ctgagtaggt gtcattctat tctggggggt   5100
ggggtggggc aggacagcaa                                              5120
```

<210> SEQ ID NO 25
<211> LENGTH: 3944
<212> TYPE: DNA
<213> ORGANISM: Artificial Sequence
<220> FEATURE:
<223> OTHER INFORMATION: Reporter construct
pAD29/SplitGFP+Deletion/CEP290/Kan

<400> SEQUENCE: 25

```
acataactta cggtaaatgg cccgcctggc tgaccgccca acgaccccg cccattgacg    60 tcaataatga cgtatgttcc catagtaacg ccaataggga cttccattg acgtcaatgg   120 gtggactatt tacggtaaac tgcccacttg gcagtacatc aagtgtatca tatgccaagt   180 acgccccta ttgacgtcaa tgacggtaaa tggcccgcct ggcattatgc ccagtacatg   240
accttatggg actttcctac ttggcagtac atctacgtat tagtcatcgc tattaccatg   300
gtgatgcggt tttggcagta catcaatggg cgtggatagc ggtttgactc acggggattt   360
ccaagtctcc accccattga cgtcaatggg agtttgtttt ggcaccaaaa tcaacgggac   420
tttccaaaat gtcgtaacaa ctccgcccca ttgacgcaaa tgggcggtag gcgtgtacgg   480
tgggaggtct atataagcag agctggttta gtgaaccgtc agatccgcta gagatccgcg   540
gccgctaata cgactcacta tagggagagc cgccaccatg gtgagcaagg gcgaggagct   600
gttcaccggg gtggtgccca tcctggtcga gctggacggc gacgtaaacg gccacaagtt   660
cagcgtgtcc ggcgagggcg agggcgatgc cacctacggc aagctgaccc tgaagttcat   720
ctgcaccacc ggcaagctgc ccgtgccctg gccaccctc gtgaccaccc tgacctacgg   780
aggtaagttt gtgtgattct tgaaccttgt gaaattagcc attttcttc aatatttttg   840 tgtttggggg gatttggcag attttaatta agtttgcct gcatttatat aaatttaaca   900
gagatataat tatccatatt attcattgtg gctgaatgac ttctgaatga ttatctagat   960
cattctcctt aggtcacttg catgatttag ctgaatcaaa cctcttttaa ccagacatct  1020
aagagaaaaa ggagcatgaa acaggtagaa tattgtaatc aaaggaggga agcactcatt  1080
aagtgcccat ccctttctct taccccctgta cccagaacaa actattctcc catggtccct  1140
```

```
ggcttttgtt ccttggaatg gatgtagcca acagtagctg aaatattaag ggctcttcct   1200
ggaccatgga tgcactctgt aaattctcat cattttttat tgtagaataa atgtagaatt   1260
ttaatgtaga ataaatttat ttaatgtaga ataaaaaata aaaaaactag agtagaatat   1320
cataagttac aatctgtgaa tatggaccag acccttgta gttatcttac agccacttga    1380
actctatacc tgaagggtaa aagtcaagtc ccctacttac ctcatgtcat ctaaagcaag   1440
agatgaacta gctgagtttt ctgaccacag tgttctttct tatgtatgtt cttttgtacg   1500
tgctcttttc tatatatagg gaaccatttc tctcttccag ttgttttgct cagtgaattt   1560
ctattcctgt ttcaaaactt gttcaggcat tacctttttt ttcttaagca tactttttt    1620
aatggaacaa agtcactcct gtctacacta gttctgcatc ttatacatag gttttgtaca   1680
tagtacatat ttatatcaca tcaaattata tgtgtttaca tatctgtctt ccttaatgga   1740
atataagtct tttgatataa ggaactattt aatttgtttc tgtgtgttga gtatctcctg   1800
tttggcacag agttcaagct aatacatgag agtgattagt ggtggagagc cacagtgcat   1860
gtggtgtcaa atatggtgct taggaaatta ttgttgcttt tgagaggta aaggttcatg    1920
agactagagg tcacgaaaat cagatttcat gtgtgaagaa tggaatagat gtattatata   1980
tggaggaaat tctaattttg taaaaaactg gattgtgagt tttaaggaga tgttatataa   2040
agttaagaca atgtcatttt gtggtattgg tctgaattac aatgtagttt cttagtgata   2100
ttttttcctt attcagtgca gtgcttcagc cgctaccccg accacatgaa gcagcacgac   2160
ttcttcaagt ccgccatgcc cgaaggctac gtccaggagc gcaccatctt cttcaaggac   2220
gacggcaact acaagacccg cgccgaggtg aagttcgagg gcgacaccct ggtgaaccgc   2280
atcgagctga agggcatcga cttcaaggag gacggcaaca tcctggggca caagctggag   2340
tacaactaca acagccacaa cgtctatatc atggccgaca gcagaagaa cggcatcaag    2400
gtgaacttca agatccgcca caacatcgag gacggcagcg tgcagctcgc cgaccactac   2460
cagcagaaca cccccatcgg cgacggcccc gtgctgctgc ccgacaacca ctacctgagc   2520
acccagtccg ccctgagcaa agaccccaac gagaagcgcg atcacatggt cctgctggag   2580
ttcgtgaccg ccgccgggat cactctcggc atggacgagc tgtacaagtc gagctagcaa   2640
taaaggatcg tttatttttca ttggaagcgt gtgttggttt tttgatcagg cgcgtccaag   2700
cttgcatgct ggggagagat ctgcggccgc tcgagtggct ccggtgcccg tcagtgggca   2760
gagcgcacat cgcccacagt ccccgagaag ttgggggggag gggtcggcaa ttgaaccggt   2820
gcctagagaa ggtggcgcgg ggtaaactgg gaaagtgatg tcgtgtactg gctccgcctt   2880
tttcccgagg gtgggggaga accgtatata agtgcagtag tcgccgtgaa cgttcttttt   2940
cgcaacgggt ttgccgccag aacacaggtg tcgtgaccgc gggcggccgc cgctagcgct   3000
accggtcgcc accatggtga gcaagggcga ggaggataac atggccatca tcaaggagtt   3060
catgcgcttc aaggtgcaca tggagggctc cgtgaacggc cacgagttcg agatcgaggg   3120
cgagggcgag ggccgcccct acgagggcac ccagaccgcc aagctgaagg tgaccaaggg   3180
tggccccctg cccttcgcct gggacatcct gtcccctcag ttcatgtacg gctccaaggc   3240
ctacgtgaag caccccgccg acatccccga ctacttgaag ctgtccttcc ccgagggctt   3300
caagtgggag cgcgtgatga acttcgagga cggcggcgtg gtgaccgtga cccaggactc   3360
ctccctgcag gacggcgagt tcatctacaa ggtgaagctg cgcggcacca acttcccctc   3420
cgacggcccc gtaatgcaga agaagaccat gggctgggag gcctcctccg agcggatgta   3480
ccccgaggac ggcgccctga agggcgagat caagcagagg ctgaagctga aggacggcgg   3540
```

```
ccactacgac gctgaggtca agaccaccta caaggccaag aagcccgtgc agctgcccgg    3600
cgcctacaac gtcaacatca agttggacat cacctcccac aacgaggact acaccatcgt    3660
ggaacagtac gaacgcgccg agggccgcca ctccaccggc ggcatggacg agctgtacaa    3720
gtgaccggtc atcatcacca tcaccattga gtttaaaccc gctgatcagc ctcgactgtg    3780
ccttctagtt gccagccatc tgttgtttgc ccctcccccg tgccttcctt gaccctggaa    3840
ggtgccactc ccactgtcct ttcctaataa aatgaggaaa ttgcatcgca ttgtctgagt    3900
aggtgtcatt ctattctggg gggtggggtg gggcaggaca gcaa                     3944
```

<210> SEQ ID NO 26
<211> LENGTH: 22
<212> TYPE: RNA
<213> ORGANISM: Artificial Sequence
<220> FEATURE:
<223> OTHER INFORMATION: Targeting domain

<400> SEQUENCE: 26
guucuguccu caguaaaagg ua                                              22

<210> SEQ ID NO 27
<211> LENGTH: 20
<212> TYPE: RNA
<213> ORGANISM: Artificial Sequence
<220> FEATURE:
<223> OTHER INFORMATION: Targeting domain

<400> SEQUENCE: 27
gaauaguuug uucuggguac                                                 20

<210> SEQ ID NO 28
<211> LENGTH: 20
<212> TYPE: RNA
<213> ORGANISM: Artificial Sequence
<220> FEATURE:
<223> OTHER INFORMATION: Targeting domain

<400> SEQUENCE: 28
gagaaaggga ugggcacuua                                                 20

<210> SEQ ID NO 29
<211> LENGTH: 22
<212> TYPE: RNA
<213> ORGANISM: Artificial Sequence
<220> FEATURE:
<223> OTHER INFORMATION: Targeting domain

<400> SEQUENCE: 29
gucaaaagcu accgguuacc ug                                              22

<210> SEQ ID NO 30
<211> LENGTH: 20
<212> TYPE: RNA
<213> ORGANISM: Artificial Sequence
<220> FEATURE:
<223> OTHER INFORMATION: Targeting domain

<400> SEQUENCE: 30
gaugcagaac uaguguagac                                                 20

<210> SEQ ID NO 31
<211> LENGTH: 19
<212> TYPE: RNA

```
<213> ORGANISM: Artificial Sequence
<220> FEATURE:
<223> OTHER INFORMATION: Targeting domain

<400> SEQUENCE: 31
gaguaucucc uguuuggca                                                  19

<210> SEQ ID NO 32
<211> LENGTH: 102
<212> TYPE: RNA
<213> ORGANISM: Artificial Sequence
<220> FEATURE:
<223> OTHER INFORMATION: S. aureus gRNA
<220> FEATURE:
<221> NAME/KEY: misc_feature
<222> LOCATION: (1)..(20)
<223> OTHER INFORMATION: Targeting domain of 16-24 nts, each n is a, c,
      u, g, unknown, or other

<400> SEQUENCE: 32
nnnnnnnnnn nnnnnnnnnn guuuuaguac ucuggaaaca gaaucuacua aaacaaggca     60
aaaugccgug uuuaucucgu caacuuguug gcgagauuuu uu                       102

<210> SEQ ID NO 33
<211> LENGTH: 102
<212> TYPE: RNA
<213> ORGANISM: Artificial Sequence
<220> FEATURE:
<223> OTHER INFORMATION: S. aureus gRNA
<220> FEATURE:
<221> NAME/KEY: misc_feature
<222> LOCATION: (1)..(20)
<223> OTHER INFORMATION: Targeting domain of 16-24 nts, each n is a, c,
      u, g, unknown, or other

<400> SEQUENCE: 33
nnnnnnnnnn nnnnnnnnnn guuauaguac ucuggaaaca gaaucuacua uaacaaggca     60
aaaugccgug uuuaucucgu caacuuguug gcgagauuuu uu                       102

<210> SEQ ID NO 34
<211> LENGTH: 36
<212> TYPE: DNA
<213> ORGANISM: Mus musculus

<400> SEQUENCE: 34
cagaactcgg tcaggcatgc tacagatagc ttatct                               36

<210> SEQ ID NO 35
<211> LENGTH: 31
<212> TYPE: DNA
<213> ORGANISM: Mus musculus

<400> SEQUENCE: 35
cagaactcgg catgctacag atagcttatc t                                    31

<210> SEQ ID NO 36
<211> LENGTH: 9
<212> TYPE: DNA
<213> ORGANISM: Mus musculus

<400> SEQUENCE: 36 ccctcaaag                                                              9

<210> SEQ ID NO 37
<211> LENGTH: 21
```

```
<212> TYPE: DNA
<213> ORGANISM: Mus musculus

<400> SEQUENCE: 37
catgctacag atagcttatc t                                             21

<210> SEQ ID NO 38
<211> LENGTH: 21
<212> TYPE: RNA
<213> ORGANISM: Artificial Sequence
<220> FEATURE:
<223> OTHER INFORMATION: C1 targeting domain

<400> SEQUENCE: 38
ggccggcuaa uuuaguagag a                                             21

<210> SEQ ID NO 39
<211> LENGTH: 20
<212> TYPE: RNA
<213> ORGANISM: Artificial Sequence
<220> FEATURE:
<223> OTHER INFORMATION: C2 targeting domain

<400> SEQUENCE: 39
guuaugaaga auaauacaaa                                               20
```